(12) United States Patent
Detlef Sorensen et al.

(10) Patent No.: US 8,492,390 B2
(45) Date of Patent: Jul. 23, 2013

(54) SYNTHESIS OF LOCKED NUCLEIC ACID DERIVATIVES

(75) Inventors: Mads Detlef Sorensen, København (DK); Jesper Wengel, Odense S (DK); Troels Koch, København (DK); Signe M. Christensen, København (DK); Christoph Rosenbohm, Copenhagen (DK); Daniel Sejer Pedersen, Cambridge (DK)

(73) Assignee: Santaris Pharma A/S, Hoersholm (DK)

( * ) Notice: Subject to any disclaimer, the term of this patent is extended or adjusted under 35 U.S.C. 154(b) by 0 days.

(21) Appl. No.: 13/336,303

(22) Filed: Dec. 23, 2011

(65) Prior Publication Data

US 2012/0165514 A1    Jun. 28, 2012

Related U.S. Application Data

(62) Division of application No. 12/534,711, filed on Aug. 3, 2009, now Pat. No. 8,084,458, which is a division of application No. 10/435,607, filed on May 8, 2003, now Pat. No. 7,569,575.

(60) Provisional application No. 60/378,689, filed on May 8, 2002, provisional application No. 60/404,242, filed on Aug. 16, 2002.

(51) Int. Cl.
| | |
|---|---|
| C07D 473/06 | (2006.01) |
| C07D 473/16 | (2006.01) |
| C07D 473/18 | (2006.01) |
| C07D 473/34 | (2006.01) |
| C07D 473/40 | (2006.01) |
| C07D 239/70 | (2006.01) |
| C07D 239/52 | (2006.01) |
| A61P 31/22 | (2006.01) |

(52) U.S. Cl.
USPC ...... 514/263.23; 544/272; 544/311; 544/314; 544/317; 514/274

(58) Field of Classification Search
USPC .................. 549/214, 355, 397; 514/63, 450, 514/456
See application file for complete search history.

(56) References Cited

U.S. PATENT DOCUMENTS 6,268,490 B1    7/2001    Imanishi et al. ............. 536/23.1

FOREIGN PATENT DOCUMENTS

| WO | WO 98/39352 | 9/1998 |
| WO | WO 99/14226 | 3/1999 |
| WO | WO 00/66604 | 11/2000 |
| WO | WO 02/28875 A2 | 4/2002 |

OTHER PUBLICATIONS

S. Singh et al., *J. Org. Chem.*, 63:10035-10039 (1998).
S. Singh et al., *J. Org. Chem.*, 63:6078-6079 (1998).
R. Kumar et al., *Biorg. Med. Chem. Lett.*, 8:2219-2222 (1998).
A. Koshkin et al., *Tetrahedron*, 54:3607-3630 (1998).
S. Obika et al., *Tet. Lett.*, 38:8735-8738 (1997).
A. Koshkin et al., *J. Org. Chem.*, 66:8504-8512 (2001).
R. Youssefyeh et al., *J. Org. Chem.*, 44:1301-1309 (1979).
A. Hakansson et al., *J. Org. Chem.*, 65:5161-5166 (2000).
S. Singhet al., *Chem. Commun.*, 455-456 (1998).
V. Rajwanshi et al., *Chem. Commun.*, 1395-1396 (1999).
U. Jordis et al., *Indian Journal of Chemistry*, vol. 28B, pp. 294-296 (1989).
L. Kværno et al., *J. Org. Chem.*, vol. 66, pp. 5106-5112 (2001).
V. Popsavin et al., *Carbohydrate Research*, vol. 269, pp. 343-347 (1995).
G. Fleet et al., *Tetrahedron*, vol. 42, No. 20, pp. 5685-5692 (1986).
C. Rosenbohm et al., *Org. & Biomol. Chem.*, pp. 655-663 (2003).
T. Bryld et al., *J. Chem. Soc., Perkin Trans*, vol. 1, pp. 1655-1662 (2002).

*Primary Examiner* — Susanna Moore
(74) *Attorney, Agent, or Firm* — Fish & Richardson P.C.

(57) ABSTRACT

The invention relates to a novel strategy for the synthesis of Locked Nucleic Acid derivatives, such as α-L-oxy-LNA, amino-LNA, α-L-amino-LNA, thio-LNA, α-L-thio-LNA, seleno-LNA and methylene LNA, which provides scalable high yielding reactions utilising intermediates that also can produce other LNA analogues such as oxy-LNA. Also, the compounds of the formula X are important intermediates that may be reacted with varieties of nucleophiles leading to a wide variety of LNA analogues.

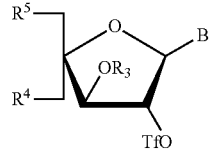

Formula X

8 Claims, 12 Drawing Sheets

SYNTHESIS OF LOCKED NUCLEIC ACID DERIVATIVES

CROSS-REFERENCE TO RELATED APPLICATIONS

This application claims the priority to U.S. application Ser. No. 12/534,711, filed Aug. 3, 2009, as a divisional application which claims the priority to U.S. application Ser. No. 10/435,607, filed May 8, 2003, as a divisional application. U.S. application Ser. No. 10/435,607 claims the benefit of U.S. Provisional Application Ser. No. 60/378,689, filed May 8, 2002 and 60/404,242 filed Aug. 16, 2002, all of which are incorporated herein by reference.

FIELD OF THE INVENTION

The present invention relates to a novel strategy for the synthesis of Locked Nucleic Acid derivatives, such as amino-LNA, thio-LNA, seleno-LNA and methylene-LNA, which provides scalable high yielding reactions utilising intermediates that also can produce other LNA analogues such as oxy-LNA. The invention further relates to a novel strategy for the synthesis of α-L-LNA analogues and precursors.

BACKGROUND OF THE INVENTION

Professor Imanishi (WO 98/39352) and Professor Wengel (WO 99/14226) independently invented Locked Nucleic Acid (LNA) in 1997 and the first LNA monomer was based on the 2'-O—$CH_2$-4' bicyclic structure (oxy-LNA). This LNA analogue has since then showed promising results as antisense drug candidates. Other LNA analogues has also been synthesized exhibiting similar high affinity/specificity for example 2'—NH—$CH_2$-4', 2'—N($CH_3$)— $CH_2$-4' (amino-LNA) (Singh, S. K.; Kumar, R.; Wengel, J. *J. Org. Chem.* 1998, 63, 10035-10039; Singh, S. K.; Kumar, R.; Wengel, J. *J. Org. Chem.* 1998, 63, 6078-6079), and 2'-S—$CH_2$-4' (thio-LNA) (Singh, S. K.; Kumar, R.; Wengel, J. *J. Org. Chem.* 1998, 63, 6078-6079, Kumar, R.; Singh, S. K et al. *Biorg. Med. Chem. Lett.* 1998, 8, 2219-2222). Large quantities of amino-LNA are crucial for its use in antisense. Scaling-up the previously described method of synthesis of amino-LNA has appeared to be difficult and encountered several major problems.

The first difficult reaction in the scale up work proved to be the regioselective benzylation of 3-O-benzyl-1,2-O-isopropylidene-4-C-hydroxymethyl-α-D-erythro-pentofuranose (Koshkin, A.; Singh, S. K.; Nielsen, P.; Rajwanshi, V. K.; Kumar, R.; Meldgaard, M.; Olsen, C. E.; Wengel, J. *Tetrahedron* 1998, 54, 3607-3630) (see FIG. 1, compound 1).

Working in the 100 g range the reaction yielded a product-mixture of compound 2, the 1'-benzylated and the di-benzylated material even under optimised conditions. The maximum yield of the desired compound 2 was 59% dropping to an average of 45-50% compared to 71% on smaller scale. Furthermore, compound 2 could only be isolated through tedious chromatography of closely eluting products.

The second key step in the original strategy causing problems during scale-up synthesis was the double nucleophilic substitution of the di-O-tosyl nucleoside 5 using benzylamine giving nucleoside 6 (Singh, S. K.; Kumar, R.; Wengel, J. *J. Org. Chem.* 1998, 63, 10035-10039). The reaction on larger scale (22 g) apparently afforded a second product identified as the oxy-LNA derivative. The desired N-benzylated-amino-LNA product 6 was obtained in only 15% together with 13% of the oxy-LNA by-product. For comparison, the reaction gives 52% of nucleoside 6 on a 8 g scale with no side reaction reported (Singh, S. K.; Kumar, R.; Wengel, J. *J. Org. Chem.* 1998, 63, 10035-10039).

Yet another problem encountered appeared to be the debenzylation of nucleoside 6 using ammonium formate and 10% Pd/C in methanol. It appeared to be only partial debenzylation as verified by mass spectroscopy, and the product 7 proved to be difficult to isolate from the reaction mixture.

The first synthesis of an oxy-LNA nucleoside was performed by a linear approach using uridine as starting material (Obika, S.; Nanbu, D.; Hari, Y.; Morio, J. A. K.; In, Y.; Ishida, T.; Imanishi, T. *Tet. Lett.* 1997, 38, 8735-8738) but by virtue of being a convergent synthesis the route developed by Wengel and coworker (Koshkin, A.; Singh, S. K.; Nielsen, P.; Rajwanshi, V. K.; Kumar, R.; Meldgaard, M.; Olsen, C. E.; Wengel, J. Tetrahedron 1998, 54, 3607-3630; Koshkin, A. A. et al., *J. Org. Chem.* 2001, 66, 8504-8512) became the method of choice for the synthesis of LNA nucleosides.

Amino- and thio-LNA was originally synthesised quite differently, but according to the present invention there are common intermediates that can be used for amino-LNA, thio-LNA, seleno-LNA, α-L-LNA as well as methylene-LNA at late stages in the overall synthesis.

SUMMARY OF THE INVENTION

The present invention provides a novel strategy for the synthesis of LNA derivatives, such as α-L-oxy-LNA, amino-LNA, α-L-amino-LNA, thio-LNA, α-L-thio-LNA, seleno-LNA and methylene-LNA.

The compounds of the formula I are important intermediates that may be reacted with varieties of nucleophiles leading to a wide variety of LNA analogues, e.g. amino-LNA, thio-LNA, seleno-LNA and methylene-LNA.

One aspect of the invention relates to a method for synthesis of LNA analogues of the formula IV starting from compounds of formula I, cf. claim 1.

Another aspect of the present invention relates to the novel compounds (intermediates) of the formula I as defined in claim 33.

Still another aspect of the present invention relates to a method for synthesis of the compounds (intermediates) of the formula I, cf. claim 19.

A further object of the invention is to provide a method for the synthesis of α-L-LNA analogues of the formula VIII, from an intermediate of the general formula IX, cf. claim 45.

The main advantages of the present invention comprises the following:
tedious separation of regioisomers is eliminated,
the low-yielding step of double nucleophilic substitution of di-O-tosyl nucleoside using benzylamine is avoided,
the method enables the utilisation of a starting intermediates which is common to the known oxy-LNA synthesis,
the method comprises a novel intermediate that when reacted with appropriate nucleophilic can produce a variety of LNA analogues, i.e. amino-LNA, thio-LNA, seleno-LNA, methylene-LNA, and α-L-LNA,
the method comprises an alternative method for N-methylation, and hereby avoids methylation at the nucleobase,
employs cheap and commercial available reagents,
comprises scalable reactions giving access to large quantities of LNA analogue phosphoramidites.

DETAILED DESCRIPTION OF THE INVENTION

Synthesis of LNA Analogues

Figure 1:
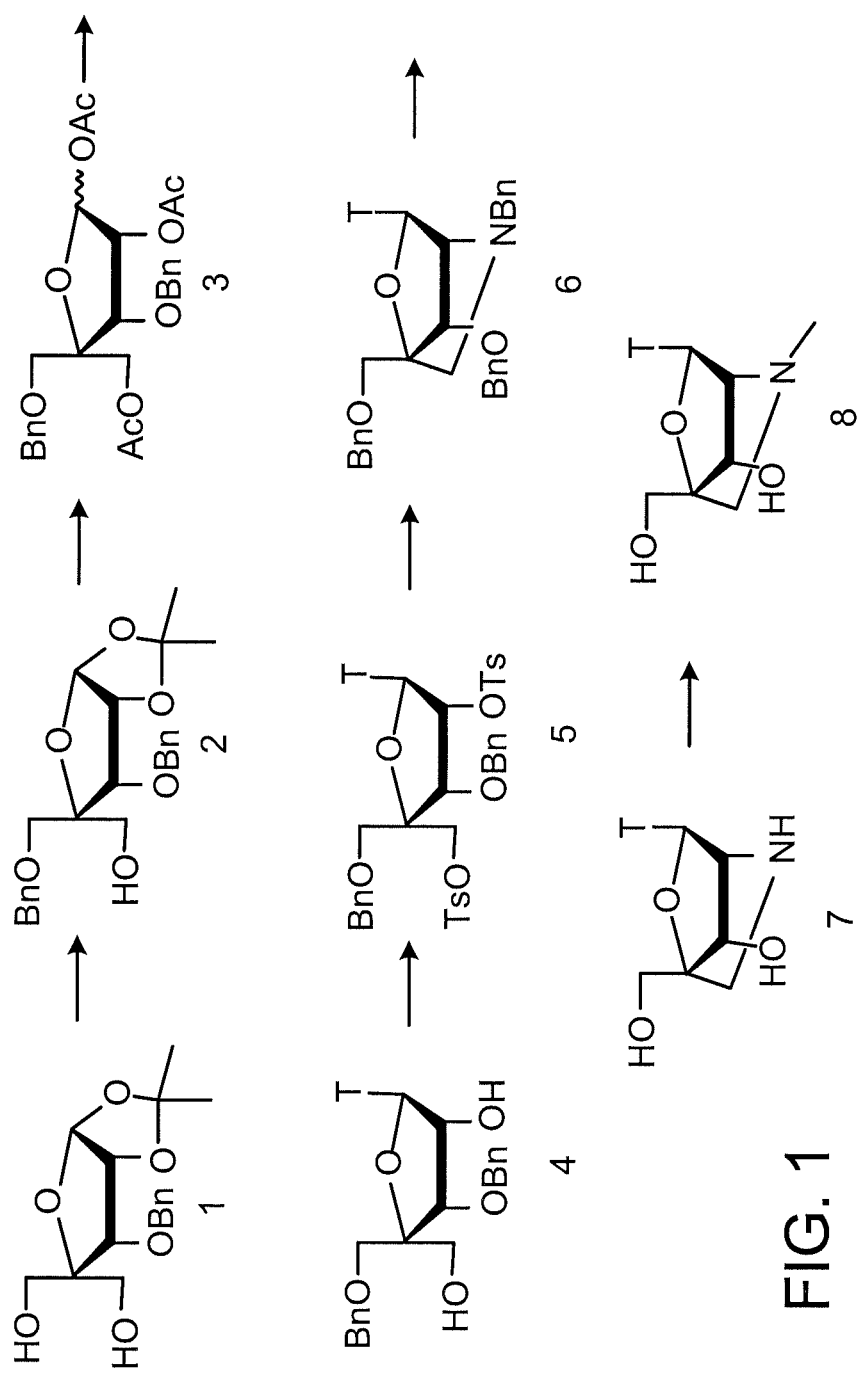
FIG. 1 illustrates a known method for the preparation of amino-LNA according to Singh, S. K.; Kumar, R.; Wengel, J. *J. Org. Chem.* 1998, 63, 10035-10039.

A main aspect of the present invention relates to a method for the synthesis an LNA analogue of the general formula IV

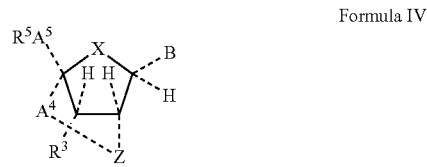

Formula IV wherein

X is selected from —$CH_2$—, —$NR^H$—, —O—, and —S—;

Z is selected from —$CH_2$—, —$NR^H$—, —S—, and —Se—;

B is a nucleobase;

$R^3$ is selected from —$R^H$, —$N_3$, —$NR^HR^{H*}$, —$NR^HC(O)R^{H*}$, —$C(O)NR^HR^{H*}$, —$OR^H$, —$OC(O)R^H$, —$C(O)OR^H$, —$SR^H$, —$SC(O)R^N$, and tri($C_{1-6}$-alkyliaryl)silyloxy;

each $R^H$ and $R^{H*}$ independently being selected from hydrogen, optionally substituted $C_{1-6}$-alkyl, optionally substituted aryl, and optionally substituted aryl-$C_{1-6}$-alkyl;

$A^4$ and $A^5$ independently are selected from $C_{1-6}$-alkylene; and $R^5$ is selected from iodo, bromo, chloro, $C_{1-6}$-alkylsulfonyloxy optionally substituted with one or more substituents selected from halogen and phenyl optionally substituted with one or more substituents selected from nitro, halogen and $C_{1-6}$-alkyl, and arylsulfonyloxy optionally substituted with one or more substituents selected from nitro, halogen, $C_{1-6}$-alkyl, and $C_{1-6}$-alkyl substituted with one or more halogen;

said method comprising the following steps:

treating an intermediate of the general formula I:

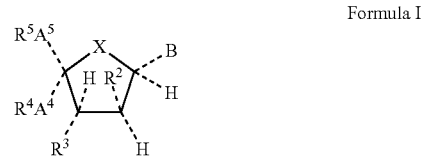

Formula I wherein

X, B, $R^3$, $A^4$, and $A^5$ are as defined above;

$R^2$ is selected from iodo, $C_{1-6}$-alkylsulfonyloxy optionally substituted with one or more substituents selected from halogen and phenyl optionally substituted with one or more substituents selected from nitro, halogen and $C_{1-6}$-alkyl, and arylsulfonyloxy optionally substituted with one or more substituents selected from nitro, halogen, $C_{1-6}$-alkyl, and $C_{1-6}$-alkyl substituted with one or more halogen;

$R^3$ and $R^2$ may together form an epoxide and $R^4$ and $R^5$ independently are as defined for $R^5$ above, or $R^4$ and $R^5$ together constitutes a tetra($C_{1-6}$-alkyl)disiloxanylidene group;

with a nucleophile selected from halogen, $^-N_3$, $^-NR^HR^{H*}$, $^-SR^H$, $^-S$, $^-SeR^H$, $^-Se$ $^-NR^HC(O)R^{H*}$, $^-SC(O)R^H$, and organometallic hydrocarbyl radicals, so as to substitute $R^2$, and effecting ring-closure between the C2' and C4' positions so as to yield the LNA analogue of the formula IV.

It has been found that the intermediates of the formula I play an important role in the synthesis of the LNA analogues. Hence, the particular selection of substituents in the intermediates has proved to be important for the efficient route to the LNA analogues. It should be understood that the substituents X, B, $R^3$, $A^4$, $A^5$, and $R^5$ most often will be unaltered in the synthesis, i.e. these substituents will be "carried over" from Formula I to formula IV. Also the absolute orientation of these substituents will also be preserved.

This being said, it may be necessary to protect the nucleobase as will be appreciated by the person skilled in the art (see further below under the definition of "nucleobase" and FIG. 3).

In an interesting embodiment, the substituents of the compound of the formula I are selected so that $R^2$ is selected from $C_{1-5}$-alkylsulfonyloxy optionally substituted with one or more substituents selected from halogen and phenyl optionally substituted with one or more substituents selected from nitro, halogen and $C_{1-6}$-alkyl, and arylsulfonyloxy optionally substituted with one or more substituents selected from nitro, halogen, $C_{1-6}$-alkyl, and $C_{1-6}$-alkyl substituted with one or more halogen;

$R^3$ is optionally substituted aryl($C_{1-6}$-alkyl)oxy; and $R^4$ and $R^5$ are independently selected from $C_{1-6}$-alkylsulfonyloxy optionally substituted with one or more substituents selected from halogen and phenyl optionally substituted with one or more substituents selected from nitro, halogen and $C_{1-5}$-alkyl, and arylsulfonyloxy optionally substituted with one or more substituents selected from nitro, halogen, $C_{1-5}$-alkyl, and $C_{1-6}$-alkyl substituted with one or more halogen.

Also, interesting is the embodiments where $A^4$ and $A^5$ are both methylene, as well as the embodiments where X is —O—.

Although the configuration of the intermediate (Formula I) is generally open, it is presently believed that one interesting configuration for the intermediate is represented by the formula II

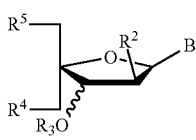

Formula II wherein B, $R^2$, $R^3$, $R^4$, and $R^5$ are as defined above. This being said, the mirror-image of formula II may be equally applicable. In one embodiment $OR^3$ and $R^2$ may form an epoxide.

In a particularly interesting embodiment, the substituents of the intermediate (Formula I or Formula II) are chosen so that B is selected from adenine, guanine, 2,6-diaminopurine, thymine, 2-thiothymine, cytosine, methyl cytosine, uracil, 5-fluorocytosine, xanthine, 6-aminopurine, 2-aminopurine, 6-chloro-2-amino-purine, and 6-chloropurine, $R^2$ is selected from $C_{1-5}$-alkylsulfonyloxy substituted with one or more halogen, $R^3$ is benzyl, and $R^4$ and $R^5$ are independently selected from $C_{1-6}$-alkylsulfonyloxy optionally substituted with one or more substituents selected from halogen and phenyl optionally substituted with one or more substituents selected from nitro, halogen and $C_{1-6}$-alkyl, and arylsulfonyloxy optionally substituted with one or more substituents selected from nitro, halogen, $C_{1-6}$-alkyl, and $C_{1-6}$-alkyl substituted with one or more halogen.

The substituents $R^4$ and $R^5$ are preferably identical in that offers advantages in the preparation of the intermediate (see further below).

Particular examples of the groups (independently) applicable as $R^4$ and $R^5$ are methanesulfonyloxy, trifluoromethanesulfonyloxy, ethanesulfonyloxy, 2,2,2-trifluoroethanesulfonyloxy, propanesulfonyloxy, iso-propanesulfonyloxy, butanesulfonyloxy, nonafluorobutanesulfonyloxy, pentanesulfonyloxy, cyclopentanesulfonyloxy, hexanesulfonyloxy, cyclohexanesulfonyloxy, α-toluenesulfonyloxy, 2-chloro-α-toluenesulfonyloxy, ortho-toluenesulfonyloxy, meta-toluenesulfonyloxy, para-toluenesulfonyloxy, benzenesulfonyl-oxy, ortho-bromobenzenesulfonyloxy, meta-bromobenzenesulfonyloxy, para-bromo-benzenesulfonyloxy, ortho-nitrobenzenesulfonyloxy, meta-nitrobenzenesulfonyloxy, and para-nitrobenzenesulfonyloxy. The currently most promising group is methanesulfonyloxy.

In one particularly interesting variant, the intermediate has the formula III

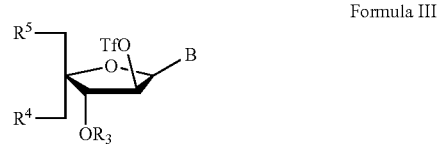

Formula III wherein B, $R^3$, $R^4$ and $R^5$ are as defined above.

A further interesting variant (in combination with Formula I, Formula II or Formula III) is where the substituents are chosen so that B is selected from adenine, guanine, 2,6-diaminopurine, thymine, 2-thiothymine, cytosine, methyl cytosine, uracil, 5-fluorocytosine, xanthine, 6-aminopurine, 2-aminopurine, 6-chloro-2-amino-purine, and 6-chloropurine, $R^3$ is benzyl, and $R^4$ and $R^5$ are both methanesulfonyloxy. In particular, $A^4$ and $A^5$ are preferably both methylene.

The intermediate of Formula I is reacted with a nucleophile selected from halogen, $^-N_3$, $^-NR^HR^{H*}$, $^-SR^H$, $^{--}S$, $^-NR^HC(O)R^{H*}$, $—SC(O)R^H$, and organometallic hydrocarbyl radicals, so as to substitute $R^2$.

It is currently believed that the substitution of $R^2$ proceeds via a $S_N2$ mechanism with inversion of the relative orientation of the substituent in the C2' position.

The "C2' position" refers to the normal nomenclature for nucleosides, where the carbon carrying the nucleobase B is C1', the carbon carrying $R^2$ (or $R^{2*}$) is C2', and the carbon carrying $R^4A^4$ is C4'.

The organometallic hydrocarbyl radicals typically has the formula $MR^H$ where M is a metal such as Mg (e.g. in the form 12"MgBr prepared from the halide and magnesium (Grignard)), Cu ($R^H{}_2CuLi$ e.g. prepared from $2R^HLi+CuI$), Li (e.g. BuLi)), etc.

The organometallic hydrocarbyl radicals are applicable for the preparation of LNA analogues where Z is —$CH_2$— (methylene-LNA). The sulphur nucleophiles are of course applicable where Z is —S—, and the nitrogen nucleophiles are applicable where Z is —$NR^H$—.

This being said, it is currently believed that particularly interesting nucleophile are those selected from $^-N_3$, $^-NR^HR^{H*}$, $^-SR^H$, $^{--}S$, $^-NR^HC(O)R^{H*}$, and $^-SC(O)R^H$.

The conditions for the reaction of the compound of Formula I with a nucleophile is typically so that the temperature is 0-150° C., such as 20-100° C., the reaction time is typically 5 min to 24 hours, such as 2-8 hours, and the molar ratio of the nucleophile to the compound of the Formula I is typically in the range of 10:1 to 1:1, such as in the range of 5:1 to 1:1. The solvent used for the reaction is typically a polar aprotic solvent.

Examples of useful polar aprotic solvents for this reaction are tetrahydrofuran (THF), dimethylformamide (DMF), dimethylsulfoxide (DMSO), acetonitrile (AcCN), diethylether, etc.

After substitution of the group $R^2$ with the nucleophile, the (new) group in the C2' position (i.e. the nucleophile attached to the C2' position) is subjected to such conditions that ring-closure between the C2' and C4' positions is effected so as to yield the LNA analogue of the formula IV. The exact conditions for effecting ring closure will depend on the nucleophile used, or rather the (new) group in the C2' position.

The conditions for the ring-closure reaction is typically so that the temperature is 0-100° C., such as 20-50° C., and the reaction time is typically 5 min to 24 hours, such as 2-8 hours. The solvent used for the reaction is typically a polar solvents. Examples of such polar solvents are DMF, THF, acetonitrile, DMSO, $C_{1-4}$-alcohols and aqueous mixtures thereof.

The reagent useful for facilitating the ring-closure is typically under basic conditions using bases such as hydroxides, alkoxides, amines, deprotonated amines, etc.

In particular, in the embodiments where Z is —S—, $Na_2S$ (of the type S$^{--}$) is a useful nucleophile that facilitates both substition and ringclosure (see preparation of 54). The temperature is typically 0-100° C., such as 15-40° C., the reaction time is typically 5 min to 18 hours, such as 10 min to 4 hours, and the molar ratio of the nucleophile to the compound of the Formula I is typically in the range of 10:1 to 1:1, such as in the range of 2:1 to 1:1. The polar aprotic solvent is typically DMF, THF, DMSO, acetonitrile, pyridine, N-methyl pyrrolidone (NMP), hexamethylphosphoramide (HMPA), etc.

In an other embodiment potassium thioacetate (of the $^-$SC(O)$R^H$ type) is a useful nucleophile. In this instance, the ring-closure can be effected under the influence of lithium hydroxide in a polar aprotic solvent (see preparation of 60). The temperature is typically 0-100° C., such as 15-40° C., the reaction time is typically 5 min to 18 hours, such as 5 min to 2 hours, and the molar ratio of the nucleophile to the compound of the Formula I is typically in the range of 10:1 to 1:1, such as in the range of 3:1 to 1:1. The polar aprotic solvent is typically DMF, THF, DMSO, acetonitrile, pyridine, N-methylpyrrolidone (NMP), hexamethylphosphoramide (HMPA), etc.

In the embodiment where Z is —NH—, sodium azide is a useful nucleophile. In this instance, the ring-closure is effected under the influence of sodium hydroxide and trimethyl-phosphane in a polar aprotic solvent. The temperature is typically 0-50° C., such as 15-30° C., the reaction time is typically 1-24 hours, such as 2-8 hours, and the molar ratio of the nucleophile to the compound of the Formula I is typically in the range of 10:1 to 1:1, such as in the range of 5:1 to 1:1. The polar aprotic solvent is typically DMF, THF, DMSO, acetonitrile, pyridine, N-methylpyrrolidone (NMP), hexannethylphosphoramide (HMPA), etc.

Figure 7:
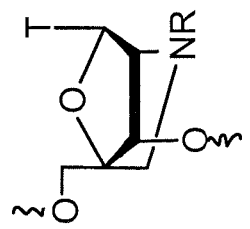
FIG. 7 illustrates further acylation and alkylation of the 2'-amino group of amino-LNA
Figure 8:
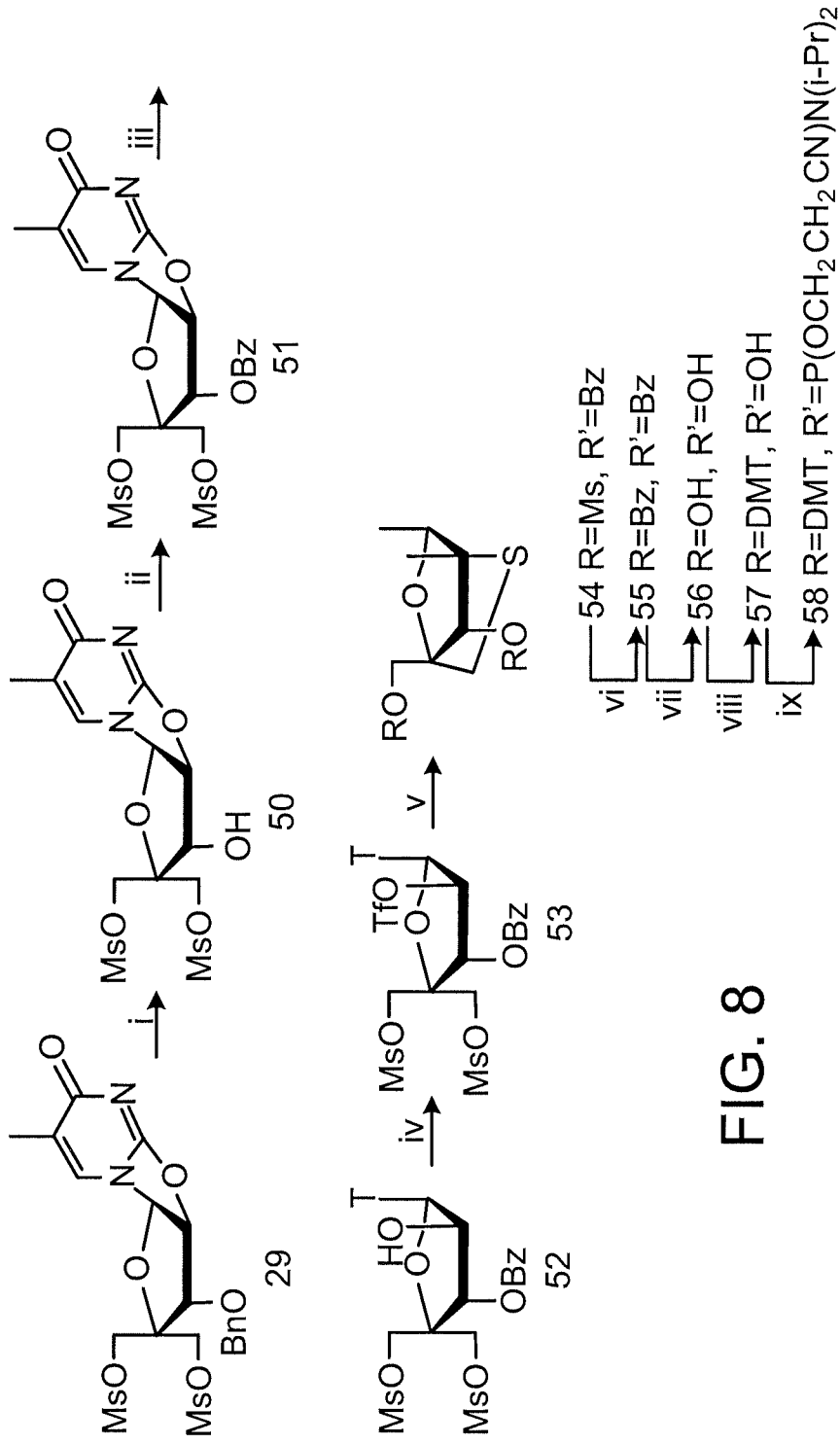
FIG. 8 illustrates a preferred example for the preparation of a thio-LNA phosphoramidite that is useful in the preparation of oligonucleotides. Legend: i) Pd/C, $H_2$, Acetone, MeOH; ii) BzCl, Pyridine, DMF; iii) 0.25 M aq. $H_2SO_4$, DMF, 80° C.; iv) $Tf_2O$, DMAP, $CH_2Cl_2$, 0° C.; v) $Na_2S$, DMF; vi) NaOBz, DMF, 100° C.; vii) $NH_3$, MeOH; viii) DMT-Cl, Pyridine; ix) $P(OCH_2CH_2CN)(N(i-Pr)_2)_2$, 4,5-Dicyanoimidazole, $CH_2Cl_2$.

When the resulting LNA analogues is one where Z is —NH—, the inventors have found that it is possible to convert the LNA analogues into another LNA analogue where the nitrogen is alkylated by reaction with an alkanal. Thus, the method may in this instance (Z=—NH—) further comprises the step of converting the LNA analogue wherein Z is —NH— to an LNA analogues where Z is —N($C_{1-6}$-alkyl)- or N(aryl) by reacting a solution of the former LNA analogue with a reducing agent and a $C_{1-6}$-alkanal or an aromatic aldehyde or where Z is N(acyl) by reacting with an acid chloride or an acid anhydride. Preferably where the aldehyd is formaldehyde, benzaldehyde, pyrene-1-carbaldehyde, or phthalimidoacetaldehyde and the reducing agent is NaBCNH$_3$, or wherein the acid chloride is benzoyl chloride or pyren-1-ylcarbonyl chloride (see FIG. 7). The method of the invention relates not only to the compounds of Formula IV but equally to amino-LNA analogues in general.

Amino-LNA analogues are particularly interesting compounds of the invention. For example, 9-mers oligonucleotides mixed sequence containing two or three of the novel modified 2'-amino-LNA monomers 45-49 (see FIG. 7) hybridize efficiently and in general with very high thermal stabilities comparable with those obtained for the LNA or N-methyl 2'-amino-LNA references ($\Delta T_m$/° C. in a thermal denaturation assay towards complementary RNA compound calculated per monomer: 45=+9.1, 46=+7.3, 47=+6.5, 48=+3 and 49=+7). Also, a (almost) fully modified N-benzoyl 2'-amino-LNA 9-mers oligonucleotides shows remarkably efficient binding towards DNA and RNA complements ($T_m$/° C. 75 and 73, $\Delta T_m$/° C. +6.3 and +6.1).

The triflate for Formula III is particularly useful as an intermediate for a wide range of LNA analogues by reaction with appropriate nucleophiles. As an example, the triflate 31 (see FIG. 9) is used in the synthesis of thio-LNA (2-oxo-5-thiobicyclo[2.2.1]heptane skeleton) accomplished by a substitution reaction with the nucleophile potassium thioacetate in DMF producing compound 59. Ring-closure of the thio-LNA nucleoside was achieved by hydrolysis of the thioacetate with aq. LiOH in THF to produce 60 in quantitative yield. The structure of 60 was confirmed by NOE experiments showing an unusually high NOE effect between H6 of the nucleobase and H3' (9.0%) as expected due to the extreme north conformation adopted by the nucleoside. Similarly, reaction of the triflate 31 with the nucleophile sodium azide in DMF produced compound 32 which was subsequently ring-closed to the amino-LNA nucleoside 33 under the influence of aqueous sodium hydroxide and trimethylphosphane in THF.

Figure 10:
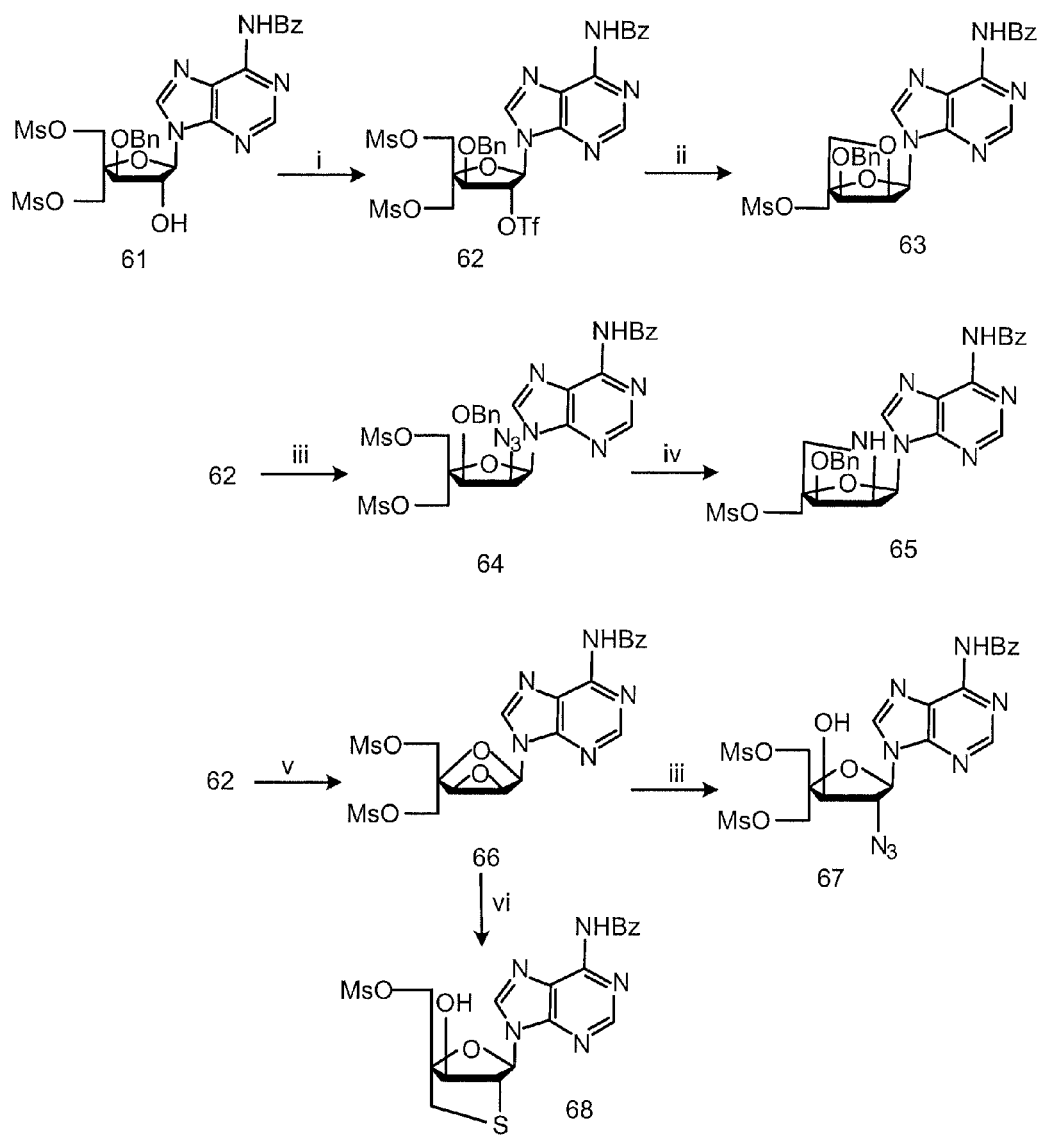
FIG. 10 illustrates the synthesis of the α-L-oxy-LNA A (63), α-L-amino-LNA A (65), as well as the synthesis of an epoxide (66) from the key intermediate 62, which is opened up with different nucleophiles to form either an azide (67) or a thio-LNA (68). Legend: i) $Tf_2O$, pyridine, DCM, ii) LiOH, aq, THF, iii) $NaN_3$, DMF, iv) NaOH, $PMe_3$, THF, v) MsOH, DCM, vi) $Na_2S$, DMF.
Figure 11:
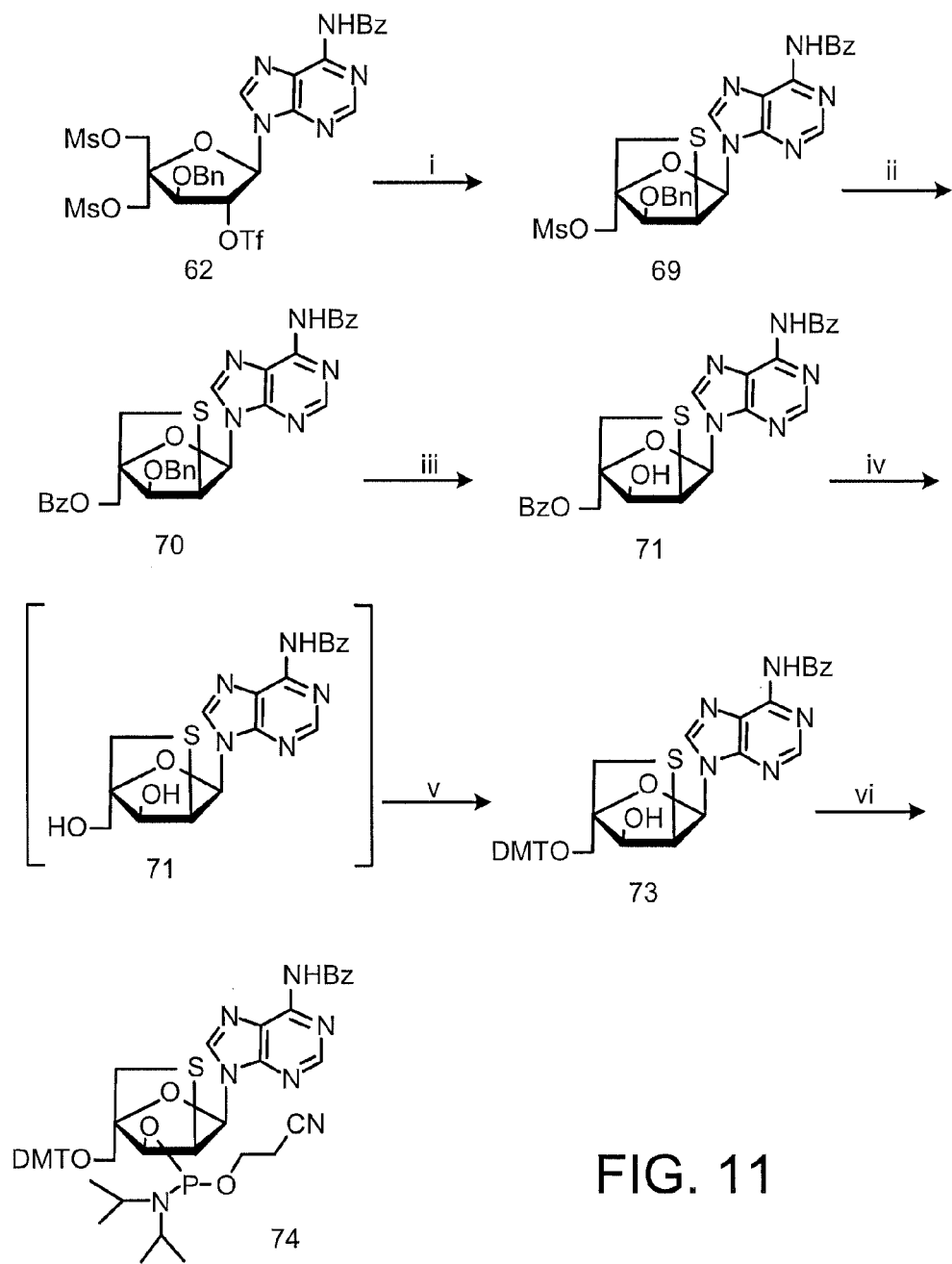
FIG. 11 illustrates a preferred example for the preparation of an α-L-thio-LNA phosphoramidite that is useful in the preparation of oligonucleotides. Legend: i) $Na_2S$, DMF, ii) NaOBz, DMSO, 100° C., iii) MsOH, DCM, iv) LiOH, aq, THF, v) DMT-Cl, DMAP, Pyridine vi) $P(OCH_2CH_2CN)$—$(N(i-Pr)_2)_2$, 4,5-Dicyanoimidazole, $CH_2Cl_2$.
Figure 12:
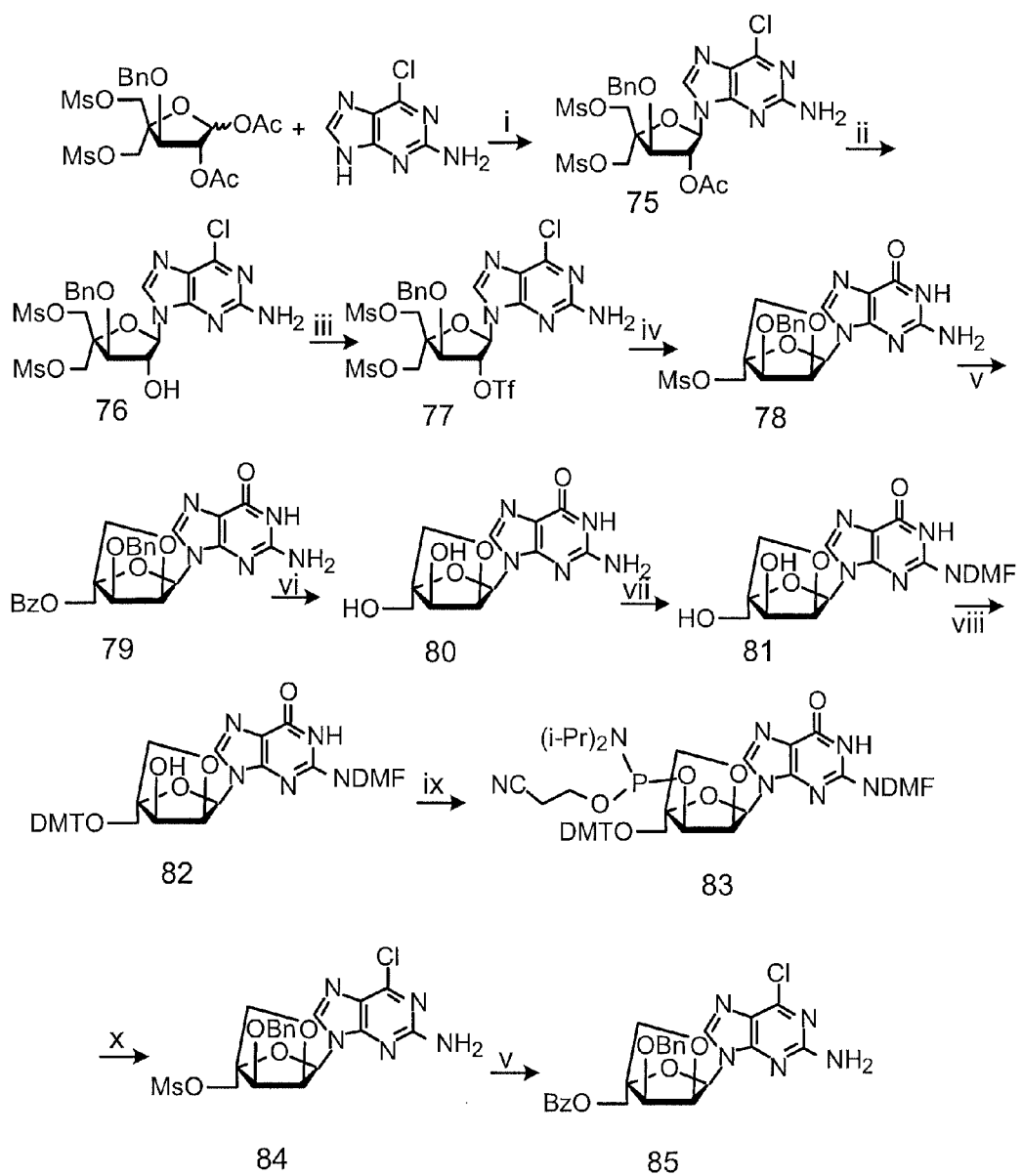
FIG. 12 illustrates a preferred example for the preparation of an α-L-LNA-G phosphoramidite that is useful in the preparation of oligonucleotides. Legend: i) BSA, TMSOTf, $ClCH_2CH_2Cl$, ii) half sat. methanolic $NH_3$, iii) $Tf_2O$, DMAP, pyridine, $CH_2Cl_2$, iv) $HOCH_2CH_2CN$, NaH, THF; v) NaOBz, DMSO; vi) $NH_4HCO_2$, $Pd(OH)_2$—C, MeOH; vii) $(CH_3O)_2CHN(CH_3)_2$, DMF; viii) DMT-Cl, pyridine, ix) $NC(CH_2)_2OP(N(iPr)_2)_2$, 4,5-dicyanoimidazole, MeCN, $CH_2Cl_2$, x) LION, aq, THF.

In one particularly interesting embodiment of intermediates of formula I, $R^3$ and $R^2$ together form an epoxide. Within the embodiment wherein formula I is such that $R^3$ and $R^2$ together form an epoxide, $A^4$ and $A^5$ independently are selected from $C_{1-6}$-alkylene; and $R^5$ is $C_{1-6}$-alkylsulfonyloxy optionally substituted with one or more substituents selected from halogen and phenyl optionally substituted with one or more substituents selected from nitro, halogen and $C_{1-6}$-alkyl, and arylsulfonyloxy optionally substituted with one or more substituents selected from nitro, halogen, $C_{1-6}$-alkyl, and $C_{1-6}$-alkyl substituted with one or more halogen; such as compound 66 in FIG. 10.

Synthesis of α-L-LNA analogues

The present invention may also be a method for the synthesis an α-L-LNA analogue e.g. α-L-oxy-LNA, α-L-thio-LNA or α-L-amino-LNA of the general formula VIII

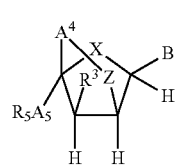

Formula VIII wherein

X is selected from —CH$_2$—, —NR$^H$—, —O—, and —S—;

Z is selected from —CH$_2$—, —NR$^H$—, —O—, —S—, and —Se—;

B is a nucleobase;

R$^3$ is selected from —R$^H$, —N$_3$, —NR$^H$R$^{H*}$, —NR$^H$C(O)R$^{H*}$, —C(O)NR$^H$R$^{H*}$, —OR$^H$, —OC(O)R$^H$, —C(O)OR$^H$, —SR$^H$, —SC(O)R$^N$, and tri(C$_{1-6}$-alkyliaryl)silyloxy;

each R$^H$ and R$^{H*}$ independently being selected from hydrogen, optionally substituted C$_{1-6}$-alkyl, optionally substituted aryl, and optionally substituted aryl-C$_{1-6}$-alkyl;

A$^4$ and A$^s$ independently are selected from C$_{1-6}$-alkylene; and

R$^5$ is selected from iodo, bromo, chloro, C$_{1-5}$-alkylsulfonyloxy optionally substituted with one or more substituents selected from halogen and phenyl optionally substituted with one or more substituents selected from nitro, halogen and C$_{1-6}$-alkyl, and arylsulfonyloxy optionally substituted with one or more substituents selected from nitro, halogen, C$_{1-6}$-alkyl, and C$_{1-6}$-alkyl substituted with one or more halogen;

said method comprising the following steps:

treating an intermediate of the general formula IX:

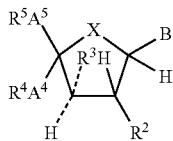

Formula IX wherein

X, B, R$^3$, A$^4$, and A$^5$ are as defined above;

R$^2$ is selected from iodo, C$_{1-6}$-alkylsulfonyloxy optionally substituted with one or more substituents selected from halogen and phenyl optionally substituted with one or more substituents selected from nitro, halogen and C$_{1-6}$-alkyl, and arylsulfonyloxy optionally substituted with one or more substituents selected from nitro, halogen, C$_{1-6}$-alkyl, and C$_{1-6}$-alkyl substituted with one or more halogen;

R$^3$ and R$^2$ may together form an epoxide; and

R$^4$ and R$^5$ independently are as defined for R$^5$ above, or R$^4$ and R$^5$ together constitutes a tetra(C$_{1-6}$-alkyl)disiloxanylidene group;

with a nucleophile selected from halogen, $^-$N$_3$, $^-$NR$^H$R$^{H*}$, $^-$OR$^H$, $^-$OH, $^-$SR$^H$, $^-$$^-$S, $^-$SeR$^H$, $^-$$^-$Se, $^-$NR$^H$C(O)R$^{H*}$, $^-$SC(O)R$^H$, and organometallic hydrocarbyl radicals, so as to substitute R$^2$, and effecting ring-closure between the C2' and C4' positions so as to yield the LNA analogue of the formula VIII.

The interesting embodiment of intermediates of formula I wherein R$^2$ and R$^3$ together forming an epoxide is particularly interesting in the synthesis of α-L-oxy-LNA, α-L-thio-LNA or α-L-amino-LNA using a compound of Formula IX, discussed infra.

In a further particularly interesting embodiment, the intermediate of formula IX has the formula X

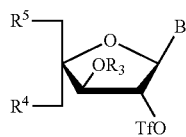

Formula X wherein B, R$^3$, R$^4$ and R$^5$ are as defined above.

The intermediate of Formula IX is reacted with a nucleophile selected from halogen, $^-$N$_3$, $^-$NR$^H$R$^{H*}$, $^-$OR$^H$, $^-$OH, $^-$SR$^H$, $^-$$^-$S, $^-$NR$^H$C(O)R$^{H*}$, $^-$SC(O)R$^H$, and organometallic hydrocarbyl radicals, so as to substitute R$^2$.

One particular advantage of using the common intermediate, X, in this invention in the reaction with hydroxide or an alkoxide such as 3-hydroxylpropionitrile alkoxide as the nucleophile is that the α-L-structure is made in one-pot. Thus, substitution of the triflate by hydroxide or 3-hydroxylpropionitrile alkoxide produces an alcohol that is immediately cyclised.

Embodiments relating to the synthesis of LNA analogues described supra are also applicable to the synthesis of α-L-LNA analogues.

The Novel Intermediates

It is believed that the majority of the intermediates (compounds of Formula I) represent novel compounds, thus the present invention also provides compounds of the formula I

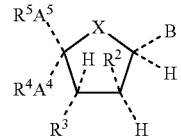

Formula I wherein

X is selected from —CH$_2$—, —NR$^H$—, —O—, and —S—;

B is a nucleobase;

R$^2$ is selected from iodo, C$_{1-6}$-alkylsulfonyloxy optionally substituted with one or more substituents selected from halogen and phenyl optionally substituted with one or more substituents selected from nitro, halogen and C$_{1-6}$-alkyl, and arylsulfonyloxy optionally substituted with one or more substituents selected from nitro, halogen, C$_{1-6}$-alkyl, and C$_{1-6}$-alkyl substituted with one or more halogen;

R$^3$ is selected from —R$^H$, —N$_3$, —NR$^H$R$^{H*}$, —NR$^H$C(O)R$^{H*}$, —C(O)NR$^H$R$^{H*}$, —OR$^H$, —OC(O)R$^H$, —C(O)OR$^H$, —SR$^H$, —SC(O)R$^H$, and tri(C$_{1-6}$-alkyliaryl)silyloxy;

R$^3$ and R$^2$ may together form an epoxide;

each R$^H$ and R$^{H*}$ independently being selected from hydrogen, optionally substituted C$_{1-6}$-alkyl, optionally substituted aryl, and optionally substituted aryl-C$_{1-6}$-alkyl;

A$^4$ and A$^5$ independently are selected from C$_{1-5}$-alkylene; and

R$^4$ and R$^5$ independently are selected from iodo, bromo, chloro, C$_{1-6}$-alkylsulfonyloxy optionally substituted with one or more substituents selected from halogen and phenyl optionally substituted with one or more substituents selected from nitro, halogen and C$_{1-6}$-alkyl, and arylsulfonyloxy optionally substituted with one or more substituents selected from nitro, halogen, C$_{1-6}$-alkyl, and C$_{1-5}$-alkyl substituted with one or more halogen, or R$^4$ and R$^5$ together constitutes a tetra(C$_{1-6}$-alkyl)disiloxanylidene group;

with the proviso that the compound is not selected from 1-(3-azido-3-deoxy-2,5-di-O-methanesulfonyl-4-C-(methansulfonyloxymethyl)-β-D-erythro-pentofuranosyl)thymine, 1-(3-O-benzyl-2,5-di-O-methanesulfonyl-4-C-(methansulfonyloxymethyl)-β-D-erythro-pentofuranosyl)thymine, and 1-(3-O-benzyl-2,5-di-O-methanesulfonyl-4-C-(nnethansulfonyloxymethyl)-α-L-threo-pentofuranosyl)thymine.

Particular and preferred subgroups of the compounds of formula I are as described above for the compound I under Synthesis of LNA analogues. In particular, particular subclasses of compounds have the formula II, in particular and the formula III.

Figure 13:
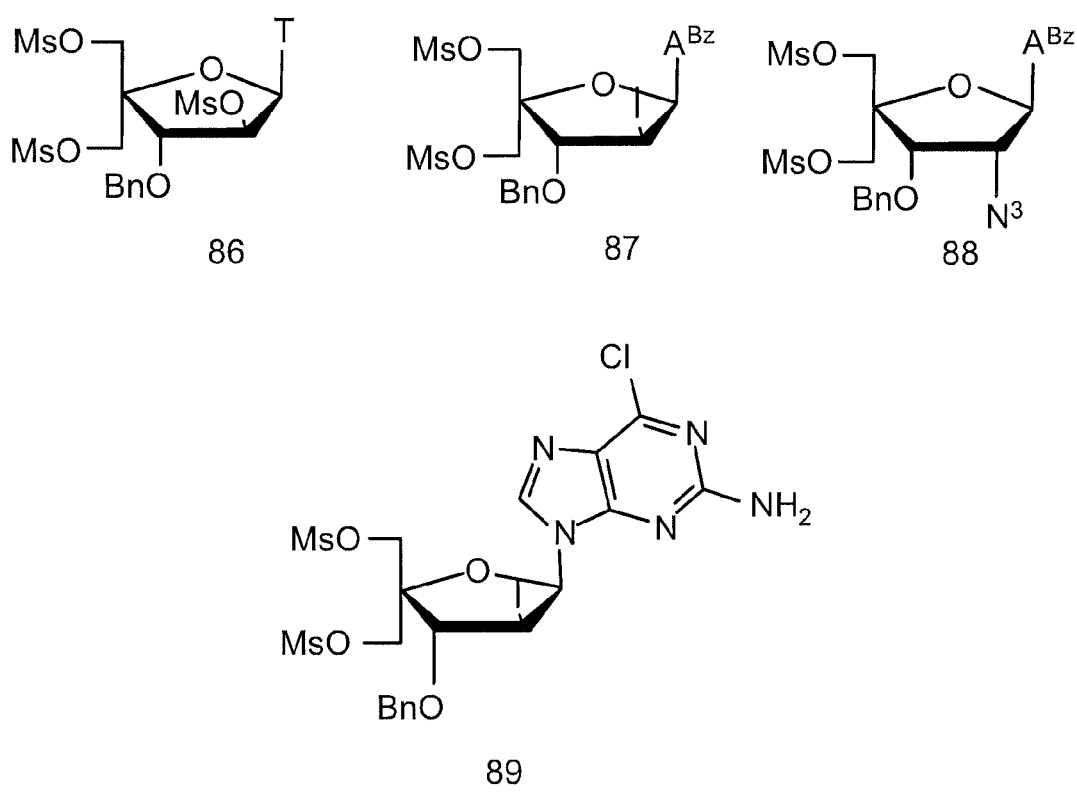
FIG. 13 illustrates particularly interesting compounds according to the invention.

Examples of particularly interesting specific compounds are those illustrated in FIG. 13.

Figure 9:
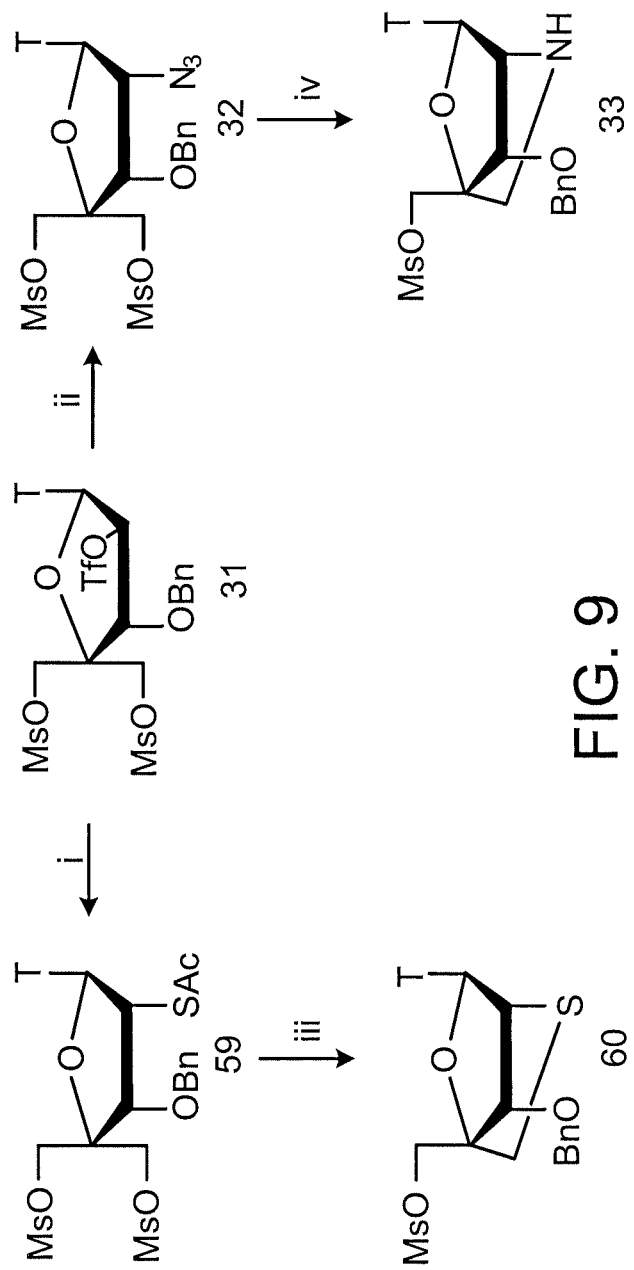
FIG. 9 illustrates the synthesis of an amino-LNA analogue 33 and a thio-LNA analogue 60 from the key intermediate 31 (a preferred example of a compound of Formula I). Legend: i) potassium thioacetate, DMF, ii) sodium azide in DMF, iii) LiOH in THF, iv) NaOH (aq.), $Me_3P$, THF.

It is presently believed that a particularly interesting compound which is particularly useful for the preparation of (1R,3R,4R,7S)-7-Benzyloxy-1-methansulfonyloxymethyl-3-(thymin-1-yl)-2-oxa-5-azabicyclo[2:2:1]heptane (33) and (1R,3R,4R,7S)-7-Benzyloxy-1-methansulfonyloxymethyl-3-(thymin-1-yl)-2-oxa-5-thiabicyclo[2:2:1]heptane (60) is 1-(3-O-Benzyl-5-O-methanesulfonyl-4-C-methanesulfonyloxymethyl-2-O-trifluoromethanesulfonyl-β-D-threo-pentofuranosyl)thymine (31) (see FIG. 9).

Particular and preferred subgroups of the compounds of formula I are described above under Synthesis of α-L-LNA analogues. In particular, a particular subclass of compounds has the formula IX and particularly formula X, and wherein $R^2$ and $R^3$ together form an epoxide.

Preparation of the Novel Intermediates

The compounds (intermediates) of the formula I can be prepared by inversion of the orientation of the C2' substituent in a similar compound in which the C2' substituent is a leaving group. Thus, the present invention also relates to a method for the synthesis of a compound of the formula I

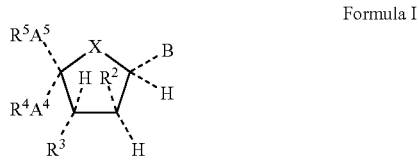

Formula I wherein
X is selected from —$CH_2$—, —$NR^H$—, —O—, and —S—;
B is a nucleobase;
$R^2$ is selected from iodo, $C_{1-5}$-alkylsulfonyloxy optionally substituted with one or more substituents selected from halogen and phenyl optionally substituted with one or more substituents selected from nitro, halogen and $C_{1-5}$-alkyl, and arylsulfonyloxy optionally substituted with one or more substituents selected from nitro, halogen, $C_{1-6}$-alkyl, and $C_{1-6}$-alkyl substituted with one or more halogen;
$R^3$ is selected from —$R^H$, —$N_3$, —$NR^HR^{H*}$, —$NR^HC(O)R^{H*}$, —$C(O)NR^HR^{H*}$, —$OR^H$, —$OC(O)R^H$, —$C(O)OR^H$, —$SR^H$, —$SC(O)R^N$, and tri($C_{1-6}$-alkyliaryl)silyloxy;
each $R^H$ and $R^{H*}$ independently being selected from hydrogen, optionally substituted $C_{1-6}$-alkyl, optionally substituted aryl, and optionally substituted aryl-$C_{1-5}$-alkyl;
$A^4$ and $A^5$ independently are selected from $C_{1-6}$-alkylene; $R^3$ and $R^2$ may together form an epoxide and $R^4$ and $R^5$ independently are selected from iodo, bromo, chloro, $C_{1-6}$-alkylsulfonyloxy optionally substituted with one or more substituents selected from halogen and phenyl optionally substituted with one or more substituents selected from nitro, halogen and $C_{1-6}$-alkyl, and arylsulfonyloxy optionally substituted with one or more substituents selected from nitro, halogen, $C_{1-6}$-alkyl, and $C_{1-6}$-alkyl substituted with one or more halogen.

said method comprising inversion of orientation of the substituent in the C2' position of a compound of the formula VII

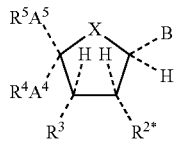

Formula VII wherein
$R^{2*}$ is a leaving group selected from iodo, $C_{1-6}$-alkylsulfonyloxy optionally substituted with one or more substituents selected from halogen and phenyl optionally substituted with one or more substituents selected from nitro, halogen and $C_{1-6}$-alkyl, and arylsulfonyloxy optionally substituted with one or more substituents selected from nitro, halogen, $C_{1-6}$-alkyl, and $C_{1-6}$-alkyl substituted with one or more halogen; and
X, B, $R^3$, $R^4$, $A^4$, $R^5$ and $A^5$ are as defined above.

Particular examples of $R^{2*}$ groups are iodo, methanesulfonyloxy, trifluoromethanesulfonyl-oxy, ethanesulfonyloxy, 2,2,2-trifluoroethanesulfonyloxy, propanesulfonyloxy, isopropanesulfonyloxy, butanesulfonyloxy, nonafluorobutanesulfonyloxy, pentanesulfonyloxy, cyclopentanesulfonyloxy, hexanesulfonyloxy, cyclohexanesulfonyloxy, α-toluenesulfonyl-oxy, 2-chloro-α-toluenesulfonyloxy, ortho-toluenesulfonyloxy, meta-toluenesulfonyloxy, para-toluenesulfonyloxy, benzenesulfonyloxy, ortho-bromobenzenesulfonyloxy, meta-bromobenzenesulfonyloxy, para-bromobenzenesulfonyloxy, ortho-nitrobenzenesulfonyloxy, meta-nitrobenzenesulfonyloxy, and para-nitrobenzenesulfonyloxy, of which trifluoro-methylsulfonyloxy is a particularly preferred example.

Particular and preferred subgroups of the compounds of formula VII corresponds to those described above for the compound I under Synthesis of LNA analogues, mutatis mutandis. In particular, particular subclasses of compounds have the configuration corresponding to formula II, especially the configuration corresponding to formula III, except for the orientation of the substituent on C2'.

In a particularly interesting embodiment of compounds of formula I, $R^3$ and $R^2$ together form an epoxide.

Figure 2:
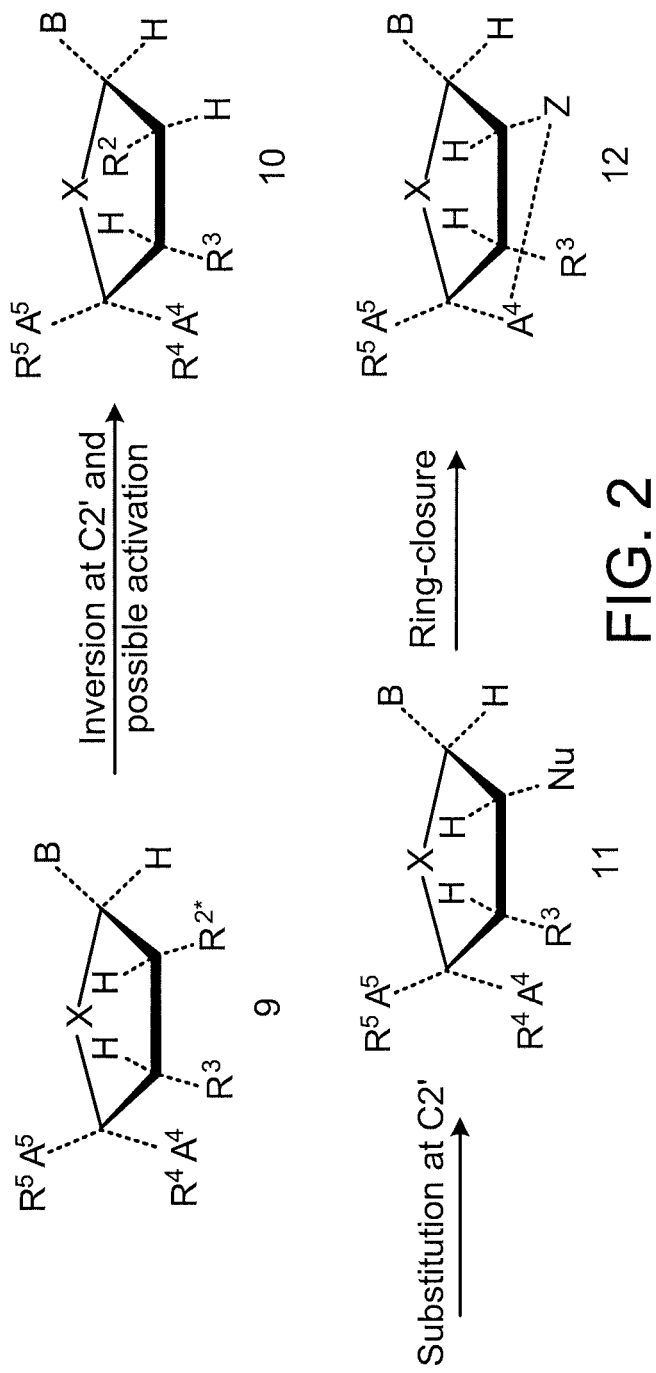
FIG. 2 illustrates the generalised method for the preparation of the LNA analogues.

The novel compound illustrated in Formula I can be prepared by the general route shown in FIG. 2.

The inversion of the orientation of the substituent on C2' can effect in various ways. If the nucleobase is a pyrimidine base, the inversion can be facilitated by formation of a 2,2'-anhydro intermediate under suitable conditions, e.g. use of a proton sponge e.g. DBU. The temperature is typically 0-100° C., such as 15-30° C., the reaction time is typically 5 min to 24 hours, such as 1-6 hours, and the molar ratio of the base to the compound of the Formula VII is typically in the range of 5:1 to 1:1, such as in the range of 3:1 to 1:1. The polar aprotic solvent is typically DMF, THF, DMSO, or $CH_3CN$.

Although the above-mentioned method for the synthesis of the compound of Formula I takes advantage of the 2,2'-anhydronucleoside construct, and therefore only is applicable for nucleobases (such as pyrimidines) in which such a construct is possible, it should be understood that other routes will be similarly applicable for the inversion of orientation of the substituent in the C2' position of a compound of the formula VII.

As an example, which is generally applicable for all nucleobases, and very useful in the instances where the nucleobase is a purine type nucleobase, the inversion is effected by reaction of the compound of the formula VII with an oxygen nucleophile.

Figure 3:
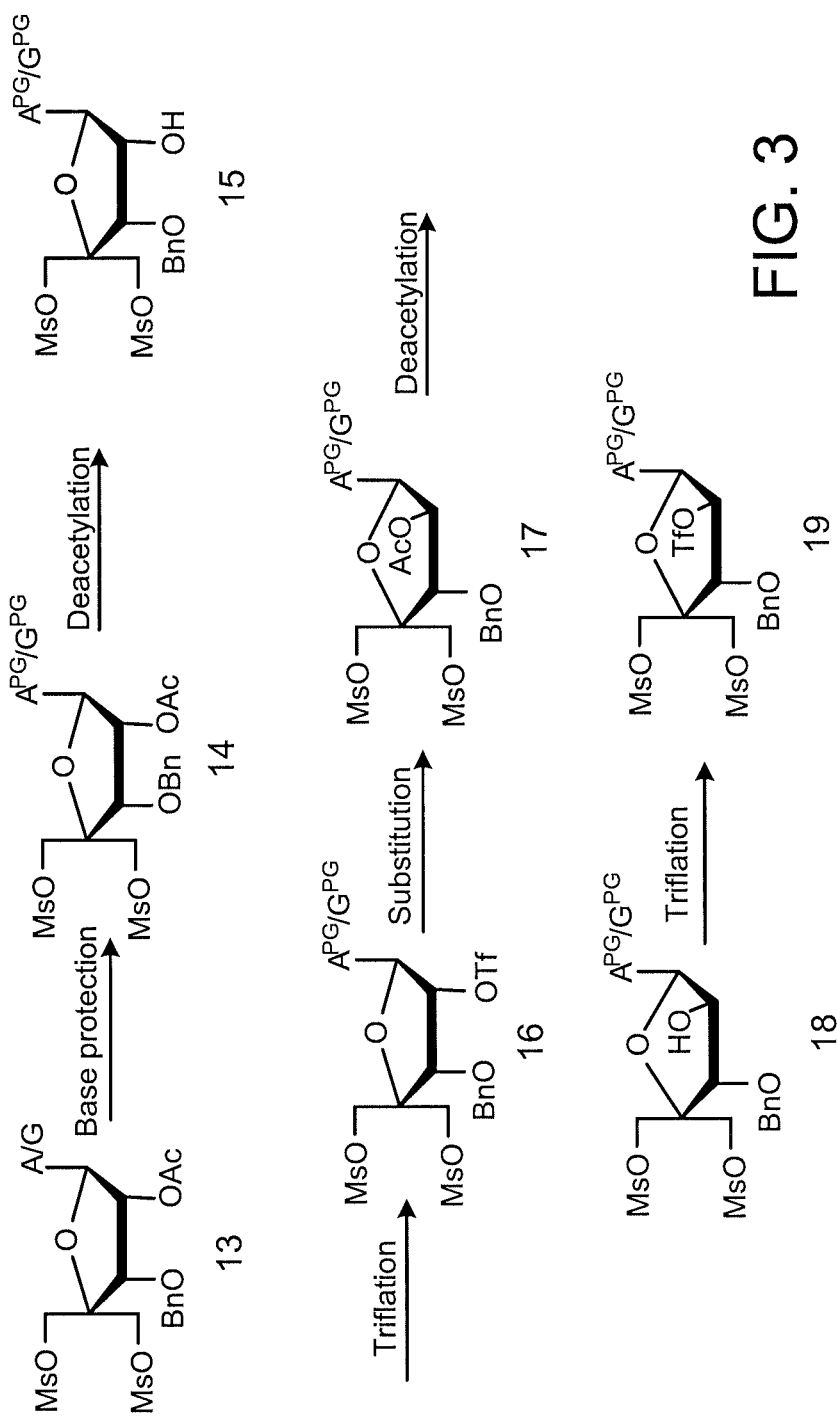
FIG. 3 illustrates inversion at C2' for a compound not having a pyrimidine base.
Figure 6:
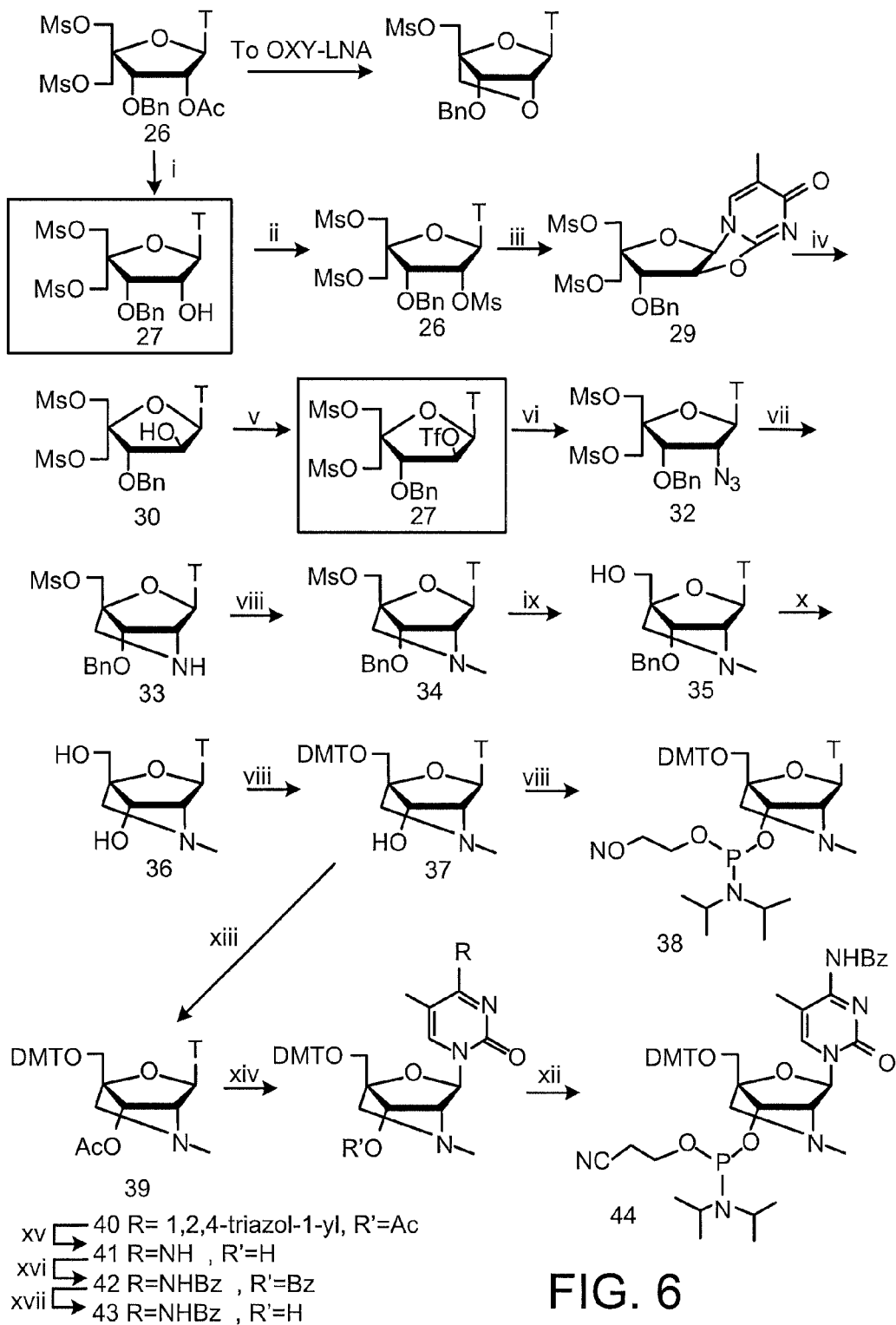
FIG. 6 illustrates a preferred example for the preparation of two amino-LNA phosphoramidite that are useful in the preparation of oligonucleotides. Legend: i) half sat. $NH_3$ in MeOH; ii) MsCl, anh. pyridine, anh. $CH_2Cl_2$; iii) DBU, DMF; iv) acetone, 0.1M $H_2SO_4$; v) $Tf_2O$, DMAP, anh. pyridine, anh. $CH_2Cl_2$; vi) $NaN_3$, anh. DMF; vii) $PMe_3$, NaOH (aq), THF; viii) $CH_2O$, $HCO_2H$; ix) a) NaOBz, DMF, b) NaOMe; x) 20% $Pd(OH)_2/C$, $H_2$, AcOH; xi) DMT-Cl, anh. pyridine; xii) $NC(CH_2)_2OP(N(iPr)_2)_2$, DCl, $CH_3CN$, $CH_2Cl_2$. xiii) $Ac_2O$, pyridine; xiv) $Et_3N$, 1,2,4-triazole, $POCl_3$, MeCN; xv) 1:1 MeCN, sat. aq $NH_3$; xvi) BzCl, pyridine; xvii) LiOH (aq), THF.

A more specific example of the convergent synthesis strategy for the synthesis of an intermediate having a purine-type nucleobase is illustrated in FIG. 3. Compound 13 is base protected (14) after which the 2'-OAc is hydrolysed selective as described elsewhere herein (15). The liberated 2'-OH is triflated (16) and reacted with a suitable oxygen nucleophile (e.g. an acetate, benzoate, etc.) to invert the stereochemistry (17). The resulting ester is then selective hydrolysed as described elsewhere herein and the 2'-OH now in the threo configuration (18). Compound 18 is a purine equivalent to compound 30 which can subsequently be converted to 2'-O-mesylate, i.e. an intermediate of the formula I, following the route illustrated in FIG. 6.

Figure 4:
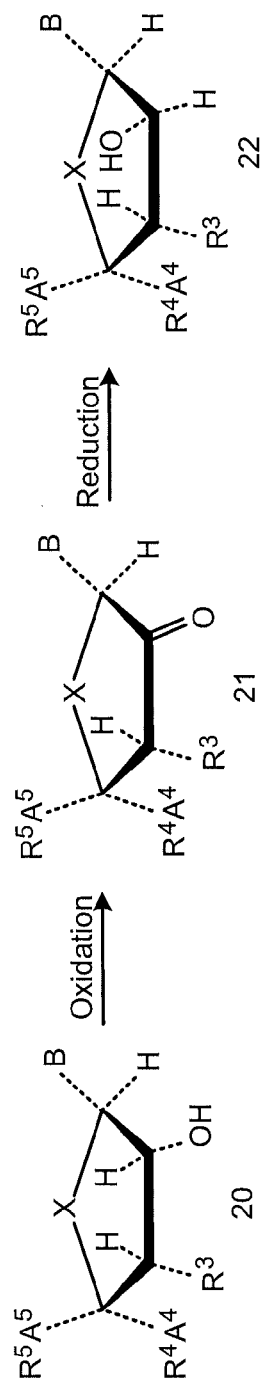
FIG. 4 illustrates a further alternative for inversion at C2'.

As a further alternative, inversion can also be effected by oxidation of a compound of Formula VII where $R^{2*}$ is OH, followed by subsequent stereo- and regioselective reduction, e.g. as outlined in FIG. 4.

The starting materials of Formula VII for the method according to the invention may be prepared as described in the literature (Koshkin, A.; Fensholdt, J.; Pfundheller, H. M.; Lomholt, C. *J. Org. Chem.* 2001. 66, 8504-8512).

Figure 5:
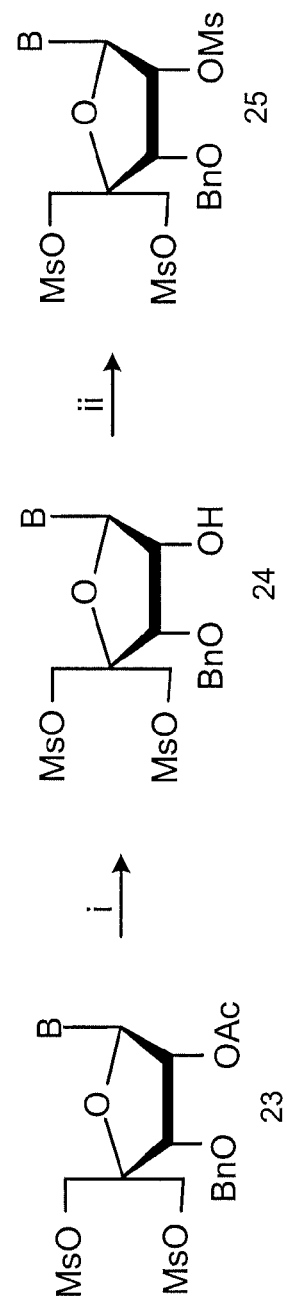
FIG. 5 illustrates the synthesis of a preferred compound of the formula VII. The known compound 1-(2-O-acetyl-3-O-benzyl-4-C-methanesulfonyloxymethyl-5-O-methane-sulfonyl-β-D-erythro-pentofuranosyl) thymine (23) is converted by a mild deacetylation for the liberation of the 2'-hydroxy group to the compound (24) without the subsequent ring-closure that affords the oxy-LNA skeleton. The 2'-hydroxy group is then mesylated to 1-(3-O-benzyl-4-C-methanesulfonyloxymethyl-2,5-O-dimethanesulfonyl-β-D-erVthro-pentofuranosyl) thymine (25). Legend: i) 50% methanolic ammonia; ii) MsCl, pyridine.

As a more specific example, the preferred general intermediate shown in formula III can be prepared as shown below (FIG. 5). Thus, (2-O-acetyl-3-O-benzyl-4-C-methanesulfonyloxymethyl-5-O-methanesulfonyl-β-D-erythro-pentofuranosyl)-nucleobase) (23) is converted by a mild deacetylation for the liberation of the 2'-hydroxy group to the compound (24) without the subsequent ringclosure that affords the oxy-LNA skeleton. The 2'-hydroxy group is then mesylated to afford (3-O-benzyl-4-C-methanesulfonyl-oxymethyl-2,5-O-dimethanesulfonyl-β-D-erythro-pentofuranosyl)-nucleobase) (25).

Thus, the present invention also relates to a method for the synthesis of a compound of the formula IX and X as described above under Synthesis of α-L-LNA analogues.

In view of the above, the present invention also provides method for the synthesis of an LNA analogue of the formula IV

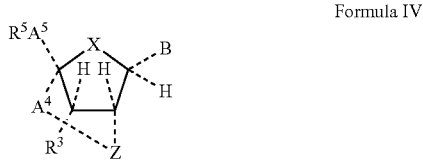

Formula IV said method comprising synthesis of a compound of the formula I from a compound of the formula VII as defined in the method above, and conversion of the compound of the formula I to an LNA analogues of the formula IV as defined further above.

Definitions

In the present context, the term "$C_{1-6}$-alkyl" means a linear, cyclic or branched hydrocarbon group having 1 to 6 carbon atoms, such as methyl, ethyl, propyl, iso-propyl, butyl, tert-butyl, iso-butyl, pentyl, cyclopentyl, hexyl, cyclohexyl, in particular methyl, ethyl, propyl, iso-propyl, tert-butyl, iso-butyl and cyclohexyl.

The term "$C_{1-6}$-alkylene" is intended to mean a linear hydrocarbon biradical having 1-6 carbon atoms, such as methylene, 1,2-ethylene, 1,3-propylene, 1,2-propylene, 1,4-butylene, etc.

The term "optionally substituted" in connection with the terms "$C_{1-6}$-alkyl" and "$C_{1-6}$-alkylene" is intended to mean that the group in question may be substituted one or several times, preferably 1-3 times, with group(s) selected from hydroxy $C_{1-6}$-alkoxy (i.e. $C_{1-6}$-alkyl-oxy), carboxy, $C_{1-6}$-alkoxycarbonyl, $C_{1-6}$-alkylcarbonyl, aryl, aryloxycarbonyl, aryloxy, arylcarbonyl, amino, mono- and di($C_{1-6}$-alkyl) amino; carbamoyl, mono- and di($C_{1-6}$-alkyl)-aminocarbonyl, $C_{1-6}$-alkylcarbonylamino, cyano, carbamido, halogen, where any aryl may be substituted as specifically describe below for "optionally substituted aryl".

In the present context the term "aryl" means a fully or partially aromatic carbocyclic ring or ring system, such as phenyl, naphthyl, 1,2,3,4-tetrahydronaphthyl, anthracyl, and phenanthracyl, among which phenyl is a preferred example.

The term "optionally substituted" in connection with the term "aryl" is intended to mean that the group in question may be substituted one or several times, in particular 1-3 times) with group(s) selected from hydroxy, $C_{1-6}$-alkoxy, carboxy, $C_{1-6}$-alkoxy-carbonyl, $C_{1-6}$-alkylcarbonyl, aryl, amino, mono- and di($C_{1-6}$-alkyl)amino, and halogen, wherein aryl may be substituted 1-3 times with $C_{1-4}$-alkyl, $C_{1-4}$-alkoxy, nitro, cyano, amino or halogen.

In the present context, the term "tri($C_{1-6}$-alkyl/aryl)silyloxy" means a silyl group substituted with 0-3 $C_{1-6}$-alkyl groups and/or 0-3 aryl groups, with the provision that the total number of alkyl and aryl groups is 3. Illustrative examples are trimethylsilyloxy, allyldimethylsilyloxy, dimethylphenylsilyloxy, diphenylmethylsilyloxy, isopropyldimethylsilyloxy, tert-butyldimethylsilyloxy, tert-butyldiphenylsilyloxy, triethylsilyloxy, triisopropylsilyloxy, diethylisopropylsilyloxy, dimethylthexyl-isopropylsilyloxy, tribenzylsilyloxy, tri-para-xylylsilyloxy, triphenylsilyloxy, diphenylmethylsilyloxy, di-tert-butylmethylsilyloxy, tris(trimethylsilyloxy)silyloxy, tert-butylmethoxyphenylsilyloxy, and tert-butoxydiphenylsilyloxy.

In the present context, the term "tetra($C_{1-6}$-alkyl)disiloxanylidene" means a —O—Si($C_{1-6}$-alkyl)$_2$-O— biradical. A typical example is 1,3-(1,1,3,3-tetraisopropyl)-disiloxanylidene.

"Halogen" includes fluoro, chloro, bromo, and iodo.

In the present context, the terms "nucleobase" covers naturally occurring nucleobases as well as non-naturally occurring nucleobases, i.e. heteroaromatic cyclic groups, e.g. monocyclic groups, bicyclic groups, tricyclic groups, etc. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$—$C^6$)-alkynylcytosine, 5-fluorouracil, 5-bromouracil, pseudoisocytosine, 2-hydroxy-5-methyl-4-triazolopyridin, isocytosine, isoguanin, inosine, $N^6$-allylpurines, $N^6$-acylpurines, $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^4$-alkylpyrimidines, $N^4$-acylpyrimidines, $N^4$-benzylpurine, $N^4$-halopyrimidines, $N^4$-vinylpyrimidines, $N^4$-acetylenic pyrimidines, $N^4$-acyl pyrimidines, $N^4$-hydroxyalkyl pyrimidines, $N^6$-thioalkyl pyrimidines, 6-azapyrimidine, including 6-azacytosine, 2- and/or 4-mercaptopyrimidine, uracil, $C^5$-alkylpyrimidines, $C^5$-benzylpyrimidines, C5-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimdine, $N^2$-alkylpurines, $N^2$-alkyl-6-thiopurines, 5-azacytidinyl, 5-azauracilyl, trazolopyridinyl, imidazolopyridinyl, pyrrolopyrimidinyl, and pyrazolopyrimidinyl. Functional oxygen and nitrogen groups on the base can be protected and deprotected if necessary or desirable. Suitable protecting groups are well known to those skilled in the art, and included trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl. Preferred bases include adenine, guanine, 2,6-diaminopurine, thymine, 2-thiothymine, cytosine, methyl cytosine, uracil, 5-fluorocytosine, xanthine, 6-aminopurine, 2-aminopurine, 6-chloro-2-amino-purine, and 6-chloropurine. Especially interesting nucleobases are adenine, guanine, thymine, cytosine, and uracil, which are considered as the naturally occurring nucleobases in relation to therapeutic and diagnostic application in humans.

EXAMPLES

For reactions conducted under anhydrous conditions glassware was dried overnight in an oven at 150° C. and was allowed to cool in a dessicator over anhydrous KOH. Anhydrous reactions were carried out under an atmosphere of argon. Solvents were HPLC grade, of which DMF, pyridine, acetonitrile and dichloromethane were dried over molecular sieves (4 Å from Grace Davison) and THF was freshly destilled from Na•benzophenone to a water content below 20 ppm. TLC was run on Merck silica 60 $F_{254}$ aluminum sheets. Dry Column Vacuum Chromatography (DCVC) was performed according to the published procedure. $^1H$, $^{13}C$, $^{19}F$, and $^{31}P$ NMR spectra were recorded at respectively 400 MHz, 100 MHz, 376 MHz, and 121 MHz with solvents as internal standard ($\delta_H$: CDCl$_3$ 7.26 ppm, DMSO-d$_6$ 2.50; $\delta_C$: CDCl$_3$ 77.0 ppm, DMSO-d$_6$ 39.4 ppm). $^{31}P$ NMR was run with 85% H$_3$PO$_4$ as external standard. J values are given in Hz. Assignments of NMR spectra are based on 2D spectra and follow the standard carbohydrate/nucleoside nomenclature (the carbon atom of the 4'-C-substituent is numbered C1") even though the systematic compound names of the bicyclic nucleoside derivatives are given according to the von Baeyer nomenclature. Crude compounds were used without further purification if they were ≧95% pure by TLC and HPLC-MS (RP C18 column, UV detection). Elemental analyses were obtained from the University of Copenhagen, Microanalytical Department.

1-(2,5-Di-O-acetyl-4-C-acetyloxymethyl-3-O-benzyl-β-D-erythro-pentofuranosyl)thymine To a stirred solution of 3-O-benzyl-4-C-hydroxymethyl-1,2-O-isopropylidene-α-D-erythro-pentofuranose 1 (Youssefyeh, R. D.; Verheyden, J. P. H.; Moffatt, J. G. *J. Org. Chem.* 1979, 44, 1301-1309). (200 mg, 0.64 mmol) in acetic acid (3.69 mL, 64.4 mmol) at 0° C. was added acetic anhydride (0.61 mL, 6.44 mmol) and concd H$_2$SO$_4$ (0.34 µL, 6.44 µmol). After 25 min the reaction mixture was allowed to warm to rt. Stirring was continued for 2 h after which the mixture was poured into ice cooled sat. aq NaHCO$_3$ (150 mL). The solution was extracted with dichloromethane (2×150 mL), and the combined organic phases were washed with sat. aq NaHCO$_3$ (2×100 mL), dried (Na$_2$SO$_4$), filtered and evaporated to dryness in vacuo to give the crude anomeric mixture of the acetylated glycoside donor as a colorless liquid (258 mg, 0.59 mmol). The liquid (246 mg, 0.56 mmol) was dissolved in anhyd acetonitrile (5 mL) with stirring. Thymine (144 mg, 1.14 mmol) and N,O-bis(trimethylsilyl)acetamide (0.99 mL, 4.00 mmol) were added, and the mixture was heated to reflux for 1.5 h and then cooled to 0° C. Trimethylsilyl triflate (0.23 mL, 1.25 mmol) was added dropwise during 5 min and the mixture was heated to 80° C. for 3.5 h. The reaction mixture was allowed to cool to rt, and ice cooled sat. aq NaHCO$_3$ (10 mL) was added. Extraction was performed with dichloromethane (2×20 mL), and the combined organic phases was washed successively with sat. aq NaHCO$_3$ (2×20 mL) and brine (20 mL), dried (Na$_2$SO$_4$), filtered and evaporated to dryness in vacuo. The residue was purified by DCVC (0-1% MeOH in dichloromethane v/v) to give the nucleoside (259 mg, 91%) as a white solid material. FAB-MS m/z found 505.0 ([MH]$^+$, calcd 505.2); $^1$H NMR (CDCl$_3$) δ9.93 (s, 1H, NH), 7.37-7.28 (m, 5H, Ph), 7.09 (d, J=0.9, 1H, H6), 5.79 (d, J=3.5, 1H, H1'), 5.53 (dd, J=6.3, 3.7, 1H, H2'), 4.64-4.08 (m, 7H, CH$_2$Ph, H3', H5'a, H5' b, H1"a, H1"b), 2.11 (s, 3H, CH$_3$C(O)), 2.10 (s, 3H, CH$_3$C(O)), 2.07 (s, 3H, CH$_3$C(O)), 1.91 (s, 3H, CH$_3$); $^{13}$C NMR (CDCl$_3$) δ 170.4, 169.9, 163.9, 149.9 (CH$_3$C(O), C2, C4), 137.1, 136.8, 128.3, 128.0, 127.8 (C6, Ph), 111.0 (C5), 90.6 (C1'), 84.2 (C4'), 77.0 (C3'), 74.2 (CH$_2$Ph), 73.7 (C2'), 63.6, 62.2 (C5', C1"), 20.6, 20.5 (CH$_3$C(O)), 12.3 (CH$_3$).

1-(3-O-Benzyl-4-C-hydroxymethyl-β-D-erythro-pentofuranosyl)thymine

Nucleoside 1-(2,5-Di-O-acetyl-4-C-acetyloxymethyl-3-O-benzyl-β-D-erythro-pentofuranosyl)thymine (149 mg, 0.30 mmol) was dissolved in a sat. solution of NH$_3$ in MeOH (15 mL). The mixture was stirred overnight at rt in a sealed flask and evaporated to dryness under reduced pressure. The residue was dissolved in EtOAc (30 mL) and washed with water (10 mL). The aq phase was extracted with EtOAc (30 mL) and the combined organic phases were coevaporated to dryness with acetonitrile (2×10 mL) under reduced pressure. The residue was purified by DCVC (1-4% MeOH in dichloromethane v/v), affording the nucleoside (93 mg, 84%) as a viscous liquid. R$_f$ 0.32 (10% MeOH in EtOAc, v/v); FAB-MS m/z found 379.0 ([MH]$^+$, calcd 379.1); $^1$H NMR (DMSO-d$_6$) δ 11.29 (br s, 1H, NH), 7.73 (d, J=1.3, 1H, H6), 7.40-7.26 (m, 5H, Ph), 5.90 (d, J=6.2, 1H, H1'), 5.51 (d, J=7.5, 1H, OH), 5.18 (t, J=5.0, 1H, OH), 4.86 (t, J=5.49, 1H, OH), 4.81 (d, 3=11.7, 1H), 4.56 (d, J=11.7, 1H), 4.36 (q, J=6.3, 1H, H2'), 4.08 (d, J=5.5, 1H, H3'), 3.60-3.50 (m, 4H) (H5', H1", CH$_2$Ph), 1.79 (d, J=1.1, 3H, CH$_3$); $^{13}$C NMR (DMSO-d$_6$) δ163.6 (C4), 150.7 (C2), 138.6, 136.3, 128.0, 127.2 (C6, Ph), 109.3 (C5), 87.7, 87.5 (C1', C4'), 78.5 (C3'), 73.3 (C2'), 72.7, 62.8, 61.3 (C5', C1", CH$_2$Ph), 12.2 (CH$_3$); Anal. calcd for C$_{18}$H$_{22}$N$_2$O$_7$.0.25 H$_2$O: C, 56.5; H, 5.9; N, 7.3. Found: C, 56.5; H, 5.9; N, 7.0.

1-(3-O-Benzyl-2,5-di-O-methanesulfonyl-4-C-(methanesulfonyloxymethyl)-β-D-erythro-pentofuranosyl)thymine (28)

Nucleoside 1-(3-O-Benzyl-4-C-hydroxymethyl-β-D-erythro-pentofuranosyl)thymine (0.83 g, 3.2 mmol) was dissolved in anhyd pyridine (20 mL) and cooled to 0° C. with stirring. Methanesulfonyl chloride (0.85 mL, 11 mmol) was added dropwise and the reaction was allowed to reach 15° C. over 3 h. The reaction was quenched with sat. aq NaHCO$_3$ (50 mL) and transferred to a separatory funnel with brine (50 mL) and EtOAc (100 mL). The phases were separated and the aq phase extracted with EtOAc (2×50 mL). The combined organic phases were extracted with brine (100 mL), dried (Na$_2$SO$_4$), filtered and evaporated in vacuo to give a viscous yellow liquid. The liquid was dissolved in a mixture of dichloromethane and toluene and evaporated in vacuo to give nucleoside 28 (1.48 g, 93%) as a white foam. Analytical data were identical to those previously published. (Håkansson, A. E.; Koshkin, A.; Sørensen, M. D.; Wengel, J. *J. Org. Chem.* 2000, 65, 5161-5166.)

1-(3-O-Benzyl-5-O-methanesulfonyl-4-C-methanesulfonyloxymethyl-β-D-erythro-pentofuranosyl)thymine (27)

Nucleoside 26 (Koshkin et al., J. Org. Chem. 2001, 66, 8504-8512) (30 g, 52 mmol) was dissolved in MeOH (600 mL), and the solution was cooled to 0° C. Freshly prepared sat. methanolic ammonia (600 mL) was added, and the mixture was allowed to reach rt. After 5 h at rt the reaction was quenched with glacial acetic acid (50 mL) and transferred to a beaker, where it was neutralised with sat. aq $NaHCO_3$. EtOAc (900 mL) and brine (500 mL) was added and the phases were separated. The aq phase was extracted with EtOAc (3×500 mL) and the combined organic phases were washed with sat. aq $NaHCO_3$ (500 mL) and brine (500 mL). The organic phase was dried ($Na_2SO_4$), filtered and the solvent removed in vacuo to afford 27 (27 g, 97%) as a white foam. $R_f$=0.33 (100% EtOAc); ESI-MS m/z found 557.0 ($[MNa]^+$. Calcd 557.1); $^1H$ NMR ($CDCl_3$) δ 10.21 (br s, 1H, NH), 7.33-7.25 (m, 6H, Ph, H6), 5.77 (d, J=3.9, 1H, H1'), 4.84 (d, J=11.4, 1H, H3'), 4.59-4.57 (m, 3H), 4.42-4.37 (m, 3H), 4.26-4.19 (m, 2H) (H2', H2", H5", $CH_2Ph$, OH), 2.98 (s, 3H, $CH_3$), 2.76 (s, 3H, $CH_3$), 1.80 (s, 3H, $CH_3$); $^{13}C$ NMR ($CDCl_3$) δ162.5 (C4), 151.0 (C2), 136.7 (Ph), 136.2 (C6), 128.5, 128.3, 128.2 (Ph), 111.3 (C5), 92.1 (C1'), 84.0 (C4'), 77.7 (C3'), 74.1, 73.5 (C2', $CH_2Ph$), 68.6, 68.3 (C5', C1"), 37.2, 37.1 (Ms), 12.0 ($CH_3$); Anal. calcd for $C_{20}H_{26}N_2O_{11}S_2$: C, 44.9; H, 4.9; N, 5.2. Found: C, 45.0; H, 4.7; N, 5.1.

1-(3-O-Benzyl-2,5-di-O-methanesulfonyl-4-C-(methanesulfonyloxymethyl)-β-D-erythro-pentofuranosyl)thymine (28)

Nucleoside 27 (20 g, 37 mmol) was dissolved in anhyd dichloromethane (100 mL) and anhyd pyridine (100 mL) was added. The solution was cooled to 0° C. and methanesulfonyl chloride (4.4 mL, 56 mmol) was added dropwise. After 2 h the reaction was quenched with sat. aq $NaHCO_3$ (200 mL), and the phases were separated. The aq phase was extracted with dichloromethane (2×150 mL), and the combined organic phases were washed with aq HCl (1 M, 2×200 mL), sat. aq $NaHCO_3$ (2×250 mL) and brine (250 mL). The organic phase was dried ($Na_2SO_4$), filtered and the solvent was removed in vacuo. The crude product was co-evaporated with toluene affording 28 (22 g, 96%) as a white foam. $R_f$=0.41 (100% EtOAc); ESI-MS m/z found 635.0 ($[MNa]^+$, calcd 635.1). All analytical data were identical to those previously reported. (Håkansson, A. E.; Koshkin, A.; Sørensen, M. D.; Wengel, J. *J. Org. Chem.* 2000, 65, 5161-5166)

2,2'-Anhydro-1-(3-O-benzyl-5-O-methanesulfonyl-4-C-methanesulfonyloxymethyl-β-D-threo-pentofuranosypthymine (29)

Nucleoside 28 (10 g, 16.3 mmol) was dissolved in anhyd acetonitrile (100 mL) and DBU (2.69 mL, 18.0 mmol) was added. The product slowly precipitated from the reaction mixture. After 2 h the reaction was completed and concentrated in vacuo to facilitate precipitation. The reaction mixture was cooled to −20° C. and the product collected by filtration to afford nucleoside 29 (7.64 g, 91%) as a white solid material. FAB-MS m/z found 517.0 ($[MH]^+$, calcd 517.1); $^1H$ NMR (DMSO-$d_6$) δ7.79 (d, J=1.3, 1H, H6), 7.45-7.32 (m, 5H, Ph), 6.40 (d, J=6.0, 1H, H1'), 5.60 (dd, J=6.1, 2.8, 1H, H2'), 4.82 (d, J=11.5, 1H, $CH_2Ph$), 4.70 (d, J=11.5, 1H, $CH_2Ph$), 4.51 (d, J=2.8, 1H, H3'), 4.43 (d, J=10.6, 1H), 4.36 (d, J=6.2, 1H), 4.33 (d, J=5.9, 1H), 4.25 (d, J=11.0, 1H) (H5', H1"), 3.22 (s, 3H, Ms), 3.16 (s, 3H, Ms), 1.80 (s, J=1.1, 3H, $CH_3$); $^{13}C$ NMR (DMSO-$d_6$) δ 171.5 (C4), 159.1 (C2), 136.9, 132.1, 128.5, 128.1, 127.9 (C6, Ph), 117.1 (C5), 89.1 (C1'), 86.1 (C2'), 85.4 (C4'), 83.7 (C3'), 72.4 ($CH_2Ph$), 68.6, 68.0 (C5', C1"), 36.9, 36.8 (Ms), 13.6 ($CH_3$); Anal. calcd for $C_{20}H_{24}N_2O_{10}S_2$: C, 46.5; H, 4.7; N, 5.4. Found: C, 46.6; H, 4.8; N, 5.3.

1-(3-O-Benzyl-5-O-methanesulfonyl-4-C-methanesulfonyloxymethyl-β-D-threo-pentofuranosyl)thymine (30)

Nucleoside 29 (3.70 g, 7.16 mmol) was suspended in a mixture of acetone (160 mL) and aq $H_2SO_4$ (0.1 M, 160 mL). The mixture was heated to reflux overnight with stirring. After cooling to rt a white solid precipitated. The volume was reduced to approx. ½ in vacuo and a white solid was isolated by filtration. The solid was washed thoroughly with water and dried in vacuo to give nucleoside 30 (3.77 g, 98%) as a white solid. FAB-MS m/z found 535.0 ($[MH]^+$, calcd 535.1); $^1H$ NMR (DMSO-$d_6$) δ11.35 (s, 1H, NH), 7.41-7.32 (m, 6H, H6, Ph), 6.20 (d, J=5.0, 1H, H1'), 6.10 (d, J=4.8, 1H, 2'-OH), 4.77 (d, J=11.9, 1H, $CH_2Ph$), 4.67 (d, J=11.9, 1H, $CH_2Ph$), 4.56 (d, J=10.6, 1H), 4.50-4.41 (m, 3H), 4.32 (d, J=10.6, 1H), 4.16 (d, J=3.7, 1H, H3'), 3.25 (s, 3H, Ms), 3.20 (s, 3H, Ms), 1.79 (s, 3H, $CH_3$); $^{13}C$ NMR (DMSO-$d_6$) δ 163.9 (C4), 150.6 (C2), 137.8, 137.6, 128.4, 127.9, 127.7 (C6, Ph), 108.2 (C5), 84.8 (C1'), 84.3 (C3'), 81.7 (C4'), 73.3 (C2'), 72.3 ($CH_2Ph$), 68.1, 67.6 (C5', C1"), 37.0, 36.8 (Ms), 12.2 ($CH_3$); Anal. calcd for $C_{20}H_{26}N_2O_{11}S_2$: C, 44.9; H, 4.9; N, 5.2. Found: C, 44.5; H, 4.8; N, 5.1.

1-(3-O-Benzyl-5-O-methanesulfonyl-4-C-methanesulfonyloxymethyl-2-O-trifluoromethanesulfonyl-β-D-threo-pentofuranosyl)thymine (31)

Nucleoside 30 (300 mg, 0.56 mmol) was dissolved in anhyd pyridine (2×5 mL) and concentrated in vacuo to remove water traces. The compound was dissolved in a mixture of anhyd dichloromethane (20 mL) and anhyd pyridine (0.45 mL, 5.60 mmol) followed by the addition of DMAP (274 mg, 2.24 mmol). After cooling to 0° C. trifluoromethanesulfonic anhydride (0.19 mL, 1.12 mmol) was added dropwise during 30 min. The reaction mixture was stirred for an additional 1.5 h and poured into ice cooled sat. aq $NaHCO_3$ (20 mL). The organic phase was separated and washed successively with aq HCl (1 M, 2×20 mL) and sat. aq $NaHCO_3$ (2×20 mL), dried ($Na_2SO_4$), filtered and evaporated in vacuo. The residue was purified by DCVC (0-100% EtOAc in n-heptane v/v) yielding nucleoside 31 (302 mg, 80%) as a white foam. FAB-MS m/z found 667.0 ($[MH]^+$, calcd 667.0); $^1H$ NMR (DMSO-$d_6$) δ 11.62 (br s, 1H, NH), 7.51 (s, 1H, H6), 7.40-7.33 (m, 5H, Ph), 6.45 (br s, 1H, H1'), 5.91 (t, J=6.0, 1H, H2'), 4.97 (d, J=5.7, 1H, H3'), 4.82-4.36 (m, 6H, $CH_2Ph$, H5'a, H5'b, H1"a, H1"b), 3.30 (s, 3H, Ms), 3.24 (s, 3H, Ms), 1.81 (s, 3H, $CH_3$); $^{13}C$ NMR (DMSO-$d_6$) δ 163.3 (C4), 150.0 (C2), 136.5, 128.3, 128.0, 127.8 (C6, Ph), 117.6 (q, J=320, $CF_3$), 110.1 (C5), 88.0 (C1'), 81.7, 81.0 (C3', C4'), 73.1 ($CH_2Ph$), 68.0, 67.6 (C5', C1"), 36.7, 36.6 (Ms), 11.8 ($CH_3$); Anal. calcd for $C_{21}H_{25}F_3N_2O_{13}S_3$: C, 37.8; H, 3.8; N, 4.2. Found: C, 38.1; H, 3.8; N, 4.1.

1-(2-Azido-3-O-benzyl-2-deoxy-5-O-methanesulfonyl-4-C-(methanesulfonyloxymethyl)-β-D-erythropentofuranosyl)thymine (32)

Method A: To a solution of nucleoside 31 (215 mg, 0.32 mmol) in anhyd DMF (10 mL) NaN$_3$ (23 mg, 0.35 mmol) and 15-crown-5 (64 µL, 0.32 mmol) was added. The mixture was stirred at 80° C. for 1 h and then cooled to rt whereupon water (20 mL) was added. The solution was extracted with EtOAc (50 mL) and the organic phase was washed with sat. aq NaHCO$_3$ (2×20 mL), dried (Na$_2$SO$_4$), filtered and evaporated to dryness in vacuo. The residue was purified by DCVC (50-100% EtOAc in n-heptane v/v) yielding nucleoside 32 (164 mg, 91% from 31) as a white foam. Analytical data were identical to those reported above.

Method B: A solution of nucleoside 30 (5.35 g, 10 mmol) in anhyd dichloromethane (300 mL) was cooled to 0° C. Anhyd pyridine (8.08 mL, 100 mmol) and DMAP (4.89 g, 40 mmol) was added followed by the dropwise addition of trifluoromethansulfonic anhydride (3.3 mL, 20 mmol). After 2 h at 0° C. the reaction was quenched by the addition of ice cold sat. aq NaHCO$_3$ (200 mL) and the reaction mixture was transferred to a separatory funnel. The phases were separated and the aq phase was extracted with dichloromethane (200 mL). The combined organic phases were washed with aq HCl (1.0 M, 2×300 mL) and sat. aq NaHCO$_3$ (300 mL), dried (Na$_2$SO$_4$), filtered and concentrated in vacuo to give a white solid. The solid was dissolved in anhyd DMF (300 mL) and NaN$_3$ (1.86 g, 30 mmol) was added. After stirring at rt for 4 h brine (300 mL) was added and the mixture was transferred to a separatory funnel. The aq phase was extracted with dichloromethane (3×200 mL) and the combined organic phases were dried (Na$_2$SO$_4$), filtered and concentrated in vacuo yielding a yellow residue that was purified by DCVC (Ø 5 cm, 25-100% EtOAc in n-heptane v/v, 5% increments, 100 mL fractions) affording nucleoside 32 (5.1 g, 91% from 30) as a white solid. Analytical data were identical to those reported above.

(1R,3R,4R,7S)-7-Benzyloxy-1-methansulfonyloxymethyl-3-(thymin-1-yl)-2-oxa-5-azabicyclo[2:2:1]heptane (33).

To a solution of 32 (5.83 g, 10.4 mmol) in THF (300 mL) at rt aq NaOH (2.0 M, 104 mL, 208 mmol) and PMe$_3$ in THF (1.0 M, 20.8 mL, 20.8 mmol) was added with stirring. After 8 h the THF was partly removed under reduced pressure. Brine (200 mL) and EtOAc (300 mL) was added and the phases were separated. The aq phase was extracted with EtOAc (2×300 mL) and dichloromethane (2×300 mL). The combined organic phases were dried (Na$_2$SO$_4$), filtered and concentrated in vacuo to give nucleoside 33 (4.22 g, 93%) as a white solid. R$_f$=0.15 (10% MeOH in EtOAc, v/v); ESI-MS m/z found 438.0 ([MH]$^+$, calcd 438.1); $^1$H NMR (DMSO-d$_6$) δ11.33 (br s, 1H, NH), 7.46 (s, 1H, H6), 7.36-7.27 (m, 5H, Ph), 5.44 (s, 1H, H1'), 4.67 (d, J=11.7, 1H), 4.59 (d, J=11.5, 1H), 4.56 (d, J=11.9, 1H), 4.52 (d, J=11.7, 1H) (H5', CH$_2$Ph), 3.84 (s, 1H, H3'), 3.65 (s, 1H, H2'), 3.26 (s, 3H, Ms), 3.06 (d, J=10.1, 1H, H1"a), 2.78 (d, J=9.9, 1H, H1"b), 1.77 (s, 3H, CH$_3$); $^{13}$C NMR (DMSO-d$_6$) δ 163.9 (C4), 150.1 (C2), 137.9, 134.7, 128.2, 127.7, 127.6 (C6, Ph), 108.3 (C5), 88.4 (C1'), 85.6 (C4'), 76.3 (C3'), 70.9, 66.6 (CH$_2$Ph, C5'), 59.4 (C2'), 50.1 (C1"), 36.9 (Ms), 12.3 (CH$_3$); Anal. calcd for C$_{19}$H$_{23}$N$_3$O$_7$S: C, 52.1; H, 5.3; N, 9.6. Found: C, 52.0; H, 5.2; N, 9.2.

(1R,3R,4R,7S)-7-Benzyloxy-1-methansulfonyloxymethyl-5-methyl-3-(thymin-1-yl)-2-oxa-5-azabicyclo[2:2:1]heptane (34).

To a solution of 33 (4.22 g, 9.64 mmol) in formic acid (20 mL) formaldehyde (37% aq solution, 20 mL) was added with stirring and the reaction mixture was heated to 80° C. After 1 h the reaction was diluted with EtOAc (150 mL) and quenched by carefully pouring it into sat. aq NaHCO$_3$ (100 mL). The phases were separated and the organic phase was washed with sat. aq NaHCO$_3$ (4×100 mL). The combined aq phases were extracted with dichloromethane (2×200 mL). The combined organic phases were dried (Na$_2$SO$_4$), filtered and concentrated under reduced pressure. Purification by DCVC (Ø 6 cm, 0-15% MeOH in EtOAc v/v, 1% increments, 100 mL fractions) afforded nucleoside 34 (3.89 g, 90%) as an off-white solid. R$_f$=0.30 (10% MeOH in EtOAc, v/v); ESI-MS m/z found 452.1 ([MH]$^+$, calcd 452.1); $^1$H NMR (DMSO-d$_6$) 11.34 (br s, 1H, NH), 7.43 (s, 1H, H6), 7.34-7.28 (m, 5H, Ph), 5.58 (s, 1H, H1'), 4.67 (m, 4H, H5', CH$_2$Ph), 3.88 (s, 1H, H3'), 3.58 (s, 1H, H2'), 3.27 (s, 3H, Ms), 2.98 (d, J=9.7, 1H, H1"a), 2.76 (d, J=9.7, 1H, H1"b), 2.57 (s, 3H, NCH$_3$), 1.76 (s, 3H, CH$_3$); $^{13}$C NMR (DMSO-d$_6$) δ 163.9 (C4), 149.9 (C2), 137.6 (Ph), 134.6 (C6), 128.3, 127.7 (Ph), 108.4 (C5), 86.1 (C1'), 85.3 (C4'), 77.3 (C3'), 71.0, 66.3 (CH$_2$Ph, C5'), 64.9 (C2'), 58.7 (C1"), 40.8 (NCH$_3$), 36.9 (Ms), 12.3 (CH$_3$); Anal. calcd for C$_{20}$H$_{25}$N$_3$O$_7$S.0.25 H$_2$O: C, 52.7; H, 5.6; N, 9.1. Found: C, 52.9; H, 5.6; N, 8.9.

(1R,3R,4R,7S)-7-Benzyloxy-1-hydroxymethyl-5-methyl-3-(thymin-1-yl)-2-oxa-5-azabicyclo[2:2:1]heptane (35).

Compound 34 (3.00 g, 6.64 mmol) was dissolved in anhyd DMF (30 mL) and sodium benzoate (1.93 g, 13.3 mmol) was added. The reaction mixture was heated to 100° C. for 7 h and then cooled to rt. Sodium methoxide (1.44 g, 26.6 mmol) was added and after 1 h the reaction was diluted with dichloromethane (100 mL) and washed with brine (2×100 mL). The combined aq phases were extracted with dichloromethane (2×50 mL). The combined organic phases were dried (Na$_2$SO$_4$) and concentrated under reduced pressure. The residue was dissolved in aq HCl (1 M, 15 mL) and lyophilised yielding an off-white solid. Purification by DCVC (Ø 4 cm, 0-10% MeOH in dichloromethane v/v, 0.5% increments, 50 mL fractions) afforded the hydrochloride salt of nucleoside 35 (2.72 g, 98%) as an off-white solid. R$_f$=0.19 (7% MeOH in dichloromethane, v/v); ESI-MS m/z found 374.1 ([MH]$^+$, calcd 374.2), 408.1, 410.1 ([MCl]$^-$, calcd 408.1, 410.1); $^1$H-NMR (DMSO-d$_6$) δ11.43 (br s, 1H, NH), 7.63 (s, 1H, H6), 7.45-7.29 (m, 5H, Ph), 5.60 (s, 1H, H1'), 4.80 (t, J=5.7, 1H, 5'-OH), 4.67-4.50 (m, 2H, CH$_2$Ph), 3.87 (s, 1H, H3'), 3.67 (d, J=6.0, 2H, H5'), 3.38 (s, 1H, H2'), 2.88 (d, J=9.2, 1H, H1"a), 2.66 (d, J=9.5, 1H, H1"b), 2.57 (s, 3H, NCH$_3$), 1.75 (s, 3H, CH$_3$); $^{13}$C NMR (DMSO-d$_6$) δ 164.0 (C4), 149.8 (C2), 137.0 (Ph), 134.4 (C6), 128.5, 127.8 (Ph), 108.9 (C5), 88.4 (C1'), 88.0 (C4'), 77.8 (C3'), 71.0, (CH$_2$Ph), 66.0, 65.7 (C2', C5'), 61.4 (C1"), 40.1 (NCH$_3$), 12.6 (CH$_3$); Anal. calcd for C$_{19}$H$_{23}$N$_3$O$_5$.HCl.H$_2$O: C, 53.3; H, 6.1; N, 9.8. Found: C, 53.0; H, 6.3; N, 9.6.

(1R,3R,4R,7S)-7-Hydroxy-1-hydroxymethyl-5-methyl-3-(thymin-1-yl)-2-oxa-5-azabicyclo[2:2:1]heptane (36).

Compound 35 (2.60 g, 6.64 mmol) was dissolved in glacial acetic acid (50 mL) and the reaction flask was evacuated and filled with argon several times. Pd(OH)$_2$ on charcoal (20% moist, 200 mg) was added and the reaction flask was evacuated and filled with hydrogen gas several times. The reaction was stirred vigorously under an atmosphere of hydrogen gas for 8 h. The catalyst was removed by filtration through a plug of celite. The celite was washed thoroughly with hot methanol (200 mL). The solvents were removed in vacuo. The residue was dissolved in water (10 mL) and lyophilised yielding the acetate salt of nucleoside 36 (2.10 g, 97%) as off-white flakes. R$_f$=0.11 (0.5% Et$_3$N, 10% MeOH, 89.5% EtOAc, v/v/v); ESI-MS m/z found 284.1 ([MH]$^+$, calcd 284.1). All analytical data were identical to those previously reported.[7]

(1R,3R,4R,7S)-1-(4,4'-Dimethoxytrityloxymethyl)-7-hydroxy-5-methyl-3-(thymin-1-yl)-2-oxa-5-azabicyclo[2:2:1]heptane (37).

Compound 36 (2.00 g, 5.83 mmol) was dissolved in anhyd pyridine (2×50 mL) and concentrated in vacuo. The nucleoside was dissolved in anhyd pyridine (50 mL) and 4,4'-dimethoxytrityl chloride (2.96 g, 8.74 mmol) was added and the reaction was stirred at rt for 9 h. The reaction was concentrated to ½ volume in vacuo and the residue was diluted with EtOAc (100 mL). The organic phase was washed with sat. aq NaHCO$_3$ (3×100 mL) and brine (100 mL), dried (Na$_2$SO$_4$), filtered and concentrated under reduced pressure. Purification by DCVC (Ø 4 cm, 0-10% MeOH in EtOAc+ 0.5% TEA v/v, 0.5% increments, 50 mL fractions) afforded nucleoside 37 (3.13 g, 92%) as off-white solid. R$_f$=0.38 (0.5% Et$_3$N, 10% MeOH, 89.5% EtOAc, v/v/v); ESI-MS m/z found 586.2 ([MH]$^+$, calcd 586.2). All analytical data were identical to those previously reported. (Singh, S. K.; Kumar, R.; Wengel, J. *J. Org. Chem.* 1998, 63, 10035-10039)

(1R,3R,4R,7S)-7-(2-Cyanoethoxy(diisopropylamino)phosphinoxy)-1-(4,4'-dimethoxytrityloxymethyl)-5-methyl-3-(thymin-1-yl)-2-oxa-5-azabicyclo[2.2.1]heptane (38)

Compound 37 (500 mg, 0.85 mmol) was dissolved in anhyd dichloromethane (4 mL) and 4,5-dicyanoimidazole in MeCN (1.0 M, 0.59 mL, 0.59 mmol) was added at ambient temperature with stirring. 2-Cyanoethyl-N,N,N',N'-tetraisopropylphosphorodiamidite (0.27 mL, 0.85 mmol) was added dropwise to the reaction mixture. After 2 h the reaction was diluted with dichloromethane (10 mL) and transferred to a separatory funnel and extracted with sat. aq NaHCO$_3$ (2×15 mL) and brine (15 mL). The combined aq phases were extracted with dichloromethane (10 mL). The organic phases were pooled and dried (Na$_2$SO$_4$). After filtration the organic phase was evaporated in vacuo to give nucleoside 29 as a slightly yellow foam (660 mg, 98% yield). R$_f$=0.56 (0.5% Et$_3$N, 10% MeOH, 89.5% EtOAc, v/v/v); ESI-MS m/z found 786.3 ([MH]$^+$, calcd 786.4). $^{19}$P NMR (CDCl$_3$) δ149.8, 149.6. (Singh, S. K.; Kumar, R.; Wengel, J. *J. Org. Chem.* 1998, 63, 10035-10039)

(1R,3R,4R,7S)-1-(4,4'-Dimethoxytrityloxymethyl)-7-hydroxy-5-N-methyl-3-(4-N-benzoyl-5-methyl-cytosine-1-yl)-2-oxa-5-azabicyclo[2:2:1]heptane (43)

Compound 37 (1.5 g, 2.5 mmol) was dissolved in anhyd pyridine (25 mL). Acetic anhydride (2.4 mL, 25 mmol) was added and the reaction stirred for 24 h at ambient temperature. The reaction was quenched with water (25 mL) and extracted with EtOAc (2×25 ml). The combined organic phases were washed with sat. aq. NaHCO$_3$ (2×50 ml), brine (50 ml), and dried (Na$_2$SO$_4$). The organic phase was filtered and evaporated in vacuo to give compound 39 as a white foam. Residual water was removed from the crude product by evaporation from anhyd MeCN. The product was then dissolved in anhyd MeCN (50 ml) and Et$_3$N (3.5 mL, 25.3 mmol) was added followed by 1,2,4-triazole (1.75 g, 25 mmol). The reaction mixture was cooled on an icebath and POCl$_3$ (0.48 mL, 5.0 mmol) was added dropwise to give a white slurry. After 15 min the reaction mixture was allowed to reach room temperature. The resulting yellow slurry was stirred under argon at ambient temperature. After 4.5 h the reaction mixture was poured into a slurry of sat. aq NaHCO$_3$ (50 mL) and ice and extracted with EtOAc (3×25 mL). The combined organic phases were washed with brine (100 ml) and dried (Na$_2$SO$_4$). Filtration and evaporation in vacuo afforded the trialzolide 40 as a pink foam which was immediately dissolved in anhyd MeCN (50 ml) and sat. aq NH$_4$OH (50 mL) was added. After stirring for 16 h solid NaCl was added until the phases separated. The aq phase was extracted with EtOAc (3×50 mL) and the combined organic phases dried (Na$_2$SO$_4$), filtered and evaporated to give nucleoside 41 as an off-white solid. The product was dissolved in anhyd pyridine (50 mL) and benzoyl chloride (0.87 mL, 7.5 mmol) was added. The reaction was stirred for 3 h under argon and then concentrated in vacuo. The residue was diluted with EtOAc (100 mL) and extracted with sat. aq NaHCO$_3$ (100 mL). The phases were separated and the aq phase extracted with EtOAc (2×100 ml). The combined organic phases were washed with brine (200 ml) and dried (Na$_2$SO$_4$). Filtration and evaporation of the organic phase produced a clear oil 42 that was dissolved in THF (100 mL). LiOH (aq, 1.0 M, 25 mL) was added and the reaction was stirred for 2 h. The reaction mixture was transferred to a separatory funnel with EtOAc (100 mL) and brine (100 mL) and extracted with EtOAc (2×100 ml). The combined organic phases were washed with brine (200 ml) and dried (Na$_2$SO$_4$). Filtration and evaporation in vacou gave a yellow foam that was purified by DCVC (Ø 4 cm, 50-100% EtOAc, n-heptane v/v (the column was pretreated with 1% Et$_3$N in heptane v/v), 5% increments, 100 mL fractions)) affording nucleoside 43 (1.12 g, 65%) as a white solid. R$_f$=0.56 (EtOAc); ESI-MS m/z found 689.3 ([MH]$^+$, calcd. 689.3); $^1$H NMR (DMSO-d$_6$) δ8.16 (s, 2H, Bz), 7.86 (s, 1H, H6), 7.61-7.44 (m, 5H, Bz, DMT), 7.36-7.24 (m, 7H, Bz, DMT), 6.92 (dd, 4H, J=9.0, 2.4, DMT), 5.64 (s, 1H, H1'), 5.41 (d, J=5.3, 1H, H3'), 4.14 (d, J=5.3, 1H, H2'), 5.64 (s, 1H, H1'), 3.75 (s, 6H, OCH$_3$), 3.39 (d, J=10.8, 1H, H5'), 3.28 (d, J=10.8 Hz, 1H, H5'), 2.89 (d, J=9.5, 1H, H1"), 2.59 (s, 3H, NCH$_3$), 2.58 (d, J=9.2, 1H, H1"), 1.73 (s, 3H, CH$_3$); $^{13}$C NMR (DMSO-d$_6$) E 178.2 (PhC(O)), 160.3 (C4), 158.2 (Ph), 147.0 (C2), 144.8 (Ph), 137.4 (C6), 135.4, 135.2, 132.5, 129.9, 129.3, 128.4, 128.0, 127.7, 126.9, 113.3 (Ph), 108.6 (C5), 88.9 (C1'), 85.7 (C4'), 85.0 (Ph), 70.5 (C3'), 67.0 (C5'), 59.6, 58.6 (C2', C1"), 55.1 (OCH$_3$), 40.1 (NCH$_3$), 14.1 (CH$_3$); Anal. calcd. for C$_{40}$H$_{40}$N$_4$O$_7$: C, 69.7; H, 5.9; N, 8.1. Found: C, 69.5; H, 5.9; N, 7.7.

(1R,3R,4R,7S)-1-(4,4'-Dimethoxytrityloxymethyl)-7-(2-cyanoethoxy(diisopropylamino)phosphinoxy)-5-N-methyl-3-(4-N-benzoyl-5-methyl-cytosine-1-yl)-2-oxa-5-azabicyclo[2:2:1]heptane (44)

Compound 43 (0.50 g, 0.73 mmol) was dissolved in anhyd dichloromethane (10 mL) and 4,5-dicyanoimidazole in MeCN (1.0 M, 0.51 mL, 0.51 mmol) was added at ambient temperature with stirring. 2-Cyanoethyl-N,N,N'N'-tetraisopropylphosphorodiamidite (0.23 mL, 0.74 mmol) was added dropwise to the reaction mixture. After 2 h the reaction was diluted with dichloromethane (20 mL) and transferred to a separatory funnel and extracted with sat. aq NaHCO$_3$ (2×30 mL) and brine (30 mL). The combined aq phases were extracted with dichloromethane (30 mL). The organic phases were pooled and dried (Na$_2$SO$_4$). After filtration the organic phase was evaporated in vacuo to give a yellow foam. Purification by DCVC (Ø 4 cm, 0-100% EtOAc, n-heptane, 0.5% Et$_3$N v/v/v (the column was pretreated with 1% Et$_3$N in heptane v/v), 5% increments, 50 mL fractions) afforded nucleoside 44 (0.58 g, 92%) as a white solid. R$_f$=0.67 (20% heptane, 79.5% EtOAc, 0.5% Et$_3$N, v/v/v); ESI-MS m/z found 889.2 ([MH]$^+$, calcd 889.4); $^{31}$P NMR (DMSO-d$_6$) δ148.4, 147.4

1-(3-O-Benzoyl-5-O-methanesulfonyl-4-C-methanesulfonyloxymethyl-β-D-threo-pentofuranosyl)thymine (52)

Anhydronucleoside 29 (30.00 g, 58.1 mmol) was heated to 70° C. in a mixture of methanol (1000 ml) and acetone (1000 ml) until a clear solution was obtained and the solution was allowed to reach room temperature. The reaction flask was flushed with argon and Pd/C (10 wt. % Pd on carbon, 6.2 g, 5.8 mmol) was added. The mixture was stirred vigorously under an atmosphere of hydrogen gas (balloon). After 23 h the slurry was filtered through a pad of celite. The catalyst was recovered from the celite and refluxed in DMF (1000 ml) for 1 h. The hot DMF slurry was filtered through a pad of celite and the organic phases pooled and evaporated in vacuo to give 2,2'-anhydro-1-(3-hydroxy-5-O-nnethanesulfonyl-4-C-methanesulfonyloxymethyl-β-D-threo-pentofuranosyl) thymine (50) as a yellow powder. Residual solvents were removed on a high vacuum pump overnight. The crude nucleoside 50 (23 g) was heated to 70° C. in DMF (300 ml) to give a clear yellow solution that was allowed to cool to room temperature. Benzoyl chloride (81.7 g, 581 mmol, 67.4 ml) was added followed by anhydrous pyridine (70 ml). After 18 h the reaction was quenched with methanol (200 ml) and excess methanol was removed in vacuo. To the dark brown solution of nucleoside 51 (2,2'-anhydro-1-(3-O-benzoyl-5-O-methanesulfonyl-4-C-methanesulfonyloxymethyl-β-D-threo-pentofuranosyl)thymine) aqueous H$_2$SO$_4$ (0.25 M, 400 ml) was added. The solution was heated to 80° C. on an oil bath (At approx 50° C. precipitation occurs. The solution becomes clear again at 80° C.). After 22 h at 80° C. the solution was allowed to cool down to room temperature. The reaction mixture was transferred to a separatory funnel with EtOAc (1000 ml). The organic phase was extracted with sat. aq. NaHCO$_3$ (2×1000 ml). The combined aqueous phases were extracted with EtOAc (1000+500 ml). The organic phases were pooled and extracted once more with sat. aq. NaHCO$_3$ (1000 ml), dried (Na$_2$SO$_4$), filtered and evaporated in vacuo to give a yellow liquid. Residual solvents were removed on a high vacuum pump overnight to give a yellow syrup. The product was purified by Dry Column Vacuum Chromatography (Ø 10 cm, 50-100% EtOAc in n-heptane (v/v), 100 ml fractions, 10% increments, followed by 2-24% MeOH in EtOAc (v/v), 100 ml fractions, 2% increments). Fractions containing the product were combined and evaporated in vacuo affording nucleoside 52 (25.1 g, 79%) as a white foam. R$_f$=0.54 (5% MeOH in EtOAc, v/v); ESI-MS m/z found 549.0 ([MH]$^+$, calcd 549.1); $^1$H NMR (DMSO-d$_6$) δ11.39 (br s, 1H, NH), 8.10-8.08 (m, 2H, Ph), 7.74-7.70 (m, 1H, Ph), 7.60-7.56 (m, 2H, Ph), 7.51 (d, J=1.1, 1H, H6), 6.35 (d, J=4.9, 1H, H1'), 6.32 (d, J=5.3, 1H, 2'-OH), 5.61 (d, J=4.0, 1H, H3'), 4.69 (d, J=10.8, 1H), 4.59 (m, 1H, H2'), 4.55 (d, J=10.8, 1H), 4.52 (d, J=10.8, 1H), 4.46 (d, J=10.6, 1H) (H5' and H1''), 3.28 (s, 3H, Ms), 3.23 (s, 3H, Ms), 1.81 (s, 3H, CH$_3$); $^{13}$C NMR (DMSO-d$_6$) δ164.5, 163.6 (C4, PhC(O)), 150.3 (C2), 137.7 (C6), 133.8, 129.6, 128.7, 128.6 (Ph), 108.1 (C5), 84.8 (C1'), 81.1 (C4'), 78.0 (C3'), 73.2 (C2'), 68.0, 67.1 (C5', C1''), 36.7, 36.6 (Ms), 11.9 (CH$_3$); Anal. calcd for C$_{20}$H$_{24}$N$_2$O$_{12}$S$_2$.0.33 H$_2$O: C, 44.34; H, 4.65; N, 4.85. Found: C, 44.32; H, 4.58; N, 4.77.

(1R,3R,4R,7R)-7-Benzoyloxy-1-methansulfonyloxymethyl-3-(thymin-1-yl)-2-oxa-5-thiabicyclo[2:2:1]heptane (54)

1-(3-O-Benzoyl-5-O-methanesulfonyl-4-C-methanesulfonyl-oxymethyl-β-D-threo-pentofuranosyl)thymine (52) (10.00 g, 18.23 mmol) was dissolved in anhydrous dichloromethane (500 ml) and cooled to 0° C. Pyridine (15 ml) and DMAP (8.91 g, 72.9 mmol) was added followed by dropwise addition of trifluoromethanesulfonic anhydride (10.30 g, 36.5 mmol, 6.0 ml). After 1 h the reaction was quenched with sat. aq. NaHCO$_3$ (500 ml) and transferred to a separatory funnel. The organic phase was extracted with 1.0 M aq HCl (500 ml), sat. aq NaHCO$_3$ (500 ml) and brine (500 ml). The organic phase was evaporated in vacuo with toluene (100 ml) to give 1-(3-O-benzoyl-5-O-methanesulfonyl-4-C-methanesulfonyloxymethyl-2-O-trifluoromethanesulfonyl-β-D-threo-pentofuranosyl)thymine (53) as a yellow powder. The crude nucleoside 53 was dissolved in anhydrous DMF (250 ml) and Na$_2$S (1.57 g, 20.1 mmol) was added to give a dark green slurry. After 3 h the reaction was quenched with half sat. aq. NaHCO$_3$ (500 ml) and extracted with CH$_2$Cl$_2$ (500+2×250 ml). The combined organic phases were extracted with brine (500 ml), dried (Na$_2$SO$_4$), filtered and concentrated in vacuo to give a yellow liquid. Residual solvent was removed overnight on a high vacuum pump to give a yellow gum that was purified by Dry Column Vacuum Chromatography (Ø 6 cm, 50-100% EtOAc in n-heptane (v/v), 50 ml fractions, 10% increments, followed by 2-20% MeOH in EtOAc (v/v), 50 ml fractions, 2% increments) to give nucleoside 54 (6.15 g, 72%) as a yellow foam.

R$_f$=0.27 (20% n-heptane in EtOAc, v/v); ESI-MS m/z found 469.0 ([MH]$^+$, calcd 469.1); $^1$H NMR (CDCl$_3$) δ 8.70 (br s, 1H, NH), 8.01-7.99 (m, 2H, Ph), 7.67 (d, J=1.1, 1H, H6), 7.65-7.61 (m, 1H, Ph), 7.50-7.46 (m, 2H, Ph), 5.98 (s, 1H, H1'), 5.34 (d, J=2.4, 1H, H3'), 4.66 (d, J=11.7, 1H, H5'a), 4.53 (d, J=11.5, 1H, H5' b), 4.12 (m (overlapping with residual EtOAc), 1H, H2'), 3.15-3.13 (m, 4H, H1''a and Ms), 3.06 (d, J=10.6, 1H, H1''b), 1.98 (d, J=1.1, 3H, CH$_3$); $^{13}$C NMR (CDCl$_3$) δ 165.2, 163.5 (C4, PhC(O)), 149.9 (C2), 134.1, 133.9, 129.8, 128.7, 128.3 (C6, Ph), 110.7 (C5), 91.1 (C1'), 86.8 (C4'), 72.6 (C3'), 65.8 (C5'), 50.5 (C2'), 37.9 (Ms), 35.1 (C1''), 12.5 (CH$_3$); Anal. calcd for C$_{19}$H$_{20}$N$_2$O$_8$S$_2$.0.33 EtOAc: C, 49.21; H, 4.72; N, 5.47. Found: C, 49.25; H, 4.64; N, 5.48.

(1R,3R,4R,7R)-7-Benzoyloxy-1-benzoyloxymethyl-3-(thymin-1-yl)-2-oxa-5-thiabicyclo[2:2:1]heptane (55)

Nucleoside 54 (1.92 g, 4.1 mmol) was dissolved in anhydrous DMF (110 ml). Sodium benzoate (1.2 g, 8.2 mmol) was added and the mixture was heated to 100° C. for 24 h. The reaction mixture was transferred to a separatory funnel with half sat. brine (200 ml) and extracted with EtOAc (3×100 ml). The combined organic phases were dried (Na$_2$SO$_4$), filtered and evaporated in vacuo to give a brown liquid. The product was put on a high vacuum pump to remove residual solvent. The resulting brown gum was purified by Dry Column Vacuum Chromatography (Ø 4 cm, 0-100% EtOAc in n-heptane (v/v), 50 ml fractions, 10% increments, followed by 2-10% MeOH in EtOAc (v/v), 50 ml fractions, 2% increments) to afford nucleoside 55 (1.64 g, 81%) as a slightly yellow foam. $R_f$=0.57 (20% n-heptane in EtOAc, v/v); ESI-MS m/z found 495.1 ([MH]$^+$, calcd 495.1); $^1$H NMR (CDCl$_3$) δ 9.02 (br s, 1H, NH), 8.07-7.99 (m, 4H, Ph), 7.62-7.58 (m, 2H, Ph), 7.47-7.42 (m, 5H, Ph and H6), 5.95 (s, 1H, H1'), 5.46 (d, J=2.2, 1H, H3'), 4.93 (d, J=12.8, 1H, H5' a), 4.60 (d, J=12.8, 1H, H5' b), 4.17 (d, J=2.2, 1H, H2'), 3.27 (d, J=10.6, 1H, H1"a), 3.16 (d, J=10.6, 1H, H1"b), 1.55 (d, J=1.1, 3H, CH$_3$); $^{13}$C NMR (CDCl$_3$) δ 165.8, 165.1, 163.7 (C4, 2×Ph C(O)), 150.0 (C2), 133.9, 133.7, 133.6, 129.8, 129.6, 129.0, 128.8, 128.6, 128.5 (C6, 2×Ph), 110.3 (C5), 91.3 (C1'), 87.5 (C4'), 72.9 (C3'), 61.3 (C5'), 50.6 (C2'), 35.6 (C1"), 12.3 (CH$_3$); Anal. calcd for C$_{25}$H$_{22}$N$_2$O$_7$S: C, 60.72; H, 4.48; N, 5.66. Found: C, 60.34; H, 4.49; N, 5.35.

(1R,3R,4R,7R)-7-Hydroxy-1-hydroxymethyl-3-(thymin-1-yl)-2-oxa-5-thiabicyclo[2:2:1]heptane (56)

Nucleoside 55 (1.50 g, 3.0 mmol) was dissolved in methanol saturated with ammonia (50 ml). The reaction flask was sealed and stirred at ambient temperature for 20 h. The reaction mixture was concentrated in vacuo to give a yellow gum that was purified by Dry Column Vacuum Chromatography (Ø 4 cm, 0-16% MeOH in EtOAc (v/v), 1% increments, 50 ml fractions) affording nucleoside 56 (0.65 g, 76%) as clear crystals. $R_f$=0.31 (10% MeOH in EtOAc, v/v); ESI-MS m/z found 287.1 ([MH]$^+$, calcd 287.1); $^1$H NMR (DMSO-d$_6$) δ11.32 (br s, 1H, NH), 7.96 (d, J=1.1, 1H, H6), 5.95 (s, 1H, H6), 5.70 (d, J=4.2, 1H, 3'-OH), 5.62 (s, 1H, H1'), 4.49 (t, J=5.3, 1H, 5'-OH), 4.20 (dd, J=4.1 and 2.1, 1H, H3'), 3.77-3.67 (m, 2H, H5'), 3.42 (d, J=2.0, 1H, H2'), 2.83 (d, J=10.1, 1H, H1"a), 2.64 (d, J=10.1, 1H, H1"b), 1.75 (d, J=1.1, 3H, CH$_3$); $^{13}$C NMR (DMSO-d$_6$) δ 163.8 (C4), 150.0 (C2), 135.3 (C6), 107.5 (C5), 90.2, 89.6 (C1' and C4'), 69.4 (C3'), 58.0 (C5'), 52.1 (C2'), 34.6 (C1"), 12.4 (CH$_3$); Anal. calcd for C$_{11}$H$_{14}$N$_2$O$_6$S: C, 46.15; H, 4.93; N, 9.78. Found: C, 46.35; H, 4.91; N, 9.54.

(1R,3R,4R,7R)-1-(4,4'-Dimethoxytrityloxymethyl)-7-hydroxy-5-methyl-3-(thymin-1-yl)-2-oxa-5-thiabicyclo[2:2:1]heptane (57)

Nucleoside 56 (0.60 g, 2.1 mmol) was dissolved in anhydrous pyridine (10 ml). 4,4'-Dimethoxytrityl chloride (0.88 g, 2.6 mmol) was added and the reaction was stirred at ambient temperature for 3 h. The reaction mixture was transferred to a separatory funnel with water (100 ml) and extracted with EtOAc (100+2×50 ml). The combined organic phases were washed with sat. aq NaHCO$_3$ (100 ml), brine (100 ml) and evaporated to dryness in vacuo to give a viscous yellow liquid. The product was redissolved in toluene (50 ml) and concentrated in vacuo to give a yellow foam. The foam was dried on a high vacuum pump overnight and purified by Dry Column Vacuum Chromatography (Ø 4 cm, 10-100% EtOAc in n-heptane (v/v), 10% increments, 50 mL fractions) affording nucleoside 57 (1.08 g, 88%) as a white foam. $R_f$=0.24 (20% n-heptane in EtOAc, v/v); ESI-MS m/z found 587.1 ([M−H]$^+$, calcd 587.19); $^1$H NMR (CDCl$_3$) δ 8.96 (br s, 1H, NH), 7.74 (d, J=1.1, 1H, H6), 7.46-7.44 (m, 2H, Ph), 7.35-7.22 (m, 9H, Ph), 7.19-7.7.15 (m, 2H, Ph), 6.86-6.80 (m, 4H, Ph), 5.82 (s, 1H, H1'), 4.55 (dd, J=9.3 and 2.1, 1H, H3'), 3.79 (s, 6H, OCH$_3$), 3.71 (d, J=2.0, 1H, H2'), 3.50 (s, 2H, H5'), 2.81 (d, J=10.8, 1H, H1"a), 2.77 (d, J=10.8, 1H, H1"b), 2.69 (d, J=9.2, 1H, 3'-OH), 1.42 (s, 3H, CH$_3$); $^{13}$C NMR (CDCl$_3$) δ 158.7 (C4), 150.1 (C2), 144.1, 135.2, 135.1, 130.1, 129.1, 128.1, 128.0, 127.1, 127.0 (C6, Ph), 113.3 (Ph), 110.0 (C5), 90.2 (C(Ph)$_3$), 89.6 (C1'), 87.0 (C4'), 71.7 (C3'), 60.9 (C5'), 55.2 (C2'), 34.7 (C1"), 12.2 (CH$_3$); Anal. calcd for C$_{32}$H$_{32}$N$_2$O$_7$S.0.5 H$_2$O: C, 64.31; H, 5.57; N, 4.69. Found: C, 64.22; H, 5.67; N, 4.47.

(1R,3R,4R,7R)-7-(2-Cyanoethoxy(diisopropylamino)phosphinoxy)-1-(4,4'-dimethoxytrityloxymethyl)-3-(thymin-1-yl)-2-oxa-5-thiabicyclo[2.2.1]heptane (58)

Nucleoside 57 (0.78 g, 1.33 mmol) was dissolved in anhydrous dichloromethane (5 ml) and a 1.0 M solution of 4,5-dicyanoimidazole in acetonitrile (0.93 ml, 0.93 mmol) was added followed by dropwise addition of 2-cyanoethyl-N,N,N',N'-tetraisopropylphosphorodiamidite (0.44 ml, 1.33 mmol). After 2 h the reaction was transferred to a separatory funnel with dichloromethane (40 ml) and extracted with sat. aq NaHCO$_3$ (2×25 ml) and brine (25 ml). The organic phase was dried (Na$_2$SO$_4$), filtered and evaporated in vacuo to give nucleoside 58 (1.04 g, 99%) as a white foam.
$R_f$=0.29 and 0.37—two diastereoisomers (20% n-heptane in EtOAc, v/v); ESI-MS m/z found 789.3 ([MH]$^+$, calcd 789.30); $^{31}$P NMR (DMSO-d$_6$) δ 150.39, 150.26

(1R,3R,4R,7S)-7-Benzyloxy-1-methansulfonyloxymethyl-3-(thymin-1-yl)-2-oxa-5-thiabicyclo[2:2:1]heptane (60).

Nucleoside 31 (0.10 g, 0.17 mmol) was dissolved in anhyd DMF (1 mL) and potassium thioacetate (25 mg, 0.22 mmol) was added. The reaction was stirred at ambient temperature for 5 h and transferred to a separatory funnel with brine (10 mL). The aq phase was extracted with dichloromethane (3×10 mL) and the combined organic phases dried (Na$_2$SO$_4$), filtered and evaporated in vacuo to give a yellow liquid. The crude product 59 was dissolved in THF (2 mL) and LiOH.H$_2$O (35 mg in 1 mL water, 0.84 mmol) was added. After 20 min the reaction was completed and quenched by the addition of glacial acetic acid (0.5 mL). The THF was removed in vacuo and the residue dissolved in dichloromethane (10 mL) and extracted with sat. aq NaHCO$_3$ (2×10 mL). The aq phases were extracted with dichloromethane (10 mL). The combined organic phases were dried (Na$_2$SO$_4$), filtered and evaporated in vacuo to give a yellow liquid that was purified by DCVC (Ø 1 cm, 0-80% EtOAc in n-heptane v/v, 2.5% increments, 10 mL fractions). Fractions containing nucleoside 60 were combined and evaporated in vacuo to afford a white powder (36 mg, 47% from 31). $R_f$=0.38 (80% EtOAc in n-heptane, v/v); ESI-MS m/z found 455.0 ([MH]$^+$, calcd 455.1); $^1$H NMR (DMSO-d$_6$) δ11.38 (br s, 1H, NH), 7.50 (d, J=1.1, 1H, H6), 7.36-7.27 (m, 5H, Ph), 5.77 (s, 1H, H1'), 4.68 (d, J=11.7, 1H), 4.61 (d, J=11.7, 1H), 4.60 (d, J=11.7, 1H), 4.56 (d, J=11.5, 1H) (H5', CH$_2$Ph), 4.20 (d, J=1.8, 1H, H3'), 4.00 (d, J=2.0, 1H, H2'), 3.29 (s, 3H, Ms), 3.02 (d, J=10.6, 1H, H1"a), 2.90 (d, J=10.4, 1H, H1"b), 1.78 (s, 3H, CH$_3$); $^{13}$C NMR (DMSO-d$_6$) δ 163.9 (C4), 150.1 (C2), 137.5, 134.1, 128.3, 127.7 (C6, Ph), 108.3 (C5), 90.5 (C1'), 86.6 (C4'), 76.9 (C3'), 70.9, 66.8 (C5', CH$_2$Ph), 49.5 (C2'), 36.8 (Ms), 35.1 (C1'), 12.3 (CH$_3$); Anal. calcd for C$_{19}$H$_{22}$N$_2$O$_7$S$_2$.0.33EtOAc: C, 50.5; H, 5.1; N, 5.8. Found: C, 50.8; H, 5.1; N, 5.8.

9-(3-O-benzyl-5-O-(methanesulfonyl)-4-C-[[(methanesulfonyl)oxy]methyl]-2-O-trifluormethanesulfonyl-α-L-threo-pentofuranosyl)-6-N-benzoyladenine (62)

Compound 61[1] (9.58 g, 15 mmol) was concentrated from dry acetonitrile in order to remove residual water. The residue was dissolved in dry dichloromethane (100 ml) and cooled to −30° C. while stirred under Ar. The solution was added dry pyridine (3.6 ml, 44 mmol), followed by dropwise addition of Tf$_2$O (3.7 ml, 22 mmol). The reaction mixture was allowed to reach 0° C. TLC (eluent: EtOAc) shows full conversion to product (R$_f$=0.66). The reaction was quenched by addition of sat. NaHCO$_3$-soln. (100 ml) and diluted with dichloromethane (100 ml). The layers were separated and the org. layer was washed with sat. NaHCO$_3$-soln (100 ml), brine (100 ml), dried (Na$_2$SO$_4$), filtered and the solvent removed in vacuo to afford an orange foam, which was purified by dry column chromatography (eluent: Heptane→EtOAc) to afford pure triflate 62 (8.53 g, 74% yield). R$_f$=0.60 (eluent: EtOAc). ESI-MS m/z found 780.0 ([MH]$^+$, calcd 780.0); $^1$H-NMR (CDCl$_3$, 400 MHz): δ 9.05 (1H, s, N—H), 8.80 (1H, s, base), 8.21 (1H, s, base), 8.00 (2H, d, J=7.3 Hz, Bz), 7.61 (1H, t, J=7.3 Hz, Bz), 7.52 (2H, t, J=7.3 Hz, Bz), 7.41-7.30 (5H, m, Bn), 6.56 (1H, t, J=5.5 Hz, H-2'), 6.34 (1H, d, J=5.5 Hz, H-1'), 4.81 (2H, d, J=10.4 Hz, CH$_2$), 4.73 (1H, d, J=5.9 Hz, H-3'), 4.65 (1H, d, J=11.3 Hz, CH$_2$), 4.44 (1H, d, J=11.3 Hz, CH$_2$), 4.34 (1H, d, J=11.1 Hz, CH$_2$), 4.14 (1H, d, J=11.4 Hz, CH$_2$), 3.05 (3H, s, OMs), 2.91 (3H, s, OMs); $^{13}$C-NMR (CDCl$_3$, 100 MHz): δ 164.34, 152.94, 151.26, 149.88, 141.55, 135.07, 133.24, 132.84, 128.98, 128.83, 128.80, 128.49, 127.70, 86.49, 85.03, 83.62, 80.33, 74.49, 67.51, 67.22, 37.76 (OMs), 37.41 (OMs);$^1$ Compound 61 was made according to procedure described in JACS, 124, p. 2164-2176 (2002). Triflate 62 is also described in this article, but not as an isolated product.

(1S,3R,4S,7R)-7-benzyloxy-3-(6-N-benzoyladenin-9-yl)-2,5-dioxabicyclo[2.2.1]heptane (53)

Pure 62 (100 mg, 0.128 mmol) was dissolved in THF (7 ml), cooled to 0° C. and added 1 M LiOH (1.3 ml, 10 equiv.). The reaction mixture was allowed to slowly reach r.t. When LCMS confirmed full conversion of 62 to 63, the reaction was neutralized with 1 M HCl satd. with NaCl (1.3 ml), diluted with DCM (20 ml) and brine (10 ml). Layers were separated and the aqueous layer was extracted with DCM (2×20 ml). Comb. organic layers were dried (Na$_2$SO$_4$), filtered and the solvent removed in vacuo to afford a clear oil (63)$^2$ (quantitative yield). R$_f$=0.49 (Eluent: EtOAc). ESI-MS m/z found 552.2 ([M1-1]$^+$, calcd 552.1); $^1$H-NMR (CDCl$_3$, 400 MHz): 8.64 (1H, s, N—H), 8.44 (1H, s, Adenin), 7.95 (2H, d, J=7.1 Hz, Bz), 7.50 (1H, t, J=7.3 Hz, Bz), 7.40 (1H, t, J=7.3 Hz, Bz), 7.07-6.79 (5H, m, OBn), 6.11 (1H, s, H-1'), 4.66 (1H, d, J=11.5 Hz, CH$_2$), 4.61 (1H, d, J=11.5 Hz, CH$_2$), 4.48 (1H, d, J=1.8 Hz, H-2'/H-3'), 4.30 (1H, d, J=11.9 Hz, CH$_2$), 4.12 (1H, d, J=11.9 Hz, CH$_2$), 4.07 (1H, d, J=1.8 Hz, H-3'/H-2'), 4.02 (1H, d, J=8.6 Hz, CH$_2$), 3.94 (1H, d, J=8.6 Hz, CH$_2$), 3.02 (3H, s, OMs); $^{13}$C-NMR (CDCl$_3$, 100 MHz): δ 165.31, 152.03, 150.45, 148.54, 141.99, 135.38, 132.90, 132.84, 128.63, 128.37, 128.26, 127.98, 127.88, 121.34, 87.90, 86.16, 79.84, 76.29, 73.45, 72.51, 67.76, 64.47, 37.48 (OMs). $^2$Compound 63 is also described in JACS 124, p. 2164-2176 (2002) but not as an isolated product.

1-(2-azido-3-O-benzyl-4-C-methanesulfonyloxymethyl-5-O-methanesulfonyl-2-deoxy-α-L-erythro-pentofuranosyl)-6-benzoyl adenine-9-yl (64)

Not quite pure 62 (6.23 g, 0.008 mol) was dissolved in dry DMF (70 ml), added NaN$_3$ (5.2 g, 10 equiv.) and allowed to stir at r.t. for 3 days. Quenched by addition of water (100 ml) and diluted with DCM (200 ml). Layers were separated and the org. layer was washed with brine (2×125 ml), dried (Na$_2$SO$_4$) and the solvent removed in vacuo. The residue was purified by dry column liquid chromatography (eluent: heptane→EtOAc) to afford pure 64 (5.38 g, quantitative yield). R$_f$=0.60 (Eluent: EtOAc). ESI-MS m/z found 673.0 ([MH]$^+$, calcd 673.1); $^1$H-NMR (CDCl$_3$, 400 MHz): δ 9.14 (1H, s), 8.70 (1H, s), 8.93 (1H, s), 8.00 (3H, d, J=7.3 Hz), 7.59-7.50 (3H, 2×t, J=7.3 Hz), 7.41-7.37 (5H, m), 6.51 (1H, d, J=4 Hz, H-1), 4.92 (1H, d, J=11.7 Hz), 4.77 (1H, d, J=11.3 Hz), 4.75 (1H, d, J=4.8 Hz, H-3), 4.70 (1H, d, J=11.3 Hz), 4.50 (1H, dd, J=4.2 Hz, J=4.6 Hz, H-2), 4.41 (2H, d, J=11-12 Hz), 4.27 (1H, d, J=11 Hz), 3.05 (3H, s, OMs), 3.02 (3H, s, OMs). $^{13}$C-NMR (CDCl$_3$, 100 MHz): δ 164.4, 162.3, 152.5, 151.1, 149.3, 142.1, 135.5, 133.3, 132.6, 128.9, 128.8, 128.8, 128.7, 128.4, 127.6, 122.3 (A$^{Bz}$ and OBn), 82.35, 81.79, 79.55, 74.58 (OBn), 68.51, 68.06, 62.59, 37.78 (OMs), 37.57 (OMs)

(1S,3R,4R,7S)-7-Benzyloxy-1-methansulfonyloxymethyl-3-(6-benzoyladenin-9-yl)-2-oxa-5-azabicyclo[2:2:1]heptane (65).

To a solution of 64 (2.28 g, 3.4 mmol) in THF (100 ml) at rt aq NaOH (2.0 M, 34 ml) and PMe$_3$ in THF (1.0 M, 7 ml) was added with stirring. After over night at r.t. the THF was partly removed under reduced pressure. Brine (100 mL) and EtOAc (200 mL) was added and the phases were separated. The org. layer was washed with brine (100 ml). The comb. aqueous layer was extracted with dichloromethane (200 mL). The combined organic phases were dried (Na$_2$SO$_4$), filtered and concentrated in vacuo to give a yellow foam (1.73 g) which was purified by dry column liquid chromatography to afford pure nucleoside 65 (848 mg) as a yellow foam. R$_f$=0.13 (EtOAc). *Comb. with residues from similar reactions before purification; R$_f$=0.21 (eluent: EtOAc). ESI-MS m/z found 551.1 ([MH]$^+$, calcd 551.1); $^1$H NMR (DMSO-d$_6$, 400 MHz): δ 11.18 (1H, br s, NH), 8.77 (1H, s, A$^{Bz}$), 8.73 (1H, s, A$^{Bz}$), 8.06 (2H, d, J=7.3 Hz), 7.64 (1H, t, J=7.3 Hz, Bz), 7.55 (2H, t, J=7.3 Hz, Bz), 7.45 (2H, d, J=7.2 Hz, Bn), 7.38 (2H, t, J=7.2 Hz, Bn), 7.31 (1H, t, J=7.2 Hz, Bn), 6.52 (1H, d, J=1.6 Hz, H-1'), 4.74 (1H, d, J=11.9 Hz, H-5' a/H-1"a), 4.65 (1H, d, J=11.9 Hz, H-5' b/H-1"b), 4.59 (1H, d, J=11.9 Hz, H-1"a/H-5' a), 4.52 (1H, d, J=11.8 Hz, H-1"b/H-5' b), 4.44 (1H, s, H-3'), 4.04 (1H, d, J=7.2 Hz, Bn), 4.01 (1H, d, J=7.2 Hz, Bn), 3.91 (1H, br s, H-2'), 3.22 (3H, s, OMs); $^{13}$C-NMR (DMSO-d$_6$, 100 MHz): δ 170.34, 165.59, 152.12, 151.47, 150.09, 143.20, 137.89, 133.44, 132.43, 128.48, 128.31, 127.70, 125.19 (Bz and Bn), 87.30, 84.45, 80.47, 71.13 (Bn), 66.99, 59.92, 59.80, 51.27, 36.93 (OMs)

2',3'-epoxide (66)

To a solution of 62 (50 mg) in dry DCM (1.5 ml) at r.t. was added MsOH (0.5 ml) dropwise. Reaction was stirred at r.t. until full conversion of s.m. was confirmed by LCMS. Reaction was diluted with DCM (20 ml), cooled to 0° C., neutralized with Et$_3$N (1.1 ml), washed with sat. NaHCO$_3$-soln (20 ml), brine (20 ml), dried (Na$_2$SO$_4$), filtered and the solvent removed in vacuo to afford a clear oil (66) (49 mg, quantitative yield). R$_f$=0.24 (eluent: EtOAc). ESI-MS m/z found 540.2 ([MH]$^+$, calcd 540.1); $^1$H NMR (CDCl$_3$, 400 MHz): δ 9.3 (1H, br s, N—H), 8.67 (1H, s, base), 8.33 (1H, s, base), 7.94 (2H, d, J=7.5 Hz), 7.51 (1H, t, J=7.4 Hz), 7.42 (2H, t, J=7.5 Hz), 6.61 (1H, s, H-1'), 4.57 (1H, d, J=11.3 Hz), 4.47 (1H, d, J=10.8 Hz), 4.44 (1H, d, J=11.3 Hz), 4.36 (1H, d, J=10.8 Hz), 4.25 (1H, d, J=2.7 Hz, H-2'/H-3'), 4.13 (1H, d, J=2.7 Hz, H-3'/H-2'), 3.11 (3H, s, OMs), 3.01 (3H, s, OMs); $^{13}$C-NMR (CDCl$_3$, 100 MHz): δ 164.7, 152.6, 151.5, 149.4, 141.3, 133.2, 132.6, 128.6, 128.6, 128.3, 128.3, 127.7, 122.2 ($A^{Bz}$), 81.45, 81.23, 68.64, 66.58, 57.59, 57.27, 37.66 (OMs), 37.50 (OMs);

1-(2-azido-3-O-benzyl-4-C-methanesulfonyloxymethyl-5-O-methanesulfonyl-2-deoxy-α-L-threo-pentofuranosyl)-6-benzoyl adenine-9-yl (67)

To a solution of 66 (50 mg, 0.093 mmol) in anh. DMF (2 ml) was added NaN$_3$ (60 mg, 10 equiv.). The mixture was heated to 50° C. overnight. LCMS confirms full conversion of 66 to 67. Reaction mixture was diluted with water (15 ml) and DCM (15 ml). Layers were separated and the org. layer was washed with brine (15 ml), dried (Na$_2$SO$_4$), filtered and the solvent removed in vacuo to afford 67 (43 mg, 80% yield). R$_f$=0.51 (eluent: EtOAc). ESI-MS m/z found 583.0 ([MH]$^+$, calcd 583.1); $^1$H NMR (CDCl$_3$, 400 MHz): δ 11.27 (1H, s, N—H), 8.79 (1H, s, base), 8.05 (2H, d, J=7.3 Hz, Bz), 7.95 (1H, s, base), 7.65 (1H, t, J=7.5 Hz), 7.55 (2H, t, J=7.5 Hz), 6.70 (1H, d, J=5.5 Hz, H-1'), 6.18 (1H, d, J=8.6 Hz, 3'-OH), 5.27 (1H, t, J=8.6 Hz, H-3'), 4.66 (1H, d, J=10.7 Hz, CH$_2$), 4.57 (1H, dd, J=5.6 Hz, J=8.5 Hz, H-2'), 4.47 (1H, d, J=10.8 Hz, CH$_2$), 4.41 (2H, d, J=10.8 Hz, CH$_2$), 3.29 (3H, s, OMs), 3.22 (3H, s, OMs); $^{13}$C-NMR (CDCl$_3$, 100 MHz): δ 165.67, 162.33, 152.33, 152.20, 150.75, 142.63, 133.28, 132.56, 128.57, 128.52, 125.52, 82.34, 81.79, 74.77, 69.00, 68.46, 66.11, 36.87 (OMs), 35.85 (OMs)

(1R,3R,4R,7S)-7-hydroxy-1-methansulfonyloxymethyl-3-(6-benzoyladenin-9-yl)-2-oxa-5-thiobicyclo[2:2:1]heptane (68)

Compound 66 (1.0 g, 1.9 mmol) was dissolved in dry DMF and added Na$_2$S (290 mg, 2 equiv.). Reaction turns green. Allowed to stir at r.t. overnight. LCMS confirms full conversion of compound 1. Reaction mixture was partitioned between brine (100 ml) and EtOAc (100 ml). Layers were separated and the aq. layer was extracted with EtOAc (2×100 ml) and DCM (2×100 ml). Combined organic layer was washed with brine (200 ml), dried (Na$_2$SO$_4$), filtered and the solvent removed in vacuo. Residue was purified by DCLC to afford compound 2 (268 mg, 30% yield). LCMS: found 478.0, calc. 478.0 (M+H). $^1$H-NMR (CDCl$_3$, 400 MHz): δ 9.5-7.3 (8H, $A^{Bz}$), 6.46 (1H, s, H-1), 4.64 (2H, 2×d, J=11.4 Hz, H-1"a and b), 4.56 (1H, d, J=1 Hz, H-3'), 3.75 (1H, d, J=1 Hz, H-2'), 3.04, 5.97 (2H, 2×d, J=10.8 Hz, H-5' a and b), 3.02 (3H, s, OMs).

(1S,3R,4S,7S)-7-Benzyloxy-1-methansulfonyloxymethyl-3-(6-benzoyladenin-9-yl)-2-oxa-5-thiobicyclo[2:2:1]heptane (69)

Compound 62 (3.30 g, 4.2 mmol) was dissolved in dry DMF (33 ml) and added Na$_2$S (1.65 g, 5 equiv.). Reaction colour goes from green to orange in 30 min. LCMS confirms full conversion to compound 2. Reaction mixture was partitioned between sat. NaHCO$_3$-soln. (150 ml) and DCM (150 ml). Layers were separated and the aqueous layer was extracted with DCM (2×75 ml). Combined org. layer was washed with sat. NaHCO$_3$-soln. (150 ml), brine (150 ml), dried (Na$_2$SO$_4$), filtered and the solvent removed in vacuo to afford an oily residue (~3 g) which was used in the next step without further purification. LCMS: found 568.0, calc. 568.1 (M+H). $^1$H-NMR (400 MHz, CDCl$_3$): δ 9.5 (1H, br s, N—H), 8.65 (1H, s, $A^{Bz}$), 8.36 (1H, s, $A^{Bz}$), 7.99 (2H, 2×d, J=7.3 Hz, $A^{Bz}$), 7.54 (1H, t, J=7.3 Hz, $A^{Bz}$), 7.45 (2H, t, J=7.3 Hz, $A^{Bz}$), 7.30-7.36 (5H, m, OBn), 6.61 (1H, d, J=2.2 Hz, H-1'), 4.72 (1H, d, J=11.6 Hz, H-1"a), 4.59 (1H, d, J=11.3 Hz, H-1"b), 4.59 (1H, d, J=1.6 Hz, H-3'), 4.91, (2H, s, OBn), 4.05 (1H, t, J=2.0 Hz, H-2'), 3.17 (1H, d, J=10.5 Hz, H-5' a), 3.05 (1H, d, J=11.0 Hz, H-5' b), 3.02 (3H, s, OMs). $^{13}$C-NMR (100 MHz, CDCl$_3$): δ 152.1, 150.8, 149.2, 141.3, 136.1, 133.4, 132.5, 128.6, 128.6, 128.5, 128.2, 127.8, 127.7, 123.0, ($A^{Bz}$, OBn), 87.34 (C-4'), 87.25 (C-1'), 80.35 (C-3'), 72.05 (C-1"), 66.48 (OBn), 51.80 (C-2'), 37.67 (OMs), 36.00 (C-5').

Compound 70

Compound 69 (2.38 g, 4.2 mmol) was dissolved in dry DMSO (25 ml), added NaOBz (1.24 g, 2 equiv.) and heated to 100° C. overnight. LCMS confirms full conversion to compound 4. Reaction mixture was partitioned between water (150 ml) and DCM (150 ml). Layers were separated and the aqueous layer was extracted with DCM (2×100 ml). Comb. organic layer was washed with brine (2×150 ml), dried (Na$_2$SO$_4$), filtered and concentrated onto silica. Purified by DCLC to afford compound 3 (945 mg, 38% over two steps). LCMS: found 594.2, calc. 594.1 (M+H). $^1$H-NMR (400 MHz, CDCl$_3$): δ 8.63-7.18 (17H, $A^{Bz}$, OBz, OBn), 6.56 (1H, d, J=2.2 Hz, H-1'), 4.72 (1H, d, J=11.5 Hz, H-1"a), 4.69 (1H, d, J=11.0 Hz, H-1"b), 4.57 (1H, d, J=1.6 Hz, H-3'), 4.53 (1H, d, J=11.6 Hz, OBn), 4.49 (1H, d, J=12 Hz, OBn), 4.01 (1H, br s, H-2'), 3.24 (1H, d, J=10.4 Hz, H-5' a), 2.99 (1H, d, J=10.4 Hz, H-5' b). $^{13}$C-NMR (100 MHz, CDCl$_3$): δ 165.5, 152.1, 150.7, 149.2, 141.4, 136.2, 133.5, 133.2, 132.5, 129.5, 129.1, 128.6, 128.4, 128.3, 128.1, 127.7, 127.6 ($A^{Bz}$, OBz, OBn), 87.73 (C-4'), 87.32 (C-1'), 80.47 (C-3'), 71.88 (C-1"), 61.73 (OBn), 51.80 (C-2'), 36.43 (C-5').

Compound 71

Compound 70 (966 mg, 1.627 mmol) was dissolved in dry DCM (27 ml) and added MsOH (9 ml). Stirred at r.t. for 1 hr. LCMS confirms full debenzylation.* Reaction mixture was diluted with DCM (30 ml), washed with brine (50 ml), sat. NaHCO$_3$-soln. (50 ml), dried (Na$_2$SO$_4$), filtered and the solvent removed in vacuo to afford compound 6 (739 mg, 90% yield). LCMS: found 504.1, calc. 504.1 (M+H). *Depurination is also detected, so cooling might be advantageous.

Compound 73

Compound 71 (739 mg, 1.468 mmol) was dissolved in THF (60 ml) and added 1 M LiOH (7.5 ml). The reaction was stirred at r.t. More 1 M LiOH (1 ml) was added after 90 min. Completion of reaction was confirmed by TLC (eluent: EtOAc/MeOH 9:1) after another 60 min. The reaction was quenched with 1 M HCl satd. with NaCl (8.5 ml) and the mixture was partitioned between brine (100 ml) and EtOAc (100 ml). Layers were separated and the aqueous layer was extracted with EtOAc (2×100 ml). Combined org. layer was washed with brine (100 ml), dried (Na$_2$SO$_4$), filtered and the solvent removed in vacuo to afford a yellow solid (compound 72), which was co-evaporated with dry pyridine. The residue was dissolved in dry pyridine (25 ml), added DMAP (180 mg, 1 equiv.) followed by DMTCI (597 mg, 1.2 equiv.) and stirred at r.t. Added more DMTCI (200 mg). TLC (eluent: EtOAc/MeOH 9:1) after 24 hrs shows full conversion to compound 73. Reaction was diluted with DCM (100 ml) and washed with water (100 ml). Aqueous layer was extracted with DCM (50 ml) and combined org. layer was washed with sat. NaHCO$_3$-soln. (100 ml), brine (100 ml), dried (Na$_2$SO$_4$), filtered and the solvent removed in vacuo to afford a residue which was purified by DCLC to afford compound 6 (518 mg, 50% over two steps). LCMS: found 702.2, calc. 702.2 (M+H).

Compound 74

Compound 73 (518 mg, 0.738 mmol) was dissolved in DCM (10 ml), added 1 M DCI (520 μl, 0.7 equiv., dissolved in acetonitrile) followed by bisamidite reagent (244 μl, 1 equiv.) and stirred at r.t., under an atmosphere of $N_2$. More bisamidite reagent was added (2×40 µl) and the flask was transferred to the fridge over weekend. LCMS confirms full conversion to amidite. The reaction mixture was diluted with DCM (100 ml), washed with sat. $NaHCO_3$-soln. (2×100 ml), brine (100 ml), dried ($Na_2SO_4$), filtered and the solvent removed in vacuo to afford compound 74 (642 mg, 97% yield). LCMS: found 902.2, calc. 903.3 (M+H).

9-(2-O-3-Acetyl-3-O-benzyl-5-O-methanesulfonyl-4-C-methanesulfonyloxymethyl-β-L-threo-furanosyl)-2-amino-6-chlorpurine (75)

1,2-Di-O-acetyl-5-O-methanesulfonyl-4-C-methanesulfonyloxymethyl-3-O-benzyl-L-threo-pentofuranose (20.6 g, 40.0 mmol) is dissolved in anh. 1,2-dichloroethane (250 mL) and 2-amino-6-chlorpurine (7.5 g, 44.4 mmol) was added followed by N,O-bis(trimethylsilyl)acetamide (19.6 mL, 80.0 mmol). The reaction mixture was refluxed until it turned clear (1 h) and cooled to room temperature. Trimethylsilyl triflate (14.5 mL, 80.0 mmol) was added over 15 min and the reaction mixture was refluxed for 3 h. The reaction mixture was allowed to cool to room temperature and was poured into sat. aq $NaHCO_3$ (500 mL). $CHCl_3$ (300 mL) was added and after 30 min of vigorous stirring the mixture was transferred to a separatory funnel. The phases were separated and the aq-phase was extracted with $CHCl_3$ (3×250 mL). The combined organic phases were washed with sat. aq $NaHCO_3$: brine (1:1, 500 mL), dried ($Na_2SO_4$), filtered and evaporated in vacou to give a red foam. The product was purified by Dry Column Vacuum Chromatography (Ø 10 cm, 50-100% EtOAc in n-heptane v/v, 10% increments, 2×100 mL fractions, followed by: 1-10% MeOH in EtOAc v/v, 1% increments, 100 ml fractions). The fractions containing nucleoside 75 were pooled and evaporated in vacou to give a white foam (15.6 g, 65%). Further was isolated the N7 isomere (2.0 g). Compound 75: $R_f$=0.59 (10% MeOH in EtOAc, v/v), ESI-MS m/z found 620.1; 622.0 ([MH]$^+$, calcd. 620.1). $^1$H NMR ($CDCl_3$, 400 MHz): δ 8.03 (s, 1H, H8), 7.38-7.29 (m, 5H, Ar—H), 6.14 (d, 1H, J=3.3 Hz, H1'), 5.90 (dd (looks like t), 1H, J=3.3 Hz and 3.0 Hz, H2'), 5.29 (s br, 2H, $NH_2$), 4.78 (d, 1H, J=10.6 Hz, $CH_2$), 4.70 (d, 1H, J=11.3 Hz, $CH_2$), 4.67 (d, 1H, J=11.8 Hz, $CH_2$), 4.44 (d, 1H, J=11.3 Hz, $CH_2$), 4.37 (d, 1H, J=10.6 Hz, $CH_2$), 4.37 (d, 1H, J=3.0 Hz, H3'), 3.01 (s, 3H, Ms), 2.96 (s, 3H, Ms), 2.14 (s, 3H, Ac). $^{13}$C NMR ($CDCl_3$, 100 MHz): δ 169.4 ($CH_3C(O)$), 159.1, 153.2, 151.7 (C2, C4, C6), 140.4 (C8), 136.5, 128.8, 128.5, 128.4 (Ph), 125.3 (C5), 87.0 (C1'), 85.4 (C4'), 81.2 (C3'), 78.8 (C2'), 73.4 ($CH_2$), 67.5, 65.8 (2×$CH_2$), 37.7, 37.6 (2×Ms), 20.6 ($CH_3C(O)$). Anal. calcd. for $C_{22}H_{26}ClN_6O_{10}S_2$: C, 42.6; H, 4.2; N, 11.3. Found: C, 42.5; H, 4.2; N, 11.0.

9-(3-O-benzyl-5-O-methanesulfonyl-4-C-methanesulfonyloxymethyl-β-L-threo-furanosyl)-2-amino-6-chlorpurine (76)

Compound 75 (5.0 g, 8.1 mmol) is dissolved in methanol (100 mL) and cooled to 0° C. and sat. methanolic ammonia (100 ml) was added. The mixture was stirred at 0° C. for 1 h and then the reaction was quenched by neutralisation with glacial acetic acid (app. 30 mL). Sat. aq $NaHCO_3$ (100 mL) and $CHCl_3$ (100 mL) was added and after 5 min of vigorous stirring the mixture was transferred to a separatory funnel. The phases were separated and the aq-phase was extracted with $CHCl_3$ (3×200 mL). The combined organic phase was dried ($Na_2SO_4$), filtered and the solvent removed in vacuo to afford 76 (4.60 g, 99%) as a white solid. $R_f$=0.67 (EtOAc). ESI-MS m/z found 578.1; 580.0 ([MH]$^+$, calcd. 578.1). $^1$H NMR ($CD_3CN$, 400 MHz): δ 8.03 (s, 1H, H8), 7.41-7.33 (m, 5H, Ar—H), 5.86 (d, 1H, J=6.2 Hz, H1'), 5.71 (s br, 2H, $NH_2$), 5.90 ("q", 1H, J=4.6 Hz, H2'), 4.82 (d, 1H, J=11.5 Hz, $CH_2$), 4.72 (d, 1H, J=11.5 Hz, $CH_2$), 4.68 (d, 1H, J=11.0 Hz, $CH_2$), 4.44-4.32 (m, 5H, $CH_2$(3), H3', OH), 3.10 (s, 3H, Ms), 2.98 (s, 3H, Ms). $^{13}$C NMR ($CD_3CN$, 100 MHz): δ 160.6, 154.7, 151.5, 142.3 (C2, C4, C6, C8), 138.4, 129.3, 129.0, 128.9 (Ph), 125.8 (C5), 88.4 (C1'), 83.8, 83.6 (C2', C4'), 77.5 (C3'), 73.9 ($CH_2$), 69.6, 69.5 (2×$CH_2$), 37.7, 37.5 (2×Ms). Anal. calcd. for $C_{22}H_{26}ClN_5O_{10}S_2$: C, 42.6; H, 4.2; N, 11.3. Found: C, 42.5; H, 4.2; N, 11.0.

9-(3-O-benzyl-5-O-methanesulfonyl-4-C-methanesulfonyloxymethyl-2-O-trifluoromethanesulfonyl-β-L-threo-furanosyl)-2-amino-6-chlorpurine (77)

Compound 75 (4.50 g, 7.8 mmol) was dissolved in anh. $CH_3CN$ (2×50 mL) and concentrated in vacuo to remove water traces. The compound was dissolved in anh. dichloromethane (50 mL) and anh pyridine (6.30 mL, 77.8 mmol) was added followed by the addition of DMAP (3.80 g, 31.1 mmol). After cooling to 0° C. trifluoromethanesulfonic anhydride (2.57 mL, 15.6 mmol) was added dropwise during 20 min. The reaction mixture was stirred for an additional 40 min and ice cooled sat. aq $NaHCO_3$ (100 mL) was added and after 5 min of vigorous stirring the mixture was transferred to a separatory funnel. The phases were separated and the aq phase was extracted with $CH_2Cl_2$ (2×100 mL). The combined organic phase was washed successively with aq HCl (0.1 M, 2×100 mL) and sat. aq $NaHCO_3$ (100 mL), dried ($Na_2SO_4$), filtered and evaporated in vacuo. The residue was purified by DCVC (Ø=6 cm, 0-100% EtOAc in n-heptane v/v, 5% increments, 100 mL fractions) yielding nucleoside 77 (5.05 g, 91%) as a white powder. $R_f$=0.18 (1:1 EtOAc in n-heptane v/v). ESI-MS m/z found 710.0; 711.9 ([MH]$^+$, calcd. 710.0). $^1$H NMR (DMSO-$d_6$, 400 MHz): δ 8.45 (s, 1H, H8), 7.42-7.36 (m, 5H, Ar—H), 7.16 (br. s, 2H $NH_2$), 6.48-6.48 (m, 2H), 5.02 (dd, 1H, J=6.2, 1.6 Hz), 4.85 (dd, 2H, J=10.8, 1.1 Hz), 4.67 (d, 1H, J=11.0 Hz), 4.57-4.48 (m, 3H), 3.34 (s, 3H, Ms), 3.18 (s, 3H, Ms). $^{13}$C NMR (DMSO-$d_6$, 100 MHz): δ 160.0, 153.8, 150.2, 141.2 (C2, C4, C6, C8), 136.4, 128.5, 128.5, 128.4 (Ph), 123.4 (C5), 117.7 (q, J=319.7 Hz, $CF_3$), 87.0 (C1'), 80.8, 80.2 (C3', C4'), 73.8 ($CH_2$), 68.6, 68.4 (2×$CH_2$), 59.8 (C2'), 36.9, 36.5 (2×Ms). Anal. calcd. for $C_{21}H_{23}ClF_3N_5O_{11}S_3$.0.25 EtOAc: C, 36.1; H, 3.4; N, 9.6. Found: C, 36.1; H, 3.2; N, 9.5. NOTE: $^{19}$F was also recorded and showed only a single peak.

(1S,3R,4S,7R)-7-benzyloxy-1-(mesyloxymethyl)-3-(guanin-9-yl)-2,5-dioxabicyclo[2.2.1]heptane (78)

3-Hydroxypropionitrile (3.55 mL, 52 mmol) was dissolved in anh. THF (75 mL) and cooled to 0° C. Sodiumhydride (60% in mineral oil, 2.50 g, 62.4 mmol) was added in portions and the temperature was allowed to raise to rt and the mixture was stirred for 30 min at rt. The reaction mixture was cooled to 0° C. again and 9-(3-O-benzyl-5-O-methanesulfonyl-4-C-methanesulfonyloxynnethyl-2-O-trifluoromethanesulfonyl-β-L-threo-furanosyl)-2-amino-6-chlorpurine (77) (7.37 g, 10.4 mmol) dissolved in anh. THF (75 mL) was added dropwise over 20 min and the temperature was allowed to raise to rt. After 8 h the reaction was quenched by addition of HCl (1 M, aq):brine (1:9, 250 mL) and the mixture was transferred to a separatory funnel. The phases were separated and the aq.-phase was extracted with EtOAc (3×200 mL). The combined organic phases were dried ($Na_2SO_4$), filtered and evaporated in vacuo to give a red oil. The product was purified by first filtration through a short silica plug (Ø 6 cm, 10% MeOH in EtOAc v/v, 500 mL) and the resulting material was then precipitated from EtOH:H$_2$O (1:1) resulting in 78 as a tan solid (4.64 g, 96%). R$_f$=0.31 (10% MeOH in EtOAc v/v); ESI-MS m/z found 464.1 ([MH]$^+$, calcd. 464.1); $^1$H NMR (DMSO-d$_6$, 400 MHz): δ=10.63 (s br, 1H, NH), 7.72 (s, 1H, H8), 7.30-7.24 (m, 3H, Ar—H), 7.16-7.11 (m, 2H, Ar—H), 6.65 (s br, 2H, NH$_2$), 5.86 (s, 1H, H1'), 4.83 (d, 1H, J=11.5 Hz, H1"), 4.71 (d, 1 H, J=11.4 Hz, H1"), 4.60 (d, 1H, J=1.8 Hz, H2'/H3'), 4.52 (d, 1H, 3=11.9 Hz, PhCH$_2$), 4.34 (d, 1H, J=11.9 Hz, PhCH$_2$), 4.27 (d, 1H, J=1.8 Hz, $\overline{H2'}$/H3'), 4.08 (d, 1 H, J=8.4 Hz, $\overline{H5'}$), 3.86 (d, 1H, J=8.2 Hz, H5'), 3.27 (s, 3H, Ms); $^{13}$C NMR (DMSO-d$_6$, 100 MHz): δ=156.7 (C6), 153.8 (C2), 150.5 (C4), 137.0 (Ph), 135.6 (C8), 128.3, 127.9, 127.9 (Ph), 116.2 (C5), 86.8 (C4'), 85.5 (C1'), 80.2 (C3'), 76.4 (C2'), 72.5, 72.2 (PhCH$_2$, C5'), 66.4 (C1"), 36.8 (Ms). Anal. calcd. for C$_{19}$H$_{21}$N$_5$O$_2$S: C, 49.2; H, 4.6; N, 15.1. Found: C, 49.4; H, 4.5; N, 15.2.

(1S,3R,4S,7R)-7-benzyloxy-1-(benzoyloxymethyl)-3-(guanin-9-yl)-2,5-dioxabicyclo[2.2.1]heptane (79)

Compound 78 was dissolved in DMSO (25 mL) and BzONa (2.22 g, 15.24 mmol) was added. Heated to 100° C. for 6 h and then to 120° C. for 3 h. The reaction was diluted with EtOAc (50 mL) and quenched with water:sat. aq. NaHCO$_3$ (1:1, 100 mL). The phases were separated and the aq phase was extracted with EtOAc (3×50 mL). The comb. org. phases were washed with Brine (2×100 mL) dried (Na$_2$SO$_4$), filtered and concentrated. The product was purified by Dry Column Vacuum Chromatagry (Ø 4 cm, 0-15% MeOH in dichloromethane v/v, 1% increments, 100 mL fractions). The fractions containing nucleoside 79 were pooled and evaporated in vacuo to give a white solid (1190 mg, 95%). R$_f$=0.15 (5% MeOH in DCM v/v); ESI-MS m/z found 488.3 ([M−H]$^-$, calcd. 488.2); $^1$H NMR (DMSO-d$_6$, 400 MHz): δ=10.63 (s, 1H, NH), 7.95 (d, 2H, J=7.3 Hz, Bz), 7.67 (s, 1H, H8), 7.64 (t, 1H, J=7.3 Hz, Bz), 7.50 (t, 3H, J=7.3 Hz, Bz), 7.24-7.18 (m, 3H, Bn), 7.12-7.06 (m, 2H, Bn), 6.54 (br s, 2H. —NH$_2$), 5.86 (s, 1H, H1'), 4.79 (s, 2H, H1"), 4.59 (d, 1H, J=1.8 Hz, H2'/H3'), 4.49 (d, 1H, J=11.9 Hz, PhCH$_2$O), 4.34 (d, 1H, J=11.9 Hz, PhCH$_2$O), 4.29 (d, 1H, J=1.8 $\overline{Hz}$, H2'/H3'), 4.11 (d, 1H, J=8.4 $\overline{Hz}$, H5' a), 3.93 (d, 1H, J=8.2 Hz, H5' b); $^{13}$C NMR (DMSO-d$_6$, 100 MHz): δ=165.3 (C(O)Ph), 156.7, 153.8, 150.1 (C2, C4, C6), 137.0 (Bn), $\overline{135}$.5 (C8), 133.7 (Bz), 129.4, 129.1, 128.9, 128.3, 127.9 (Ph), 116.3 (C5), 86.8, 85.9 (C4', C1'), 80.0, 76.4 (C2', C3'), 72.7, 72.2 (Ph$\underline{CH_2}$, C5'), 60.6 (C1")

(1R,3R,4S,7R)-3-(guanin-9-yl)-7-hydroxy-1-hydroxymethyl-2,5-dioxabicyclo-[2.2.1]heptane (80)

Compound 79 (2.33 g, 4.16 mmol) was suspended in MeOH (100 mL) and Pd(OH)$_2$—C (20%, 292 mg, 10% mol Pd) and ammonium formiat (5.24 g; 83.2 mmol) were added. The mixture was heated to reflux. After 4 h further Pd(OH)$_2$—C (20%, 292 mg, 10% mol Pd) was added and after an additional 4 h the last Pd(OH)$_2$—C (20%, 292 mg, 10% mol Pd) was added. Reflux for another 12 h.

The catalysis was removed by filtration through paper, the filter paper with catalyst was boiled in MeOH for 30 min and then filter again. The two methanolic solutions are pooled and filtered through Celite. The Celite was washed thoroughly with hot MeOH. All the methanolic solutions were pooled and concentrated. Taken up in H$_2$O and lyophilized twice resulted in 79 as white solid. (1100 mg, 90%). R$_f$=0.01 (10% MeOH in EtOAc v/v); ESI-MS m/z found 296.1 ([MH]$^+$, calcd. 296.1); $^1$H NMR (D$_2$O, 400 MHz): δ=7.90 (s, 1H, H8), 5.91 (s, 1H, H1'), 4.74 (d, 1H, J=2.4 Hz, H2'/H3'), 4.40 (d, 1H, J=2.4 Hz, H2'/H3'), 4.12 (d, 1H, J=8.6 Hz, H5'), 4.02 (d, 1H, J=8.7 Hz, H5'), 4.01 (s, 2H, H5'); $^{13}$C NMR (D$_2$O, 100 MHz): δ=158.7 (C6), 153.7 (C2), 150.8 (C4), 138.4 (C8), 115.4 (C5), 88.7 (C4'), 86.3 (C1'), 78.1 (C3'), 73.2, 72.4 (C2', C5'), 57.4 (C1"); Anal. calcd. for C$_{11}$H$_{13}$N$_5$O$_5$.H$_2$O: C, 42.2; H, 4.8; N, 22.4. Found: C, 42.0; H, 4.5; N, 22.2.

(1S,3R,4S,7R)-1-(4,4'-dimethoxytrityloxymethyl)-3-(2-N-((dimethylamino)methylidene)-7-hydroxy-guanin-9-yl)-2,5-dioxabicyclo[2.2.1]heptane (82)

Compound 80 (860 mg, 2.91 mmol) was dissolved in anh. DMF (25 mL) and N,N-Dimethylformamide dimethyl acetal (0.77 mL, 5.83 mmol) was added. After 4 h the reaction was completed and most of the DMF was remove in vacuo. The resulting slurry 81 was coevaporated twice from anh. pyridine (2×25 mL) and suspended in anh. pyridine (10 mL). 4,4'-dimethoxytritylchloride (1.48 g, 4.37 mmol) was added and the reaction mixture was stirred for 16 h at rt. Most of the pyridine was removed in vacuo and the residue was taken up in DCM (50 mL) and washed with half sat. aq. NaHCO$_3$ (2×50 mL) and brine (50 mL). The comb. aq. phases were extracted with DCM (2×50 mL) and the comb. org. phases were dried (Na$_2$SO$_4$), filtered and evaporated in vacuo to give a yellow foam. The product was purified by Dry Column Vacuum Chromatography (Ø 4 cm, 0-10% MeOH in DCM v/v, 0.5% increments, 100 ml fractions). The fractions containing nucleoside 82 were pooled and evaporated in vacuo to give a white foam (1.10 g, 58%). R$_f$=0.08 (10% MeOH in EtOAc, v/v); ESI-MS m/z found 653.3 ([MH]$^+$, calcd. 653.3; $^1$H NMR (DMSO, 400 MHz): δ=11.29 (s, 1H, NH), 8.57 (s, 1H, N=CH), 7.87 (s, 1H, H8), 7.46-7.40 (m, 2H, DMT), 7.35-7.22 (m, 7H, DMT), 6.93-6.88 (m, 4H, DMT), 6.00 (s, 1H, H1'), 5.92 (d, 1H, J=3.8 Hz, H2'), 4.51 (d, 1H, J=2.0 Hz, OH), 4.21 (dd, 1H, J=3.5, 2.2 Hz, H3'), 4.05 (d, 1H, J=8.2 Hz, H1"), 3.98 (d, 1H, J=8.2 Hz, H1"), 3.74 (s, 6H, OCH$_3$), 3.51 (d, 1H, J=10.2 Hz, H5'), 3.38 (d, 1H, J=10.2 Hz, H5'), 3.33 (s, 3H, NCH$_3$), 3.15 (s, 3H, NCH$_3$); $^{13}$C NMR (DMSO, 100 MHz): δ 158.0 (DMT), 157.8, 157.4, 157.1 (C2, C6, N=CH), 149.2 (C4), 144.5 (DMT), 137.3 (C8), 135.2 (DMT), 129.6, 129.6, 127.7, 127.5, 126.6 (DMT), 118.9 (C5), 113.1 (DMT), 87.3, (C4'), 86.1 (C1'), 85.5 (DMT), 78.1 (C3'), 73.0, 72.7 (C1", C2'), 60.0 (C5'), 54.9 (OCH$_3$), 40.5, 34.6 (N(CH$_3$)$_2$); Anal. calcd. for C$_{35}$H$_{36}$N$_6$O$_7$.H$_2$O: C, 62.7; H, 5.7; N, 12.5. Found: C, 62.8; H, 5.4; N, 12.6.

(1S,3R,4S,7R)-1-(4,4'-dimethoxytrityloxymethyl)-7-(2-cyanoethoxy(diisopropylamino)phosphinoxy)-3-[2-N—((N',N'-dimethylamino)methylidene)-guanin-9-yl]-2,5-dioxabicyclo[2.2.1]heptane (83)

Compound 82 (750 mg, 1.15 mmol) was dissolved in anh DMF (25 mL) and 4,5-dicyanoimidazole in MeCN (1.0 M, 0.80 mL, 0.8 mmol) was added at ambient temperature with stirring. 2-Cyanoethyl-N,N,N',N'-tetraisopropylphosphorodiamidite (0.40 mL, 1.26 mmol) was added dropwise to the reaction mixture. After 4 h the reaction was diluted with EtOAc (70 mL) and transferred to a separatory funnel and extracted with sat. aq NaHCO$_3$ (2×50 mL) and brine (50 mL). The combined aq phases were extracted with EtOAC (100 mL). The organic phases were pooled and dried (Na$_2$SO$_4$). After filtration the organic phase was evaporated in vacuo to give a yellow foam. Purification by DCVC (Ø 2 cm, 1-10% MeOH, EtOAc, v/v, 0.5% increments, 50 mL fractions (the column was pretreated with 1% Et$_3$N in EtOAc v/v)) afforded amidite 83 (480 mg, 49%) as a white solid. R$_f$=0.50 (1%, TEA, 10% MeOH in DCM v/v/v); ESI-MS m/z found 853.2 ([MH]$^+$, calcd. 853.4); $^{31}$P NMR (CDCl$_3$ 121 MHz) δ 151.7, 150.3.

(1S,3R,4S,7R)-7-benzyloxy-3-(2-amino-6-chloro-purine-9-yl)-1-(methanesulfonyloxymethyl)-2,5-dioxabicyclo[2.2.1]heptane (84)

Compound 77 (7.44 g, 10.4 mmol) was dissolved in THF (300 mL). After cooling to 0° C. aq LiOH (1.0M, 105 mL) was added. The reaction mixture was stirred at 0° C. for 4 h and then for additional 2 h at rt. The reaction was quenched by addition of aq HCl (1.0M, sat. with NaCl, 100 mL) and after 5 min of vigorous stirring the mixture was transferred to a separatory funnel. The phases were separated and the aq-phase was extracted with EtOAc (3×150 mL). The combined organic phase was washed with brine:sat. aq NaHCO$_3$ (1:1, 200 mL), dried (Na$_2$SO$_4$), filtered and evaporated in vacuo. The residue was purified by DCVC (Ø=6 cm, 50-100% EtOAc in n-heptane v/v, 5% increments, 2×100 mL fractions) yielding nucleoside 84 (4.49 g mg, 89%) as a white powder. R$_f$=0.49 (20% n-heptane in EtOAc (v/v)). ESI-MS m/z found 482.1.; 484.0 ([MH]$^+$, calcd. 482.1). $^1$H NMR (DMSO-d$_6$, 400 MHz): δ 8.09 (s, 1H, H8), 7.26-7.19 (m, 3H, Ar—H), 7.08-7.04 (m, 2H, Ar—H), 7.01 (br. s, 2H, NH$_2$), 5.96 (s, 1H, H1'), 4.86 (d, 1H, J=11.3 Hz, H5"), 4.76 (d, 1H, J=11.3 Hz, H5"), 4.65 (d, 1H, J=2.0 Hz, H2'), 4.51 (d, 1H, J=11.9 Hz, CH$_2$), 4.32 (d, 1H, J=11.7 Hz, CH$_2$), 4.31 (d, 1H, J=2.0 Hz, H3'), 4.10 (d, 1H, J=8.2 Hz, CH$_2$), 3.89 (d, 1H, J=8.4 Hz, CH$_2$), 3.28 (s, 3H, Ms). $^{13}$C NMR (DMSO-d$_6$, 100 MHz): δ 159.6, 153.0, 149.0 (C2, C4, C6), 140.8 (C8), 136.7, 128.0, 127.8, 127.7 (Ph), 123.2 (C5), 86.8 (C4'), 85.6 (C1'), 80.0 (C3'), 75.8 (C2'), 72.3, 72.2 (C5', CH$_2$Ph), 66.2 (C5"), 36.6 (Ms).

(1S,3R,4S,7R)-7-benzyloxy-3-(2-amino-6-chloro-purine-9-yl)-1-(benzoyloxymethyl)-2,5-dioxabicyclo[2.2.1]heptane (85)

Compound 84 (4.49 g, 9.32 mmol) was dissolved in DMSO (200 mL) and BzONa (6.76 g, 46.6 mmol) was added. The reaction was stirred at 100° C. for 16 h. The reaction allowed to cool to room temperature and EtOAc (200 mL) and brine: sat. aq NaHCO$_3$ (1:1, 400 mL) was added. The mixture was transferred to a separatory funnel. The phases were separated and the aq-phase was extracted with EtOAc (3×200 mL). The combined organic phase was washed with brine (half-sat., 2×200 mL), dried (Na$_2$SO$_4$), filtered and evaporated in vacuo. The residue was purified by DCVC (Ø=6 cm, 50-100% EtOAc in n-heptane v/v, 5% increments, 2×100 mL fractions, 0-10% MeOH in EtOAc v/v, 1% increments, 100 mL) yielding nucleoside 85 (3.30 g, 70%) as a white powder. R$_f$=0.40 (35% n-heptane in EtOAc (v/v)). ESI-MS m/z found 508.2.; 510.1 ([MH]$^+$, calcd. 508.1). $^1$H NMR (DMSO-d$_6$, 400 MHz): δ 8.05 (s, 1H, H8), 7.98 (d, 2H, J=7.3 Hz, Bz), 7.68 (t, 1H, J=7.3 Hz, Bz), 7.53 (t, 2H, J=7.7 Hz, Bz), 7.25-7.15 (m, 3H, Bn), 7.05-7.00 (m, 4H, Bn, NH$_2$), 5.98 (s, 1H, H1'), 4.85 (s, 2H, H5"), 4.67 (d, 1H, J=1.8 Hz, H2'), 4.50 (d, 1H, J=12.1 Hz, CH$_2$), 4.35 (d, 1H, J=2.0 Hz, H3'), 4.34 (d, 1H, J=11.7 Hz, CH$_2$), 4.16 (d, 1H, J=8.4 Hz, CH$_2$), 3.98 (d, 1H, J=8.1 Hz, CH$_2$). $^{13}$C NMR (DMSO-d$_6$, 100 MHz): δ 165.1 (PhCO), 159.6, 152.9, 149.0 (C2, C4, C6), 140.6 (C8), 136.7, 133.5, 129.2, 128.9, 128.7, 128.0, 127.9, 127.7, 127.6 (Ph), 123.2 (C5), 86.7 (C4'), 85.9 (C1'), 79.9 (C3'), 75.8 (C2'), 72.5, 72.1 (5', CH$_2$Ph), 60.4 (C5").

9-(3-O-Benzyl-2-deoxy-2-iodo-5-O-methanesulfo-nyl-4-C-(methanesulfonyloxymethyl)-β-D-threo-pentofuranosyl)-6-N-benzoyladenine (87)

9-(3-O-Benzyl-5-O-methanesulfonyl-4-C-(methanesulfonyloxymethyl)-2-O-trifluoromethanesulfonyl-β-D-erythro-pentofuranosyl)-6-N-benzoyladenine (589 mg, 0.755 mmol) was dissolved in dry acetonitrile (15 ml), added lithiumiodide (202 mg, 2 equiv.) and heated to reflux. After 2 hrs, LCMS shows full conversion. Solvent was removed in vacuo and the residue was partitioned between DCM (50 ml) and water (50 ml). Layers were separated and the organic layer was washed with brine (50 ml), dried (Na$_2$SO$_4$), filtered and the solvent removed in vacuo to afford an orange foam (514 mg, 90% yield)

9-(2-azido-3-O-Benzyl-2-deoxy-5-O-methanesulfo-nyl-4-C-(methanesulfonyloxymethyl)-β-D-erythro-pentofuranosyl)-6-N-benzoyladenine (88)

Compound 87 (30 mg) was dissolved in DMF/water 1:1 (2 ml) and followed by sodium azide (26 mg, 10 equiv.). The reaction mixture stirred at 80° C. overnight. LCMS confirms conversion of starting material to product substituted with azide.

The invention claimed is:

1. A method for the synthesis of a compound of the general formula IV

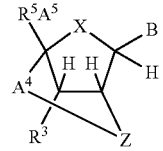

Formula IV wherein

X is —O—

Z is —CH$_2$

B is a nucleobase;

R$^3$ is selected from —R$^H$, —N$_3$, —NR$^H$R$^{H*}$, —NR$^H$C(O)R$^{H*}$, —C(O)NR$^H$R$^{H*}$, —OR$^H$, —OC(O)R$^H$, —C(O)OR$^H$, —SR$^H$, —SC(O)R$^H$, and tri(C$_{1-6}$-alkyl/aryl)silyloxy;

each R$^H$ and R$^{H*}$ independently being selected from hydrogen, optionally substituted C$_{1-6}$-alkyl, optionally substituted aryl, and optionally substituted aryl-C$_{1-6}$-alkyl;

A$^4$ and A$^5$ independently are selected from C$_{1-6}$-alkylene; and

R$^5$ is selected from iodo, bromo, chloro, C$_{1-6}$-alkylsulfonyloxy optionally substituted with one or more substituents selected from halogen and phenyl optionally substituted with one or more substituents selected from nitro, halogen and C$_{1-6}$-alkyl, and arylsulfonyloxy optionally substituted with one or more substituents selected from nitro, halogen, C$_{1-6}$-alkyl, and C$_{1-6}$-alkyl substituted with one or more halogen;

said method comprising the following steps:
treating an intermediate of the general formula I:

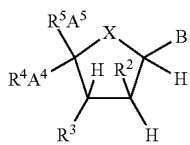

Formula I wherein
X, B, $R^3$, $A^4$, and $A^5$ are as defined above;
$R^2$ is selected from iodo, $C_{1-6}$-alkylsulfonyloxy optionally substituted with one or more substituents selected from halogen and phenyl optionally substituted with one or more substituents selected from nitro, halogen and $C_{1-6}$-alkyl, and arylsulfonyloxy optionally substituted with one or more substituents selected from nitro, halogen, $C_{1-6}$-alkyl, and $C_{1-6}$-alkyl substituted with one or more halogen; $R^3$ and $R^2$ may together form an epoxide and
$R^4$ and $R^5$ independently are as defined for $R^5$ above, or $R^4$ and $R^5$ together constitutes a tetra($C_{1-6}$-alkyl)disiloxanylidene group;
with a nucleophile selected from organometallic hydrocarbyl radicals, so as to substitute $R^2$, and
effecting ring-closure between the C2' and C4' positions so as to yield the LNA analogue of the formula IV.

2. The method according to claim 1, wherein
$R^2$ is selected from $C_{1-6}$-alkylsulfonyloxy optionally substituted with one ore more halogen, and arylsulfonyloxy optionally substituted with one or more substituents selected from nitro, halogen, $C_{1-6}$-alkyl, and $C_{1-6}$-alkyl substituted with one or more halogen;
$R^3$ is optionally substituted aryl($C_{1-6}$-alkyl)oxy; and
$R^4$ and $R^5$ are independently selected from $C_{1-6}$-alkylsulfonyloxy optionally substituted with one or more halogen an arylsulfonyloxy optionally substituted with one or more substituents selected from nitro, halogen, $C_{1-6}$-alkyl, and $C_{1-6}$-alkyl substituted with one or more halogen.

3. The method according to claim 1, wherein $A^4$ and $A^5$ are methylene.

4. The method according to claim 1, wherein $R^4$ and $R^5$ are identical.

5. The method according to claim 1, wherein B is selected from adenine, guanine, 2,6-diaminopurine, thymine, 2-thiothymine, cytosine, methyl cytosine, uracil, 5-fluorocytosine, xanthine, 6-aminopurine, 2-aminopurine, 6-chloro 2-aminopurine, and 6-choropurine, $R^2$ is selected from $C_{1-6}$-alkylsulfonyloxy substituted with one or more halogen, $R^3$ is benzyl, and $R^4$ and $R^5$ are independently selected from $C_{1-6}$-alkylsulfonyloxy optionally substituted with one or more substituents selected from halogen and $C_{1-6}$-alkyl substituted with one or more halogen.

6. The method according to claim 1, wherein $R^4$ and $R^5$ are independently selected from methanesulfonyloxy, trifluoromethanesulfonyloxy, ethanesulfonyloxy, 2,2,2,-trifluoroethanesulfonyloxy, propanesulfonyloxy, iso-propanesulfonyloxy, butanesulfonyloxy, nonafluorobutanesesulfonyloxy, pentanesulfonyloxy, cyclopentanesulfonyloxy, hexanesulfonyloxy, cyclohexanesulfonyloxy, 2-chloro-α-toluenesulfonyloxy, ortho-toluensulfonyloxy, meta-toluenesulfonyloxy, para-toluenesulfonyloxy, benzenesulfonyloxy, ortho-bromobenzenesulfonyloxy, meta-bromobenzenesulfonyloxy, para-bromobenzenesulfonyloxy, ortho-nitrobenzenesulfonyloxy, meta-nitrobenzenesulfonyloxy, and para-nitro-benzenesulfonyloxy.

7. The method according to claim 1, wherein the intermediate has the formula III

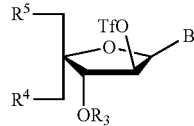

Formula III wherein B, $R^4$ and $R^5$ are as defined in claim 1, and wherein $R^3$ is —$OR^H$ or —$OC(O)R^H$, where $R^H$ is as defined in claim 1.

8. The method according to claim 1, wherein B is selected from adenine, guanine, 2,6-diaminopurine, thymine, 2-thiothymine, cytosine, methyl cytosine, uracil, 5-fluorocytosine, xanthine, 6-aminopurine, 2-aminopurine, 6-chloro-2-aminopurine, and 6-chloropurine, $R^3$ is benzyl, and $R^4$ and $R^5$ are both methylsulfonyloxy.

* * * * *

UNITED STATES PATENT AND TRADEMARK OFFICE
CERTIFICATE OF CORRECTION

PATENT NO. : 8,492,390 B2
APPLICATION NO. : 13/336303
DATED : July 23, 2013
INVENTOR(S) : Mads Detlef Sorensen Page 1 of 1

It is certified that error appears in the above-identified patent and that said Letters Patent is hereby corrected as shown below:

In the Claims

Col. 36, line 45, claim 1, delete "—O—" and insert -- —O—; --

Col. 36, line 46, claim 1, delete "—CH$_2$" and insert -- —CH$_2$—; --

Col. 36, line 56, claim 1, delete "C$_{i-6}$-alkyl;" and insert -- C$_{1-6}$-alkyl; --

Col. 37, line 31, claim 2, delete "one ore more" and insert -- one or more --

Col. 38, line 4, claim 5, delete "6-chloro 2" and insert -- 6-chloro-2 --

Col. 38, line 15, claim 6, delete "nonafluorobutanesesulfonyloxy," and insert -- nonafluorobutanesulfonyloxy, --

Col. 38, line 19, claim 6, delete "ortho-toluensulfonyloxy," and insert -- ortho-toluenesulfonyloxy, --

Signed and Sealed this
Twenty-fourth Day of June, 2014

Michelle K. Lee
*Deputy Director of the United States Patent and Trademark Office*